United States Patent [19]
Taylor et al.

[11] Patent Number: 5,453,091
[45] Date of Patent: Sep. 26, 1995

[54] RF TRANSMISSION MODULE FOR WIRELESSLY TRANSMITTING BALLOON CATHETER DATA IN A SYRINGE INFLATION SYSTEM

[75] Inventors: Steven R. Taylor; Fred P. Lampropoulos; Christopher L. Durham, all of Salt Lake City, Utah

[73] Assignee: Merit Medical Systems, Inc., South Jordan, Utah

[21] Appl. No.: 223,514

[22] Filed: Apr. 5, 1994

Related U.S. Application Data

[60] which is a continuation-in-part of Ser. No. 26,431, Mar. 4, 1993, Pat. No. 5,385,549, which is a continuation of Ser. No. 664,587, Mar. 4, 1991, Pat. No. 5,201,753, which is a continuation-in-part of Ser. No. 324,938, Mar. 17, 1989, Pat. No. 5,135,488.

[51] Int. Cl.$^6$ .............................. A61M 29/00; A61M 1/00
[52] U.S. Cl. ........................ 604/100; 604/121; 128/903
[58] Field of Search .............................. 128/903; 604/97, 604/100, 118, 121

[56] References Cited

U.S. PATENT DOCUMENTS

| | | |
|---|---|---|
| 383,940 | 6/1888 | Brinkerhoff . |
| 404,105 | 5/1889 | Overlach . |
| 446,125 | 2/1891 | Schirmer . |
| 577,682 | 2/1897 | Eissner . |
| 730,054 | 6/1903 | Sheets . |

(List continued on next page.)

FOREIGN PATENT DOCUMENTS

| | | |
|---|---|---|
| 545415 | 8/1957 | Canada . |
| 0119296 | 9/1984 | European Pat. Off. . |
| 0230966A3 | 1/1985 | European Pat. Off. . |
| 0149866 | 7/1985 | European Pat. Off. . |
| 0396353 | 11/1990 | European Pat. Off. . |
| 1242737 | 8/1960 | France . |
| 2083364 | 3/1982 | United Kingdom . |
| WO81/02664 | 10/1981 | WIPO . |
| WO92/17721 | 10/1992 | WIPO . |

OTHER PUBLICATIONS

Product catalog of Mansfield (1988).
Advertisement brochure of Mansfield entitled: "Tha Mansfield Trak Series." (1987).
Advertisement brochure of Mansfield entitled: "The Mansfield Series 3000 Intra–Aortic Balloon Pump". (1988).
Advertisement brochure of Medex, Inc. for Medflator inflation system. (1991).
Advertisement brochure of Mansfield for Digiflator inflation syringe with an attached digital pressure gauge. (Undated).
Mansfield instruction brochure for the Digiflator. (1991).
Advertisement brochure of Condor Medical for Transflator Infrared System. (Undated).

(List continued on next page.)

*Primary Examiner*—John D. Yasko
*Assistant Examiner*—Adam J. Cermak
*Attorney, Agent, or Firm*—Workman Nydegger Seeley

[57] ABSTRACT

An electronically controlled syringe system for connection to a balloon catheter or other balloon-type member and for monitoring, displaying and recording inflation or deflation data when the syringe system is used to inflate or deflate the balloon of the catheter or other balloon-type member. A syringe having a barrel and a syringe plunger is selectively operable to increase fluid pressure applied to the balloon catheter or other balloon member by sliding the plunger further into the barrel. Positive pressure applied to the balloon catheter or member is released by withdrawing the syringe plunger towards the rear of the barrel. A piezoresistive semiconductor transducer placed in fluid communication with the fluid pressure applied by the syringe, senses the fluid pressure and outputs an electrical signal representative of that pressure. The electrical signal is received by a RF transmission module that is permanently mounted to the syringe barrel. The RF transmission module derives transmission data from the electrical pressure signal and wirelessly transmits the transmission data via a radio frequency signal to a remote console. The remote console processes the transmission data so as to monitor, record, and display the inflation or deflation data.

19 Claims, 37 Drawing Sheets

U.S. PATENT DOCUMENTS

| | | | |
|---|---|---|---|
| 1,661,818 | 3/1928 | Cook . | |
| 1,707,880 | 4/1929 | Sheets . | |
| 2,656,836 | 10/1953 | Hickey . | |
| 2,672,866 | 3/1954 | Kater . | |
| 2,699,168 | 1/1955 | Lewis . | |
| 2,724,385 | 11/1955 | Lockhart | 128/261 |
| 2,736,315 | 2/1956 | Feeney | 128/218 |
| 2,764,978 | 10/1956 | Everett | 128/215 |
| 3,080,866 | 3/1963 | Friedman | 128/218 |
| 3,388,941 | 6/1968 | Marcus | 294/4 |
| 3,478,937 | 11/1969 | Solowey | 222/386 |
| 3,491,757 | 1/1970 | Arce | 128/221 |
| 3,529,596 | 9/1970 | Garner | 128/145.6 |
| 3,698,381 | 10/1972 | Federico et al. | 128/1 R |
| 3,720,199 | 3/1973 | Rishton et al. | 128/1 D |
| 3,884,229 | 5/1975 | Raines et al. | 128/221 |
| 3,931,822 | 1/1976 | Marici | 128/351 |
| 3,966,358 | 6/1976 | Heimes et al. | 417/12 |
| 3,985,123 | 10/1976 | Herzlinger et al. | 128/2.05 F |
| 3,992,926 | 11/1976 | Berryhill | 73/80 |
| 4,016,871 | 4/1977 | Schiff | 128/2.06 R |
| 4,057,050 | 11/1977 | Sarstedt | 128/2 F |
| 4,063,662 | 12/1977 | Drummond et al. | 222/31 |
| 4,086,653 | 4/1978 | Gernes | 364/564 |
| 4,106,002 | 8/1978 | Hogue, Jr. | 340/626 |
| 4,182,344 | 1/1980 | Benson | 128/207.15 |
| 4,254,773 | 3/1981 | Waldbillig | 128/348 |
| 4,261,360 | 4/1981 | Perez . | |
| 4,266,550 | 5/1981 | Bruner | 128/349 |
| 4,267,846 | 5/1981 | Kontos | 128/765 |
| 4,285,340 | 8/1981 | Gezari et al. | 128/205.24 |
| 4,323,071 | 4/1982 | Simpson et al. | 128/343 |
| 4,332,254 | 6/1982 | Lundquist | 128/344 |
| 4,370,982 | 2/1983 | Reilly | 604/98 |
| 4,384,470 | 5/1983 | Fiore | 73/4 R |
| 4,404,974 | 9/1983 | Titus | 128/670 |
| 4,418,392 | 11/1983 | Hata | 364/571 |
| 4,439,185 | 3/1984 | Lundquist | 604/97 |
| 4,444,335 | 4/1984 | Wood et al. | 222/43 |
| 4,446,715 | 5/1984 | Bailey | 73/1 R |
| 4,446,867 | 5/1984 | Leveen et al. | 128/344 |
| 4,460,355 | 7/1984 | Layman | 604/118 |
| 4,466,426 | 8/1984 | Blackman | 128/1.1 |
| 4,504,268 | 3/1985 | Herlitze . | |
| 4,522,194 | 6/1985 | Normann | 128/1 D |
| 4,526,196 | 7/1985 | Pistillo | 137/557 |
| 4,546,760 | 10/1985 | Suzuki et al. | 128/1 D |
| 4,557,269 | 12/1985 | Reynolds et al. | 128/675 |
| 4,568,335 | 2/1986 | Updike et al. | 604/211 |
| 4,573,978 | 3/1986 | Reilly | 604/240 |
| 4,583,917 | 4/1986 | Shah | 417/63 |
| 4,583,974 | 4/1986 | Kokernak | 604/211 |
| 4,585,010 | 4/1986 | Ascer et al. | 128/673 |
| 4,596,255 | 6/1986 | Snell et al. | 128/697 |
| 4,597,381 | 7/1986 | Oumi et al. | 128/6 |
| 4,600,015 | 7/1986 | Evans et al. | 128/780 |
| 4,601,701 | 7/1986 | Mueller, Jr. | 604/83 |
| 4,610,256 | 9/1986 | Wallace | 128/675 |
| 4,621,646 | 11/1986 | Bryant | 128/692 |
| 4,651,738 | 3/1987 | Demer et al. | 128/344 |
| 4,658,829 | 4/1987 | Wallace | 128/672 |
| 4,662,355 | 5/1987 | Pieronne et al. . | |
| 4,672,974 | 6/1987 | Lee | 128/673 |
| 4,710,179 | 12/1987 | Haber | 604/211 |
| 4,715,854 | 12/1987 | Vaillancourt | 604/191 |
| 4,723,938 | 2/1988 | Goodin et al. | 604/99 |
| 4,743,230 | 5/1988 | Nordquest | 604/97 |
| 4,756,706 | 7/1988 | Kerns et al. | 604/66 |
| 4,758,223 | 7/1988 | Rydell | 604/90 |
| 4,770,189 | 9/1988 | Shyu | 128/773 |
| 4,781,192 | 11/1988 | Demer | 128/344 |
| 4,787,368 | 11/1988 | Kageyama | 600/18 |
| 4,787,429 | 11/1988 | Valentini et al. | 141/383 |
| 4,796,606 | 1/1989 | Mushika | 600/18 |
| 4,799,491 | 1/1989 | Eckerle | 128/672 |
| 4,817,629 | 4/1989 | Davis et al. | 128/748 |
| 4,819,637 | 4/1989 | Dormandy . | |
| 4,820,271 | 4/1989 | Deutsch | 604/99 |
| 4,825,876 | 5/1989 | Beard | 128/675 |
| 4,830,013 | 5/1989 | Maxwell | 128/637 |
| 4,832,692 | 5/1989 | Box et al. | 604/99 |
| 4,838,864 | 6/1989 | Peterson | 604/100 |
| 4,858,615 | 8/1989 | Meinema | 128/668 |
| 4,865,581 | 9/1989 | Lundquist et al. | 600/18 |
| 4,872,483 | 10/1989 | Shah | 137/557 |
| 4,877,035 | 10/1989 | Bogen et al. | 128/673 |
| 4,896,671 | 1/1990 | Cunningham et al. | 128/642 |
| 4,901,731 | 2/1990 | Millar | 128/675 |
| 4,906,244 | 3/1990 | Pinchuk et al. | 606/194 |
| 4,907,596 | 3/1990 | Schmid et al. | 128/672 |
| 4,919,121 | 4/1990 | Rydell et al. | 604/97 |
| 4,940,459 | 7/1990 | Noce | 604/97 |
| 4,974,774 | 12/1990 | Nakagawa et al. | 600/18 |
| 5,004,472 | 4/1991 | Wallace | 606/194 |
| 5,009,662 | 4/1991 | Wallace | 606/192 |
| 5,011,468 | 4/1991 | Lundquist et al. | 600/18 |
| 5,019,041 | 5/1991 | Robinson | 604/97 |
| 5,021,046 | 6/1991 | Wallace | 606/97 |
| 5,024,668 | 6/1991 | Peters et al. | 606/194 |
| 5,059,167 | 10/1991 | Lundquist et al. | 600/17 |
| 5,084,060 | 1/1992 | Freund et al. | 606/192 |
| 5,086,777 | 2/1992 | Hishii | 128/675 |
| 5,135,488 | 8/1992 | Foote et al. | 604/97 |
| 5,215,523 | 6/1993 | Williams et al. | 604/97 |
| 5,259,838 | 11/1993 | Taylor et al. | 604/97 |
| 5,279,563 | 1/1994 | Brucker et al. | 604/98 |
| 5,318,533 | 6/1994 | Adams et al. | 604/97 |
| 5,368,565 | 11/1994 | DeLong | 604/100 |
| 5,383,855 | 1/1995 | Nicholson et al. | 604/100 |

OTHER PUBLICATIONS

Advertisement brochure of VasTek for the Inter/Com Inflation System Computer. (Undated).

Brochure of VasTek disclosing Inter/Com and inflation syringe entitled: "Reach Out and Touch the Future". (Undated).

"ACS Accessories Offer Optimum Efficiency in Your Angioplasty Procedures," Eli Lilly and Company (Undated).

Advertising brochure of North American Instrument Corporation entitled "The NAMIC 10cc Angiographic Syringe Features." (Jul. 1988).

Advertising brochure of Spectramed, Inc.; produce prochure for "CONTROLEASE Disposable Control Syringe"; and product brochure for control syringe of COEUR Laboratories, Inc. (Undated).

"Clearing the Path for a Healthy Heart," *Tristate: The Cincinnati Enquirier Magazine*, Oct. 23, 1988.

"Coronary Angioplasty," Krames Communications, 1985.

"Good News for People with Only Two Hands," SciMed Life Systems, Inc. (Undated).

"Health–Critics of Angioplasty Worry About Inflated Success Claims," *U.S. News & World Report*, Jul. 25, 1988, p. 65.

"Inflation PRO: A New Dual–Support System for Angioplasty," Baxter Healthcare Corporation (Undated).

"PTCA Safe and Efficacious Performed Together With Diagnostic Angiography in Selected Cases," *Cardiovascular News*, May 1988, p. 8.

"USCI Wizard Disposable Inflation Device," C.R. Bard, Inc. (1987).

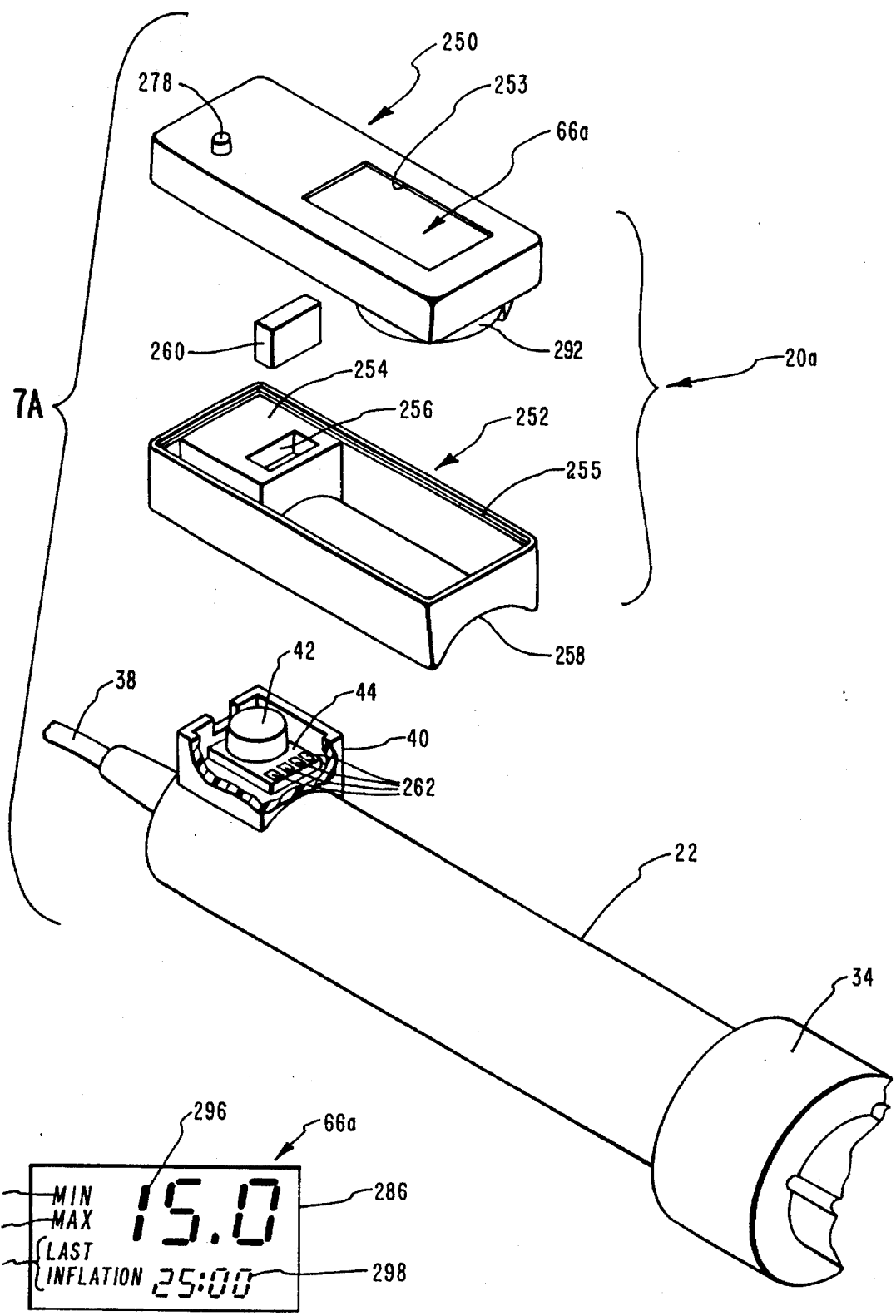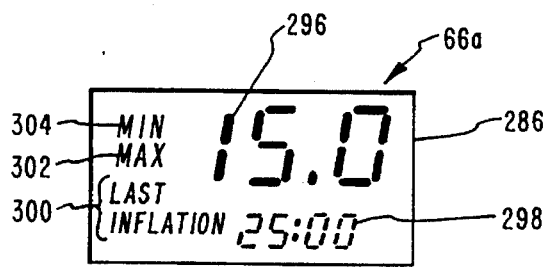

RF TRANSMISSION MODULE FOR WIRELESSLY TRANSMITTING BALLOON CATHETER DATA IN A SYRINGE INFLATION SYSTEM

RELATED APPLICATION INFORMATION

This application is a continuation-in-part of U.S. application Ser. No. 08/026,431 filed Mar. 4, 1993, now U.S. Pat. No. 5,385,349, which is a continuation of U.S. application Ser. No. 07/664,587 filed Mar. 4, 1991, now U.S. Pat. No. 5,201,753, which is a continuation-in-part of U.S. application Ser. No. 07/324,938, filed Mar. 17, 1989, now U.S. Pat. No. 5,135,488.

BACKGROUND OF THE INVENTION

1. Field of the Invention

This invention relates to syringe systems that are used for controlling and monitoring conditions of inflation or deflation of a balloon-tipped catheter, and more particularly to a radio frequency (RF) transmission module that is used to electronically monitor an inflation syringe and to then wirelessly transmit electronic data representative of various inflation data to a remote console for processing and display.

2. The Present State of the Art

Balloon-tipped catheter systems have been known and used in the medical arts for a number of years in connection with a variety of different kinds of procedures which are used, for example, in various fields of medicine, such as urology, gynecology, cardiology and others. Particularly in connection with the treatment of coronary artery disease, the use of balloon-tipped catheters and their associated syringe systems have become widely used.

Coronary artery disease is the narrowing of the arteries that feed oxygen-rich blood to the heart. Since the heart is a muscle whose primary job is to pump oxygenated blood throughout the body, the heart needs adequate amounts of oxygen to properly function. Thus, when the coronary arteries which are located on the top of the heart and through which oxygenated blood is returned to the heart become narrowed or blocked (a condition known as "stenosis"), angina can result. Angina is a symptom of coronary artery disease characterized by chest pain or pressure that can radiate to the arm or jaw, and is caused by a lack of oxygen-rich blood to the heart muscle. Coronary artery disease with its accompanying symptom of angina results from atherosclerosis, which is a build up of waxy material called plaque inside the arteries. When this happens, under exertion or stress, the heart demands more oxygen but the narrowed coronary arteries cannot supply enough oxygen-rich blood to meet the demand, resulting in angina. Unless corrected, this condition can lead to a fatal heart attack.

Initially, there were two basic ways to treat coronary artery blockages: with medicine or by performing coronary artery by-pass surgery. Various kinds of medication could be administered which would decrease the work of the heart by slowing the heart rate, dilating the blood vessels, or lowering blood pressure. However, such medicinal treatment did not cure coronary artery blockage, which thus remained and which would therefore continue to present a risk that at some point the blockage would become serious enough to require surgical intervention.

In coronary artery by-pass surgery, a blood vessel from the chest or leg is grafted beyond the point of blockage so that the blood detours past the blockage in order to reach the heart. In some severe cases, multiple by-passes are performed. As is well known, coronary artery by-pass surgery is expensive, is a high risk procedure and often requires prolonged hospitalization and recovery periods.

Later on, another method for treating coronary artery disease was developed, called balloon coronary angioplasty, or more technically, percutaneous transluminal coronary angioplasty (PTCA). PTCA is a much less traumatic procedure than coronary artery by-pass surgery. PTCA takes about two hours and can be done under local anesthesia, with the result that often a patient can be back on his feet and active in a matter of days. Because PTCA is much less expensive and less traumatic than by-pass surgery and yet in many cases still effectively removes blockage, PTCA has experienced a dramatic increase in the number of such procedures performed each year. Since coronary artery disease remains a major cause of death, PTCA may be expected to continue to play an important role in the treatment of coronary artery disease.

In performing PTCA, an introducer sheath is inserted through an incision made in the groin or arm area into the corresponding artery, such as the femoral artery. An x-ray sensitive dye is injected into the coronary artery through a catheter that is introduced through the sheath. The dye enables the doctor, through the use of real time x-ray techniques, to clearly view the arteries on a television monitor and to thereby locate the artery blockage. A balloon-tipped catheter with a guide wire at the end of it is then advanced through the artery to the point of the blockage with the help of the x-ray monitor.

As schematically illustrated in FIGS. 1A–1C, the balloon catheter 10 is advanced to the middle of the blockage 12. The catheter 10, which is filled with a fluid and is coupled at its other end to an inflation syringe, is manipulated by the cardiologist. Once the balloon catheter is in place, utilizing the inflation syringe the balloon is inflated for 20 to 60 seconds as shown in FIG. 2B. The balloon is then deflated and this procedure is repeated typically several times to compress the plaque on the arterial wall, as shown in FIG. 1C. After the results are checked, the balloon catheter and guide wire are then removed.

As will be appreciated, notwithstanding that PTCA is a much less traumatic procedure than coronary artery by-pass surgery, nonetheless exacting control with respect to inflation pressure and duration of the inflation periods is essential to the safety of the patient. For example, when the balloon catheter is completely inflated so as to begin compressing the plaque, blood flow to a region of the heart is thereby temporarily shut off. This creates a condition known as myocardial ischemia, which can initiate cardiac arrest. Accordingly, the pressure exerted on the artery by the balloon catheter as well as the duration of the blockage created by inflating the balloon catheter must both be carefully controlled by the attending cardiologist and other personnel. The inflation pressures and duration of each inflation must be based on the cardiologist's assessment of the health of the patient and the patient's ability to withstand such a temporary stoppage of blood flow to the heart.

In the past, PTCA syringe systems have been equipped with standard analog or Bourdon-tube gauges that are utilized to sense and read the pressure used for purposes of inflating a balloon catheter. Human observation of stop clocks and the like has been used to control the duration of the inflation.

While these prior art techniques have been widely used with success, there is still a serious risk of human error when using such systems. The gauges used on such syringe systems are often awkward and difficult to accurately read, and are also subject to malfunction. Thus, improper recording of inflation pressure and/or duration may occur. Accordingly, there is a need for the cardiologist and/or clinician to be able to improve the degree of control and precision with respect to the inflation procedure. There is also a need to be able to accurately record the procedure data so that in the event of any later question with respect to whether the procedure was properly carried out, there is an accurate record from which to answer such questions.

Many types of syringe inflation systems have been proposed or used in the art which, to varying degrees, provide for more careful monitoring and/or recording of PTCA data. Two of the first commercially successful syringe inflation systems which provided digital monitoring of PTCA data are the Intellisystem® and Monarch® Syringe Inflation Systems of Merit Medical Systems, Inc., which are produced and sold under U.S. Pat. Nos. 5,135,488 and 5,201,753 (hereinafter the "'488" and "'753" patents) respectively.

The Intellisystem® syringe inflation system provides an inflation syringe with an attached semiconductor transducer mounted to the syringe barrel. The transducer output is connected by an electrical cable to a bedside monitor that digitally processes the transducer signal to provide a digital readout of various PTCA data, including magnitude of each inflation and duration of each inflation and deflation. The Monarch® syringe inflation system provides an inflation syringe that has a miniaturized digital monitor mounted to the syringe barrel in an integral fashion.

After the PTCA procedure is complete, with the Intellisystem® syringe inflation system, the inflation syringe with its attached transducer is disposed of. In the case of the Monarch® syringe inflation system, the syringe with the attached miniature monitor is all completely disposed of.

There is great concern in the health care industry for keeping health care costs as low as possible. Thus, there is an ongoing need to find ways of providing syringe inflation systems which, like the Intellisystem® and Monarch® systems, are effective for monitoring PTCA data, but which are also less costly and further minimize the disposal of costly components.

SUMMARY OF THE INVENTION

The system and method of the present invention have been developed in response to the present state of the art, and in particular, in response to the problems and needs in the art not heretofore fully or completely solved by syringe inflation systems used in connection with PTCA procedures. However, it is not intended that the system and method of the present invention will necessarily be limited solely to PTCA procedures, since they will also find useful application with potentially many kinds of procedures which require the utilization of inflatable balloon members for various kinds of medical procedures. Thus, it is an overall object of the present invention to provide a system and method which provide for a cost effective yet accurate and convenient measurement and monitoring and of a balloon-type member.

Another important object of the present invention is to provide a system and method whereby state of the art electronic technology can be utilized to assist the cardiologist or clinician in accurately measuring and monitoring inflation pressures when utilizing a syringe system to inflate a balloon catheter or other balloon-type member, and which will at the same time automatically electronically record and store the inflation pressure and duration of the inflation so as to permit the data pertaining to the procedure to be later printed out and thus accurately documented and saved for later reference.

Another important object of the present invention is to provide an improved syringe system and electronic monitoring and recording system which increase the convenience and safe utilization of a balloon catheter or other balloon-type inflation member.

Yet another important object of the present invention is to provide an improved syringe system that utilizes an inflation syringe which is easy to use, and inexpensive enough in its construction as to be disposable.

A further object of the present invention is to provide an improved syringe system wherein the inflation or deflation data is electrically monitored, recorded and displayed at a remote system console, which wirelessly receives a radio frequency signal that is generated and transmitted by an RF transmission module mounted to the inflation syringe.

These and other objects and features of the present invention will become more fully apparent from the following more detailed description taken in conjunction with the drawings and claims, or may be learned by the practice of the invention.

Briefly summarized, the foregoing and other objects are achieved in an electronically monitored syringe system that is connected to a balloon catheter or other inflatable balloon-type device through tubing. The syringe comprises a barrel and a plunger selectively operable to increase fluid pressure applied to the balloon through the connecting tubing by sliding the plunger further into the barrel, and to then remove the applied pressure by returning the plunger to the rear of the barrel. A transducer for sensing fluid pressure applied by the syringe is placed in fluid communication with the syringe and the connecting tubing. The transducer thereby senses applied fluid pressure and outputs an electrical signal proportional to the sensed pressure. The electrical signal output by the transducer is then electronically processed so as to derive and record therefrom electronic data representing the magnitude of fluid pressure applied to the balloon or other balloon-type member, and so as also to derive the length of time that inflation pressure is applied to the balloon or other balloon-type member. The electronic data representing these parameters is then automatically displayed and/or recorded. The system also comprises a display for selectively outputting a visual display of the magnitude of the applied pressure and the corresponding length of time that inflation pressure is applied to the balloon or other balloon-type member.

Importantly, the electrical signal output by the transducer is received and electronically processed by a RF transmission module that is permanently mounted to the syringe. The RF transmission module processes the electrical signal into transmission data and then wirelessly transmits the transmission data via a radio frequency signal to a remote console. In this embodiment, the electronic control system and display is incorporated within the remote console, which receives and processes the transmission data, and thereby monitors, displays and/or records the associated inflation or deflation data. Further, the user may control the operations that are performed at the remote console and select the type of inflation data to be displayed on the display, via actuation of control switches that are conveniently located on a control panel that is disposed on the RF transmission module. Thus, a syringe system that utilizes an inflation syringe that is self-contained and sufficiently low in cost so as to be disposable is provided. Further, the system provides for the electronic monitoring of inflation data at a remote display without the need for a cable connection by utilizing low cost RF transmission circuitry, thereby resulting in increased convenience in terms of portability and in maintaining sterility.

BRIEF DESCRIPTION OF THE DRAWINGS

The presently preferred embodiments and the presently understood best mode of the invention will be described with additional detail through use of the accompanying drawings, wherein corresponding parts are designated by the same reference numerals throughout, and in which:

FIG. 7A is a perspective illustration of a portion of the syringe system of FIG. 7, with portions of the electronic controller shown in exploded perspective to more particularly illustrate certain details thereof.

FIG. 7C is an illustration of the digital readout display which particularly illustrates the nature of the information displayed thereon when utilizing the electronic control system and syringe of FIG. 7.

DETAILED DESCRIPTION OF THE PRESENTLY PREFERRED EMBODIMENTS

I. THE SYSTEM

A. General Environment and Intended Utility of the System

Figure 1A:
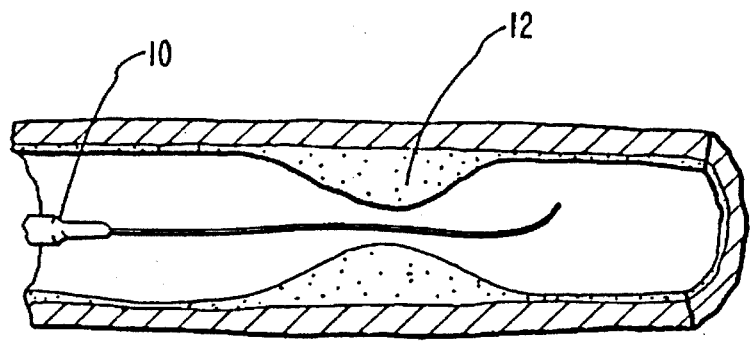
FIGS. 1A–1C are partial cross-sectional views which schematically illustrate a conventional balloon catheter being placed within a vessel such as a coronary artery containing a blockage, and showing the manner in which the blockage is essentially removed by inflation of the balloon catheter.
Figure 1B:
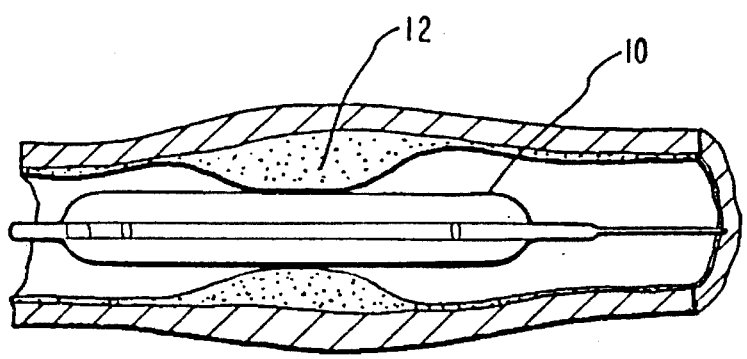
Figure 1C:
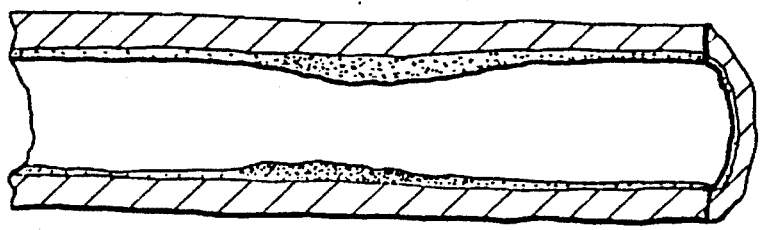

The system and method of the present invention have been developed in response to specific needs which have been found to exist in connection with techniques that are currently in use according to the present state of the art lo which has developed in connection with PTCA procedures. As described in connection with FIGS. 1A–1C, PTCA is a surgical procedure used for treating coronary artery disease wherein a balloon catheter 10 is inserted through an incision made in the groin or in the artery of an arm and is then advanced through the artery by means of a guide catheter and assisted by means of an x-ray sensitive dye. The balloon catheter 10 is advanced until it is located at the middle of the blockage 12. Once located at the middle of the blockage 12, the balloon of catheter 10 is then inflated (see FIG. 1B) to a pressure that is typically between 7 and 10 atmospheres for a duration of between 20 to 60 seconds. The balloon is then deflated and the procedure is repeated a number of times, slightly increasing the inflation pressure each time so as to further compress and thereby reduce the blockage 12 created by the buildup of plaque along the wall of the artery. Once this series of inflations is completed and the artery is cleared, as shown in FIG. 1C, the balloon catheter 10 is removed.

While the system and method of the present invention are particularly useful in connection with the aforementioned PTCA procedure, the system and method of the invention are not intended to be necessarily limited to use in connection with PTCA. Rather, it is contemplated that the system and method of the invention will find useful application with respect to any procedure requiring the use of an inflatable balloon-type member. Moreover, while in PTCA the inflation pressure which is applied to the balloon catheter 10 is applied hydraulically by means of the syringe and connecting tubing which are all filled with a sterile liquid such as a solution of saline and contrast medium, in some potential applications it may be necessary or desirable to apply the inflation pressure pneumatically. Accordingly, as used herein the term "fluid pressure" is intended to apply either to a hydraulically or a pneumatically applied inflation pressure.

Furthermore, as will be appreciated by those of ordinary skill in the art, while the system and method as described in reference to the preferred embodiments herein illustrate the invention as implemented using state of the art digital processing design and corresponding program instructions, the system and method could also be implemented and carried out using a hardware design which accomplishes the necessary electronic processing, which is thus intended to be embraced within the scope of the invention.

B. The Presently Preferred Syringe System and Electronic Controller: FIGS. 2–5, 7–9 and 11–13.

1. FIGS. 2–5

The system of the present invention is comprised of a syringe that is connected to a balloon catheter or other balloon-type member through tubing. The syringe is used to apply fluid pressure to the balloon of the catheter or other balloon-type member through the tubing so as to inflate the balloon or balloon member when desired, and can also be used to deflate the balloon catheter or balloon member after it has been inflated for a selected duration. The system is also comprised of a transducer means for sensing applied fluid pressure and for outputting an electrical signal proportional to the sensed fluid pressure. The transducer means is thus preferably in fluid communication with the syringe and the tubing connected to the balloon catheter or other balloon-type member.

Figure 2:
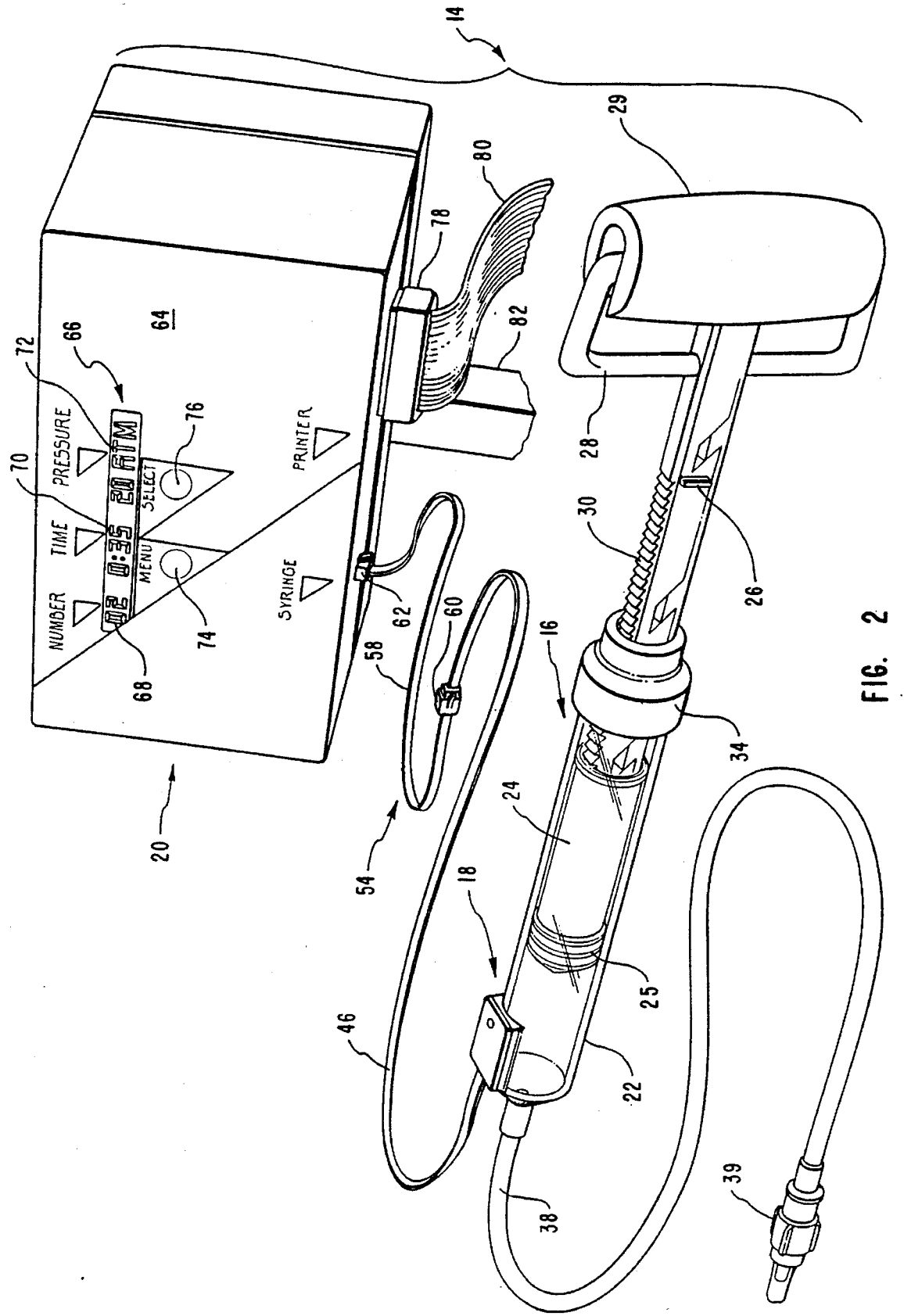
FIG. 2 is a perspective illustration showing the system of the present invention, and in particular illustrating a syringe with tubing for connection to a balloon catheter, and a transducer means mounted on the syringe and electrically connected to an electronic controller.
Figure 3:
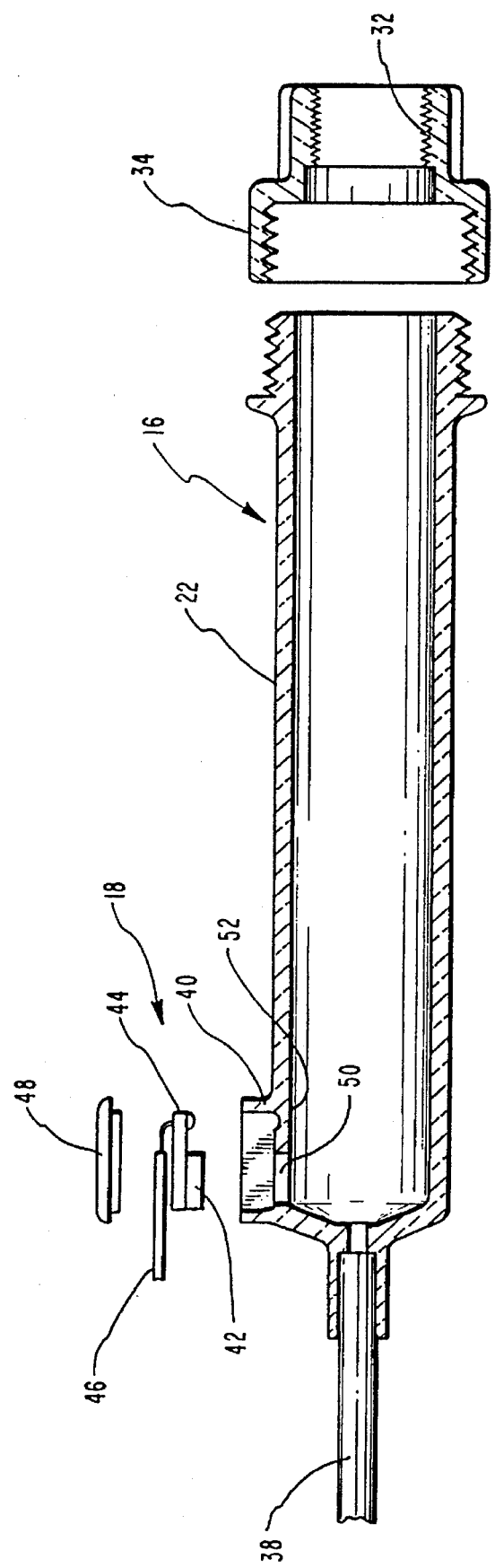
FIG. 3 is a partial cross-sectional view of the syringe barrel that more particularly illustrates one presently preferred structure and method for placing the transducer means in fluid communication with the interior of the syringe and the tubing which is connected to the balloon catheter.

In the preferred embodiment illustrated in FIG. 2, the overall system is generally designated at 14 and the syringe is generally designated at 16. With reference to FIGS. 2 and 3 taken together, the syringe 16 is comprised of a barrel 22 typically molded from transparent plastic material to permit inspection of the contents thereof. A syringe plunger 24 (FIG. 2) is slidably mounted within the barrel and is secured within the barrel 22 by means of a cap 34 which can be threaded onto or otherwise securely attached at the end of the barrel 22. The syringe plunger 24 has a threaded portion 30 which mates with corresponding threads 32 (see FIG. 3) of end cap 34.

The proximal end of plunger 24 is provided with a soft rubber bulb 25 which engages the interior of barrel 22 in a fluid-tight fit such that by sliding the syringe plunger 24 further into the barrel 22, positive pressure exerted on the fluid contained within syringe 16 and connecting tubing 38 will be applied to the balloon catheter which is connected to the tubing 38 by means of a rotatable luer connector 39. Similarly, by withdrawing the syringe plunger 24 toward the rear of the barrel 22, the positive pressure exerted on the balloon catheter will be released.

Rapid movement of the syringe plunger 24 is accommodated by means of a trigger mechanism comprising a spring-activated trigger 28 which can be retracted into handle 29 so as to disengage the threads 30 from the corresponding threads 32 of cap 34. This permits the plunger 24 to freely slide in either direction within the syringe barrel 22. By releasing the compression on trigger 28 relative to handle 29, the threads 30 are then permitted to engage the corresponding threads 32 of cap 34 so that thereafter the syringe plunger 24 can only be advanced or retracted by screwing the plunger 24 either clockwise or counter clockwise, respectively. Thus, rapid application or release of pressure applied to the balloon catheter can be accomplished by compressing the trigger 28 against handle 29 followed by movement of the syringe plunger 24 to the position desired for the approximate pressure to be applied. This can then be followed by release of the trigger 28 and screwing the plunger 24, which will permit a slow, gradual adjustment of the syringe plunger 24 to the exact pressure that is desired.

It will be appreciated that insofar as providing for application and release of positive inflation pressure, this function of syringe 16 of the system could be provided by any of a number of syringe systems which are conventional or known in the art. However, the syringe illustrated and generally described in connection with FIGS. 2 and 3 is presently preferred in connection with the system and illustrates the presently contemplated best mode of the syringe 16. A more complete description of syringe 16 and its unique design and advantages is contained in U.S. application Ser. Nos. 325,561 and 434,460 filed Mar. 17, 1989 and Nov. 13, 1989, now U.S. Pat. Nos. 5,057,078 and 5,047,615 respectively, which are incorporated herein by reference.

The transducer means of the system of the present invention is generally designated in FIGS. 2 and 3 at reference numeral 18. As shown best in FIG. 3, the body of syringe barrel 22 has a small housing 40 formed at the leading end of the barrel as an integral part of the syringe barrel 22. The housing 40 communicates through a small circular opening 50 formed in the sidewall of syringe barrel 22 with the interior of syringe barrel 22 for the purpose of providing fluid communication from the interior of barrel 22 and connecting tubing 38 to the transducer means, as hereinafter more fully described.

As used herein, the term "fluid communication" is intended to mean the pneumatic or hydraulic transmission (direct or indirect) of fluid pressures exerted within the syringe barrel 22 and connecting tubing 38 to the transducer means so that such fluid pressures can be sensed by the transducer means. Direct transmission of such fluid pressures would occur, for example, when a diaphragm of a piezoresistive semiconductor transducer is placed into contact (either pneumatically or hydraulically, or a combination of both) with a fluid contained in a closed system, as would be the case in the preferred embodiments illustrated and described herein. Indirect transmission could be said to occur, for example, where the transducer means is coupled to a diaphragm that in turn contacts the fluid contained in a closed system.

Figure 5A:
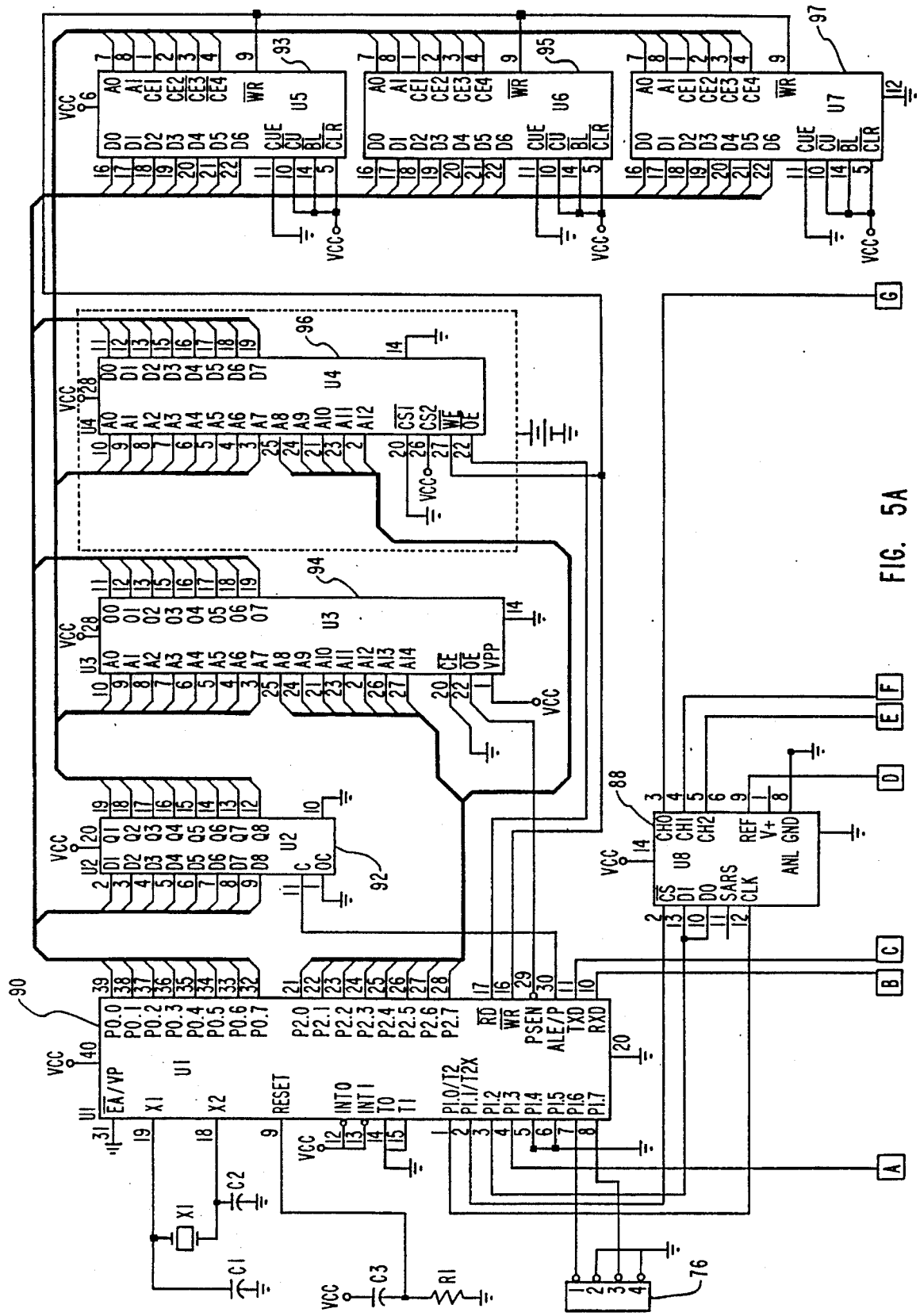
FIGS. 5A and 5B taken together constitute a detailed electrical schematic diagram which illustrate, as an example, the presently preferred embodiment and presently understood best mode for implementing the electronic circuit means of the system and method of the present invention.
Figure 5B:
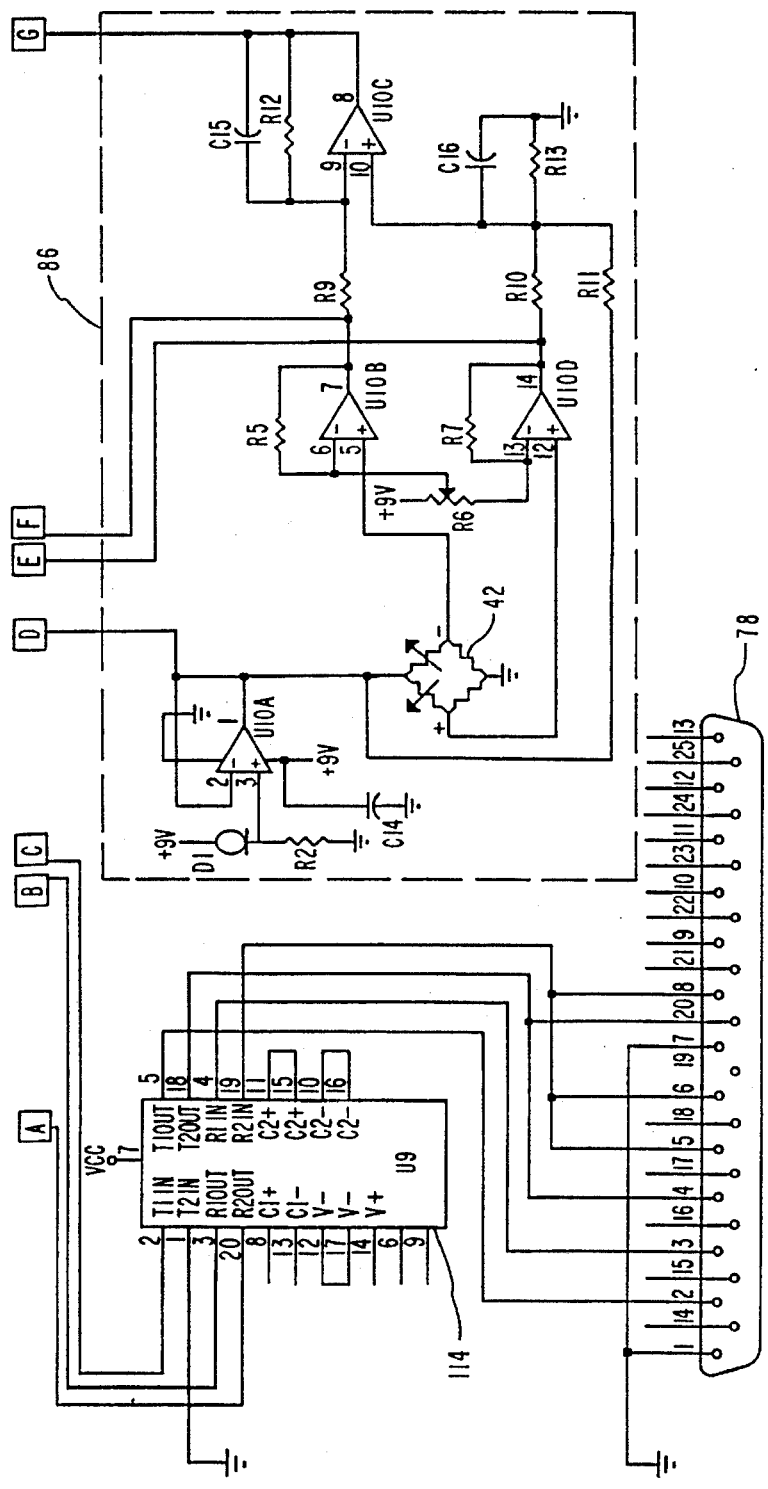
Figure 5B:
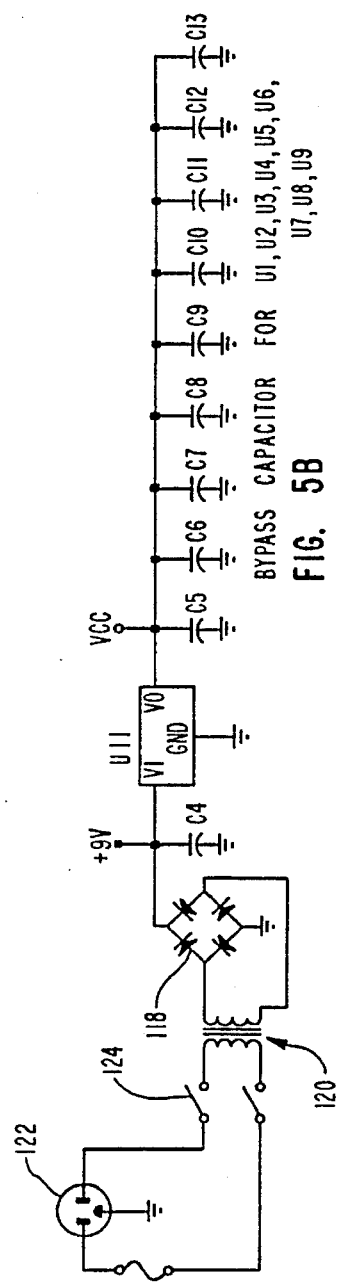
Figure 9A:
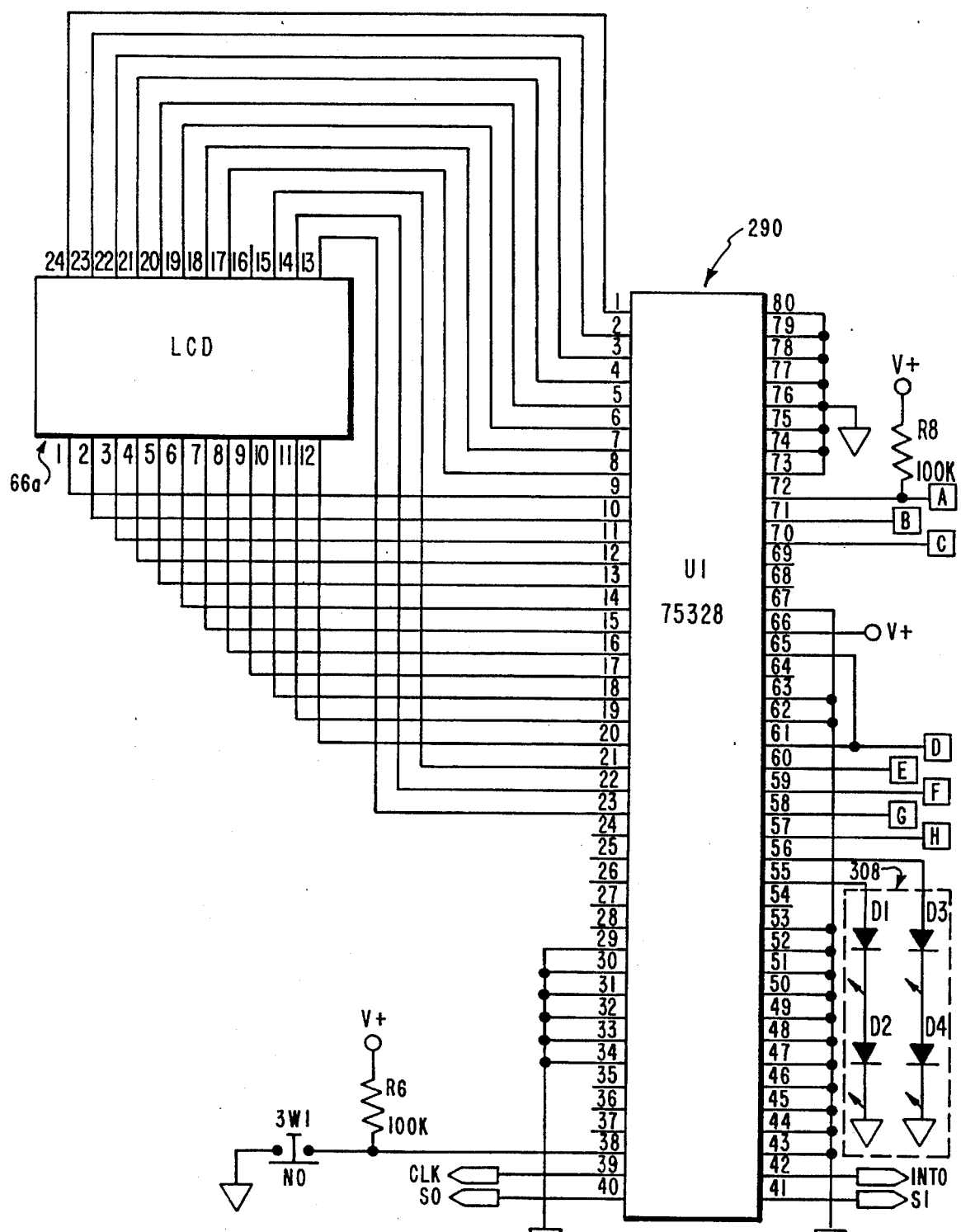
FIGS. 9A and 9B taken together constitute a detailed electrical schematic diagram which illustrate, as an example, the presently preferred embodiment and presently understood best mode for implementing the electronic circuit means of the syringe system of FIG. 7.
Figure 9B:
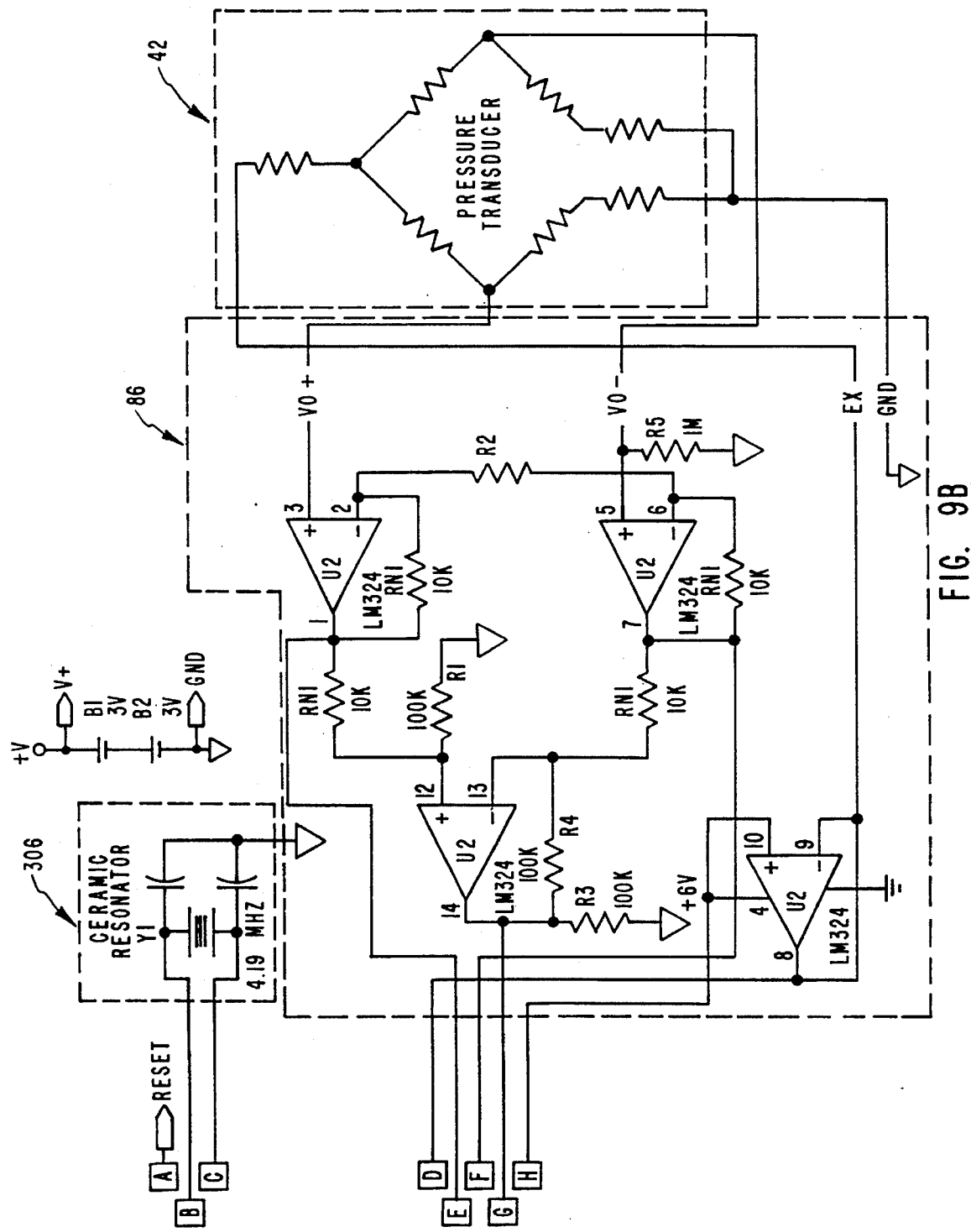

In FIG. 3, the transducer is shown as preferably comprising a piezoresistive semiconductor integrated circuit 42 which provides a Wheatstone bridge, as shown in the detailed electrical schematics at FIGS. 5B and 9B at the corresponding reference numeral. Transducer 42 is in turn attached to a small ceramic substrate 44 which contains additional circuitry for providing temperature compensation and calibration of the transducer 42, and to which is connected the electrical cable 46. The end of electrical cable 46, ceramic substrate 44 and piezoresistive semiconductor transducer 42 are assembled as illustrated in FIG. 3 and placed within housing 40, and then secured by a suitable potting compound and permanently enclosed by means of the cap 48 placed on top of the housing 40. In this manner, the entire transducer assembly is formed as an integral attachment to the syringe barrel 22. Stops 26 (see FIG. 2) are formed on the syringe plunger 24 so as to prevent the bulb 25 of syringe plunger 24 from being inserted to the point where it would otherwise close off the circular opening 50.

The small circular opening 50 may be filled, for example, with a silicone gel which will permit transmission of the fluid pressures exerted by means of syringe 16 through the circular opening 50 so that such pressures can be sensed by transducer 42, while at the same time isolating the integrated circuit 42 and substrate 44 from coming into contact with fluid contained in the syringe barrel 22.

In some prior art type inflation syringes, conventional analog or Bourdon-tube gauges are mounted to the syringe barrel. These types of gauges typically include brass fittings which are in direct contact with the contrast media in the syringe. As a result, highly toxic substances, such as copper sulfate and heavy metal residuals, such as lead, have been found to be present in the contrast media as a result of chemical interaction of the brass fitting with the contrast media. While this is not harmful so long as the balloon is not ruptured, if a rupture does occur this toxic substance is released into the patient's cardiovascular system.

One advantage of the above-described syringe and transducer means is the elimination of materials, such as brass, from which such toxic substances are derived. Furthermore, contact of any sort between the contrast media and the transducer and related circuitry is completely prevented, as noted above, by the silicone gel that isolates such from the contrast media while still providing effective fluidic coupling to the transducer diaphragm.

While in the preferred embodiment the transducer means has been illustrated and described as a piezoresistive semiconductor which is integrally mounted to the syringe barrel 22, it should be appreciated that the preferred embodiment is illustrative only and is not to be construed as limiting the scope of the invention. For example, the semiconductor transducer could be located at the end of connecting tubing attached through a T-connector to tubing 38 and could therefore be located at a position remote from the syringe 16, as for example on an I.V. stand or mounted as part of the electronic circuitry contained inside of controller 20. Furthermore, the transducer means could also comprise transducer types other than the piezoresistive semiconductor type illustrated and described in the preferred embodiment, as for example conventional strain gauge transducers which have been known and used in the art for many kinds of different pressure monitoring applications, or fiberoptic transducers.

With continued reference to FIG. 2, the electronic circuit means and display means of the system of the present invention are illustrated in the preferred embodiment as comprising part of controller 20. The specific electronic circuitry which is used for implementing the controller 20, and its method of use for monitoring, displaying and recording PTCA data as illustrated in FIGS. 2–5 is set forth in U.S. Pat. No. 5,135,488 which is incorporated herein by reference, in its entirety.

2. FIGS. 7–9.

Figure 7:
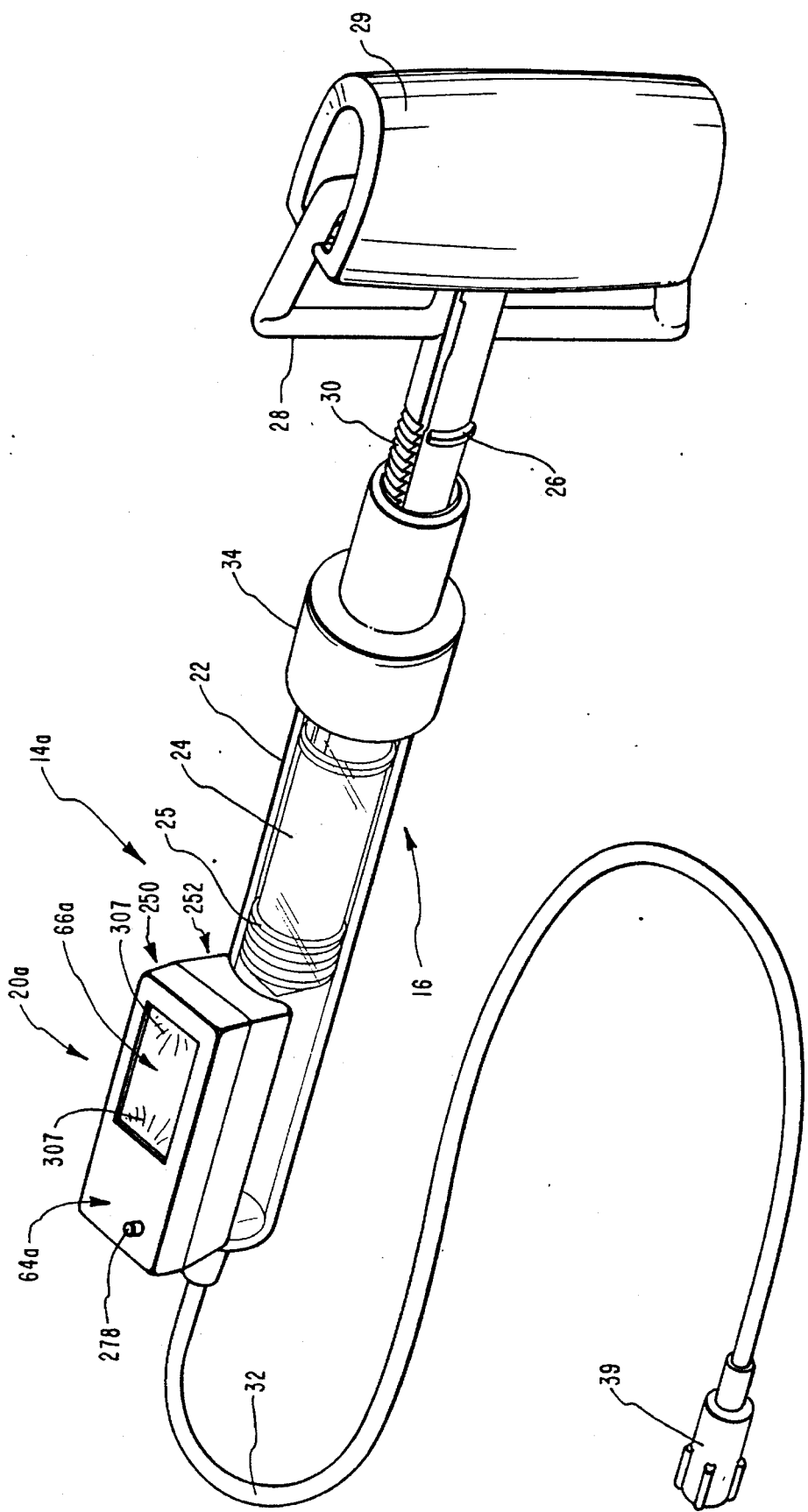
FIG. 7 is a perspective illustration showing a second embodiment of the system of the present invention in which a transducer means together with an electronic controller are all mounted directly onto the syringe barrel so as to form a totally self-contained, disposable syringe system.
Figure 7B:
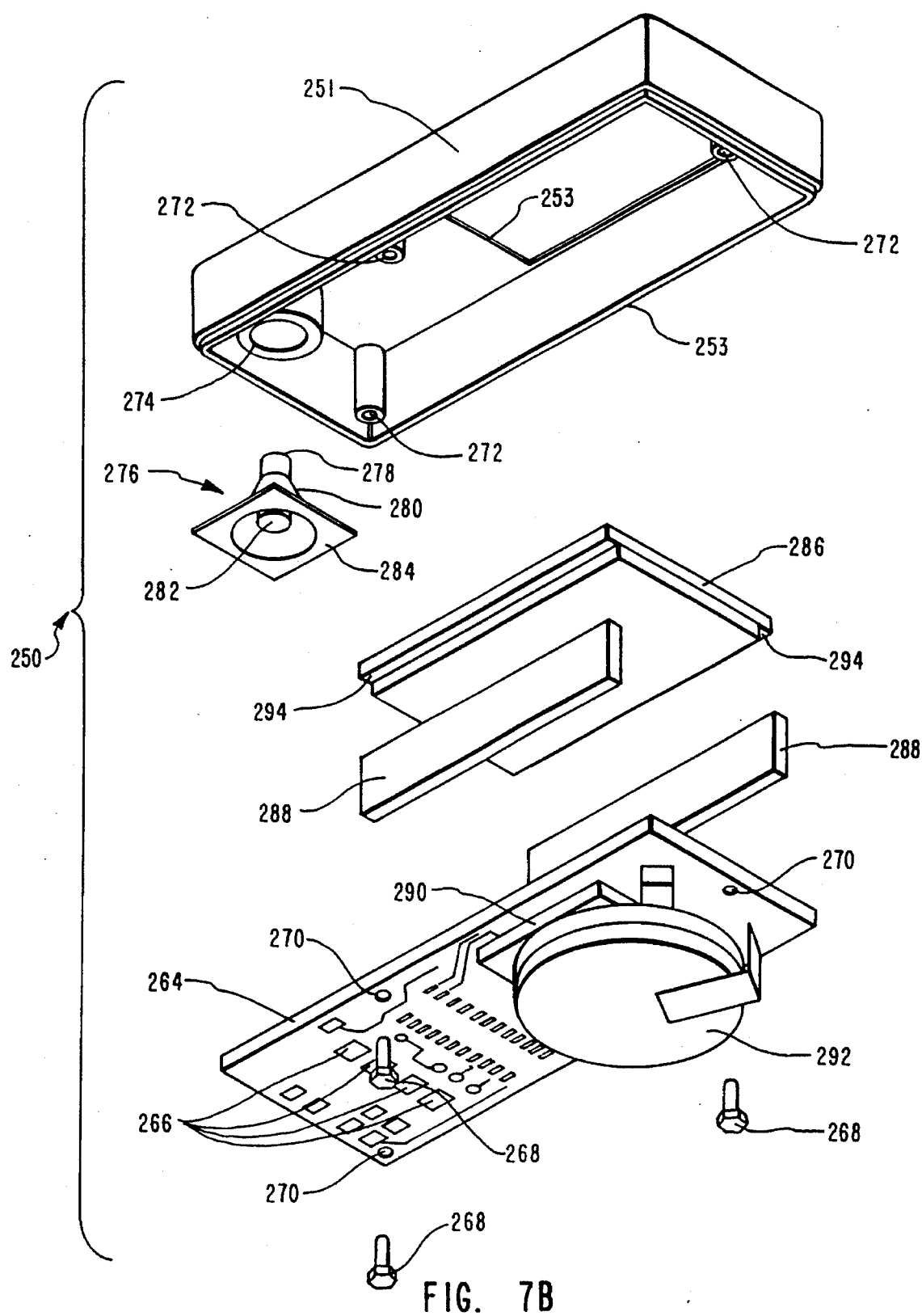
FIG. 7B is an exploded perspective illustration which shows in greater detail some of the primary components and assembly constituting the electronic controller for the embodiment of the syringe system illustrated in FIG. 7.
Figure 8:
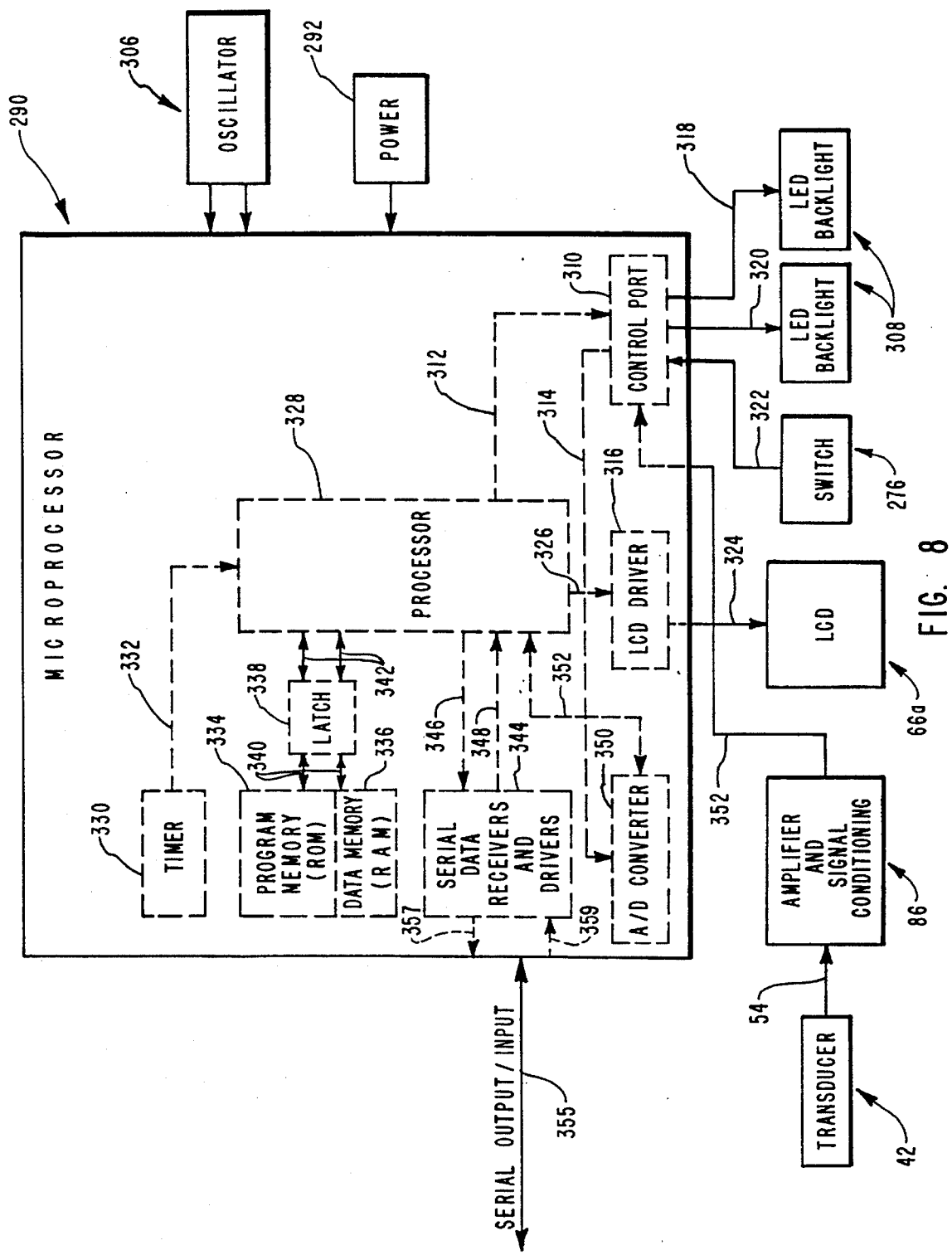
FIG. 8 is a functional block diagram which schematically illustrates the primary components of the digitally controlled electronic circuit used in connection with the syringe system of FIG. 7.

FIG. 7 illustrates an alternative embodiment of the syringe system of the present invention. In the embodiment of FIG. 7, the electronic circuit means and display means of the system of the present invention are designed so as to comprise part of a miniaturized controller, which is generally designated at 20a, that is battery powered and is mounted directly onto the syringe 16 so as to form a totally self-contained, disposable syringe system 14a. The specific electronic circuitry which is used for implementing the controller 20a, and its method of use for monitoring, displaying and recording PTCA data as illustrated in FIGS. 7–10 is set forth in U.S. Pat. No. 5,201,753, which is incorporated herein by reference, in its entirety.

3. FIGS. 11–13.

Figure 11:
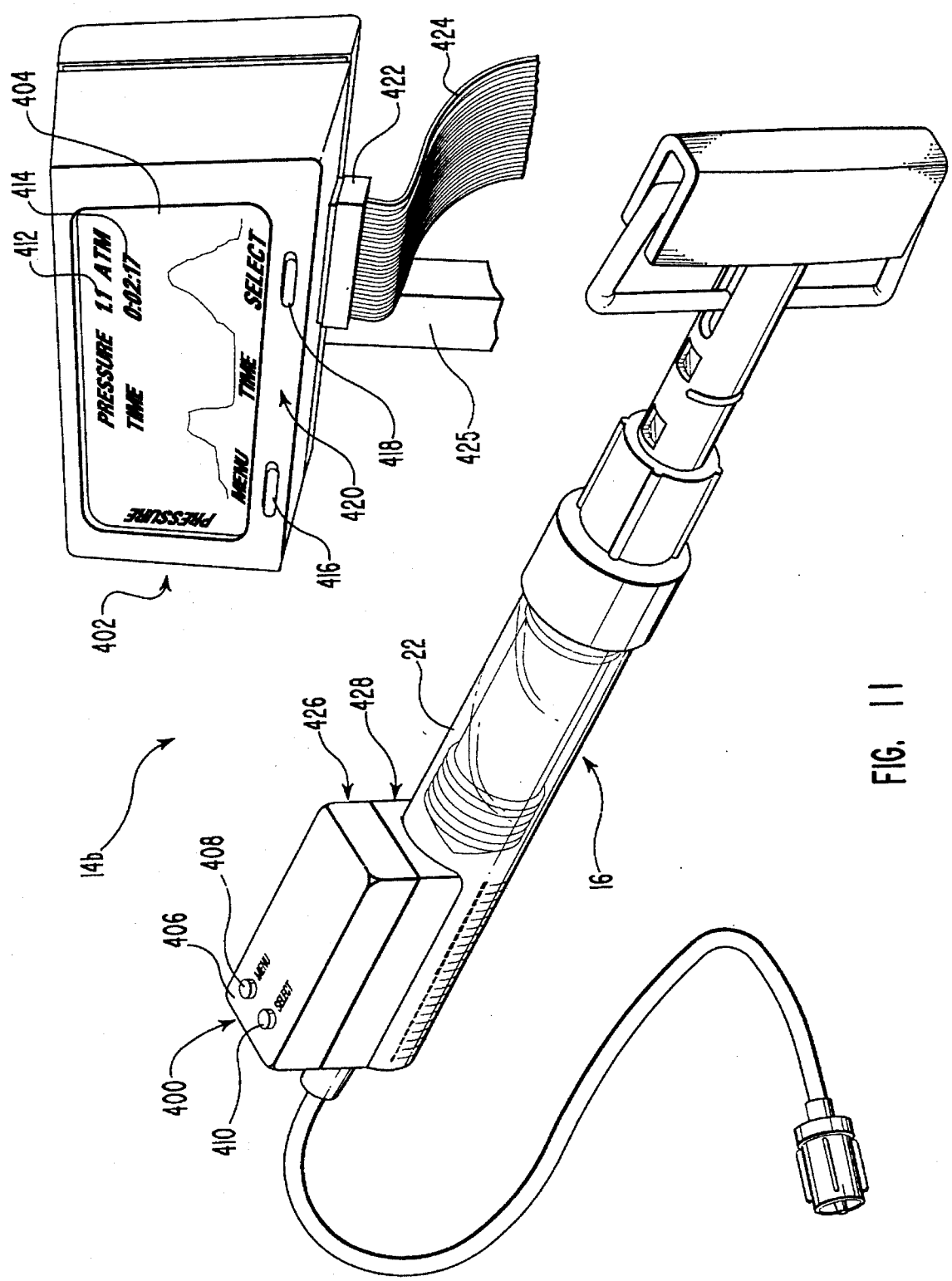
FIG. 11 is a perspective illustration showing yet another embodiment of the system of the present invention in which a RF transmission module is mounted to the syringe barrel.

FIG. 11 illustrates yet another alternative embodiment of the present invention that utilizes an RF transmission means to wirelessly transmit inflation data from the inflation syringe to a remote console means, where the data is then further processed, displayed and/or recorded. As is shown, the syringe system of this embodiment, designated generally at 14b, includes a syringe, generally designated at 16, that is essentially identical in all respects to the syringe 16 described above in connection with FIGS. 2 and 3 and therefore will not be described in further detail here. Syringe system 14b also includes a transducer means, as for example a piezoresistive semiconductor transducer 42 (described in connection with FIG. 11A below), for sensing a fluid pressure and for outputting an electrical pressure signal proportional to the sensed fluid pressure.

As is further illustrated in FIG. 11, the syringe system 14b includes an RF transmission means, as for example an RF transmission module 400 mounted to the syringe 16, for receiving the electrical pressure signal and for wirelessly transmitting transmission data that is representative of the electrical pressure signal via a selected radio frequency signal. Preferably, the RF transmission module 400 is permanently mounted to the end of the syringe barrel 22. FIG. 11 further illustrates how the syringe system 14b includes a remote console means, as for example remote console 402, that is positioned away from the syringe 16 and its attached RF transmission module 400. As will be discussed in further detail, the remote console 402 is capable of wirelessly receiving the transmission data that is transmitted by the RF transmission module 400, and is further capable of electronically processing the transmission data so as to derive and so as to display or record therefrom digital inflation or deflation data that is representative of the magnitude of the fluid pressure applied to the balloon member as well as the length of time the fluid pressure is applied to the balloon member. The syringe system 14b also includes a display means, such as graphics display 404, that is electrically connected to, and preferably formed as an integral part of, the remote console 402. The graphics display 404 is capable of outputting a visual display of the digital inflation or deflation data derived by the remote console 402.

As will be described in further detail below, the RF transmission module 400 has a control panel 406 that is equipped with a switch means for selectively controlling the remote console 402 to perform at least one of a plurality of optionally selectable functions. Preferably, the switch means is comprised of a first switch means, as for example menu switch 408, and a second switch means, as for example select switch 410. The menu switch 408 allows the syringe system 14b user to select a menu display for presentation on the graphics display 404. This menu display has a plurality of optionally selectable functions that can be performed by the remote console 402. The user can then operate the select switch 410 so as to enter to the remote console 402 data that identifies which of the optionally selectable functions is to be performed by the remote console 402. Thus, the RF transmission module 400 allows the system user to selectively monitor the data that corresponds to the inflation or deflation of the balloon catheter and to selectively record and display historical data corresponding to past inflations—by selectively operating the switches on the control panel 406.

Advantageously, the RF transmission module 400 is conveniently positioned on the syringe 16 so as to allow the user to control the remote console 402 and view inflation data while, at the same time operating the syringe 16. Further, the RF transmission module 400 provides the user with a greater level of freedom in how the syringe can be handled and positioned during an inflation procedure because there is no need for any bulky cable connections between the syringe and the remote console 402. Similarly, there is no need to sterilize (or maintain the sterility of) a cable and/or cable connectors that would otherwise be used to interconnect the syringe 16 and the remote console 402.

With continued reference to FIG. 11, the graphics display 404 is illustrated as being integrated in the remote console 402. Remote console 402 can be located on a stand 425 or similar device, and be positioned at any point where it can be seen by the cardiologist or clinician using the inflation syringe 16. The remote console 402 can be switched on or off using a conventional switch located on the console (not shown). For power, the remote console 402 is plugged into a conventional AC wall outlet, and as will be discussed further, the remote console 402 is also equipped with a battery-backed memory which provides an internal clock and timer and which retains data in memory after the remote console 402 is switched off. The specific electronic circuitry which is used for purposes of receiving transmission data sent by the RF transmission module 400, and for processing the transmission data, is contained within the remote console 402 and is more particularly illustrated in FIG. 13, which is described in further detail below.

As FIG. 11 further denotes, the display means is preferably comprised of a type of graphic display 404 that is capable of displaying, in an easy to read format, pressure information 412, and time information 414. The pressure portion 412 of the display is also used for purposes of inputting selected control data, such as maximum positive pressure desired in connection with an inflation, and selection of pressure units. Similarly, the time portion 414 of the display is also used for inputting selected control data such as the maximum duration for an applied positive pressure.

As noted above, the remote console 402 and display 404, and the information displayed thereon, is controlled via the selective operation of the menu and select switches 408, 410 disposed on the RF transmission module 400. Preferably, a second menu switch 416 and a second select switch 418 are disposed on a second control panel designated generally at 420, that is positioned on the front panel portion of the remote console 402. These switches 416, 418 operate identically to the corresponding switches 408, 410 that are disposed on the RF transmission module 400, and any function performed by the switches 408, 410 will also apply to switches 416, 418. In this way, the remote console 402 may be optionally controlled by a user via the second control panel 420.

It will be appreciated that the display 404 may be configured in a variety of ways so as to display the information generated by the remote console 402. For instance, time and pressure information may optionally be displayed graphically and/or alphanumerically. Also, as is further illustrated in FIG. 11, remote console 402 is equipped with a conventional connector 422 for a printer cable 424 so that data which is recorded by the remote console 402 can be selectively (via the menu and select switches 408, 410) printed out for permanent documentation and later reference.

As is further shown in FIG. 11, the RF transmission module 400 is preferably permanently mounted to the syringe barrel 22. The transmission module 400 is comprised of an upper housing assembly, generally designated at 426, and a lower housing assembly, generally designated at 428. Upper housing assembly 426 and lower housing assembly 428 are joined together, with the lower housing being mounted directly to the end of the syringe barrel 22.

Figure 11A:
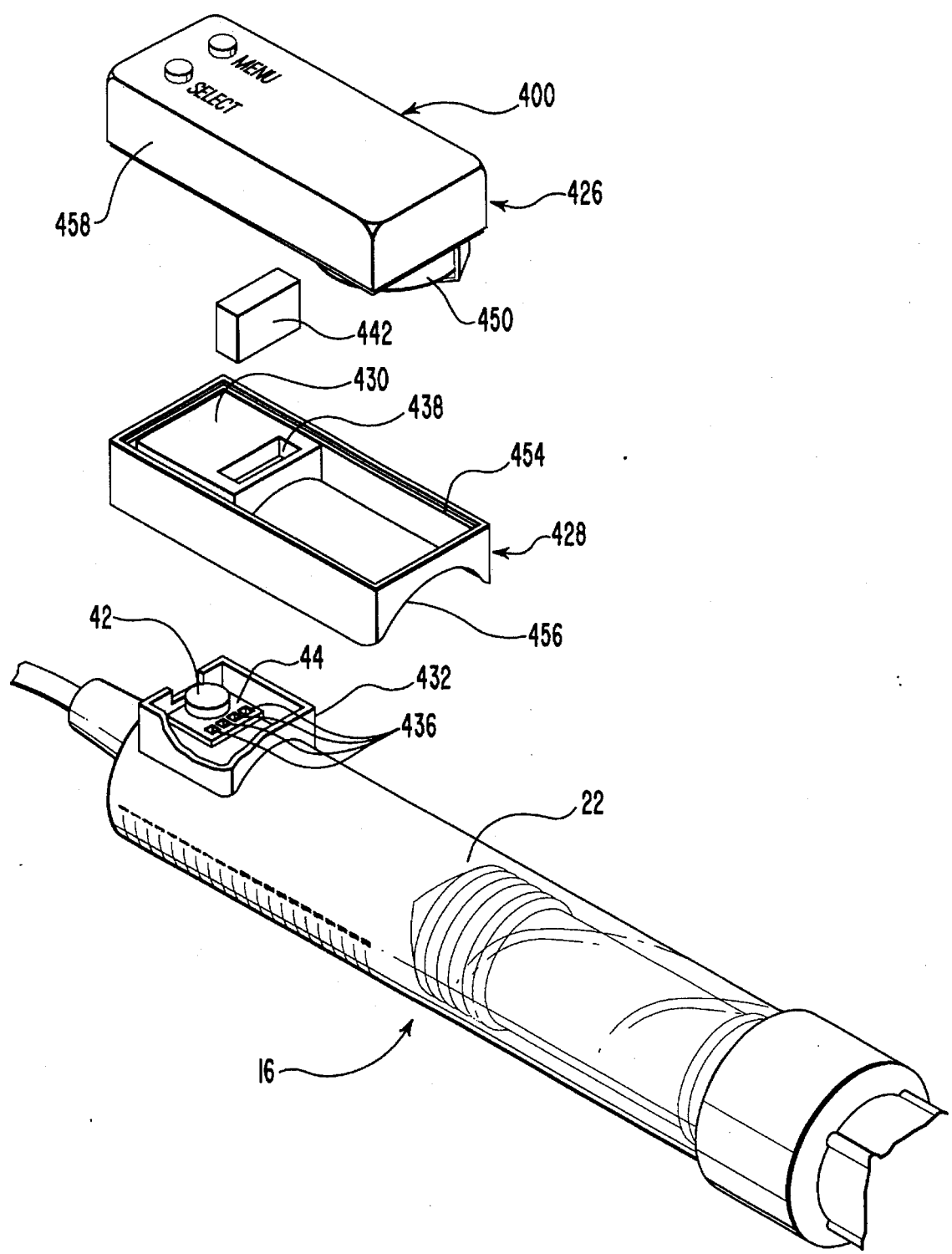
FIG. 11a is a perspective illustration of a portion of the syringe system of FIG. 11, with portions of the RF transmission module shown in exploded perspective to more particularly illustrate certain details thereof.
Figure 11B:
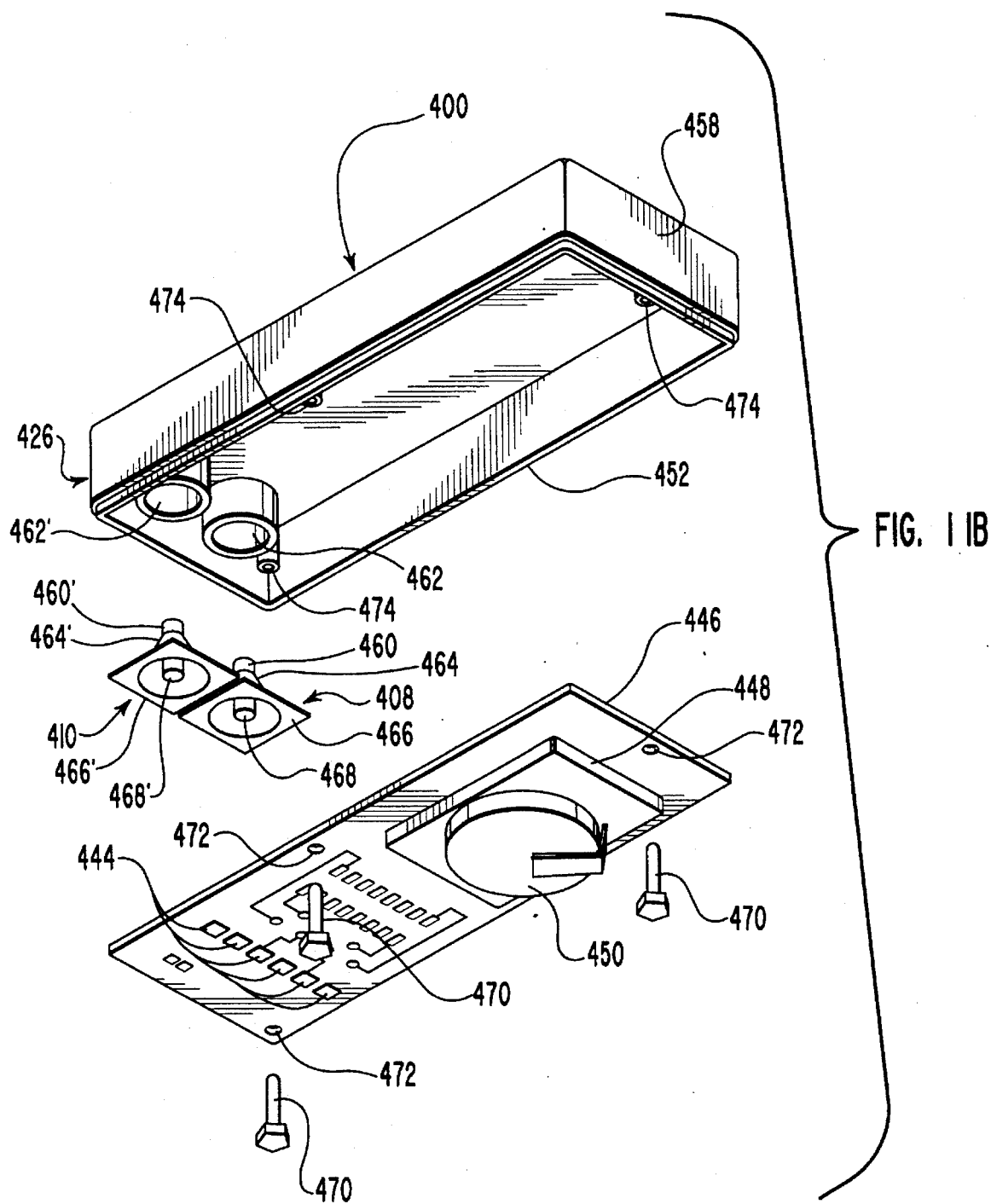
FIG. 11b is an exploded perspective illustration which shows in greater detail some of the primary components and assembly constituting the RF transmission module of the embodiment in FIG. 11.

The manner in which the RF transmission module 400 is constructed and mounted to the syringe barrel 22 is more particularly illustrated in FIGS. 11A and 11B, taken together. As is shown in FIG. 11A, the lower housing assembly generally designated at 428 is preferably formed as a single molded plastic part. The lower housing assembly 428 is formed with a generally square shaped box portion 430 which is designed to dimensionally fit over the correspondingly shaped transducer housing 432 which is molded as part of the syringe barrel 22.

As in the case of the embodiment illustrated in FIGS. 2 and 3, the integrated circuit which includes the transducer 42 is mounted directedly onto a ceramic substrate 44 and is electrically connected to conductive pads 436. A rectangular opening 438 is provided in the square shaped member 430 which fits over the correspondingly shaped transducer housing 432. The rectangular opening 438 in turn is intended to receive a conductive elastomeric or rubber member 442 such that when the member 442 is seated within the rectangular opening 438, the bottom of member 442 will contact the conductive pads 436. The conductive rubber member 442 is comprised of a material that is known in the art as a "zebra" or "Z" strip. Accordingly, the conductive rubber Z strip 442 serves as a means for providing an electrical interconnection between ceramic substrate 44 onto which the transducer 42 is mounted, and the other electronic components of the RF transmission module 400 which are carried on the printed circuit board 446. More particularly, the conductive rubber member 442 contacts and provides electrical interconnection between the conductive pads 436 on the ceramic substrate 44 and the corresponding conductive pads 444 that are provided on one side of the printed circuit board 446 (shown in FIG. 11B).

Referring now to FIG. 11B, it is shown how the upper housing assembly 426 of RF transmission module 400 carries the printed circuit board 446 onto which is mounted the microprocessor circuit 448, a battery 450, and other electronic components which are required for the circuitry of the RF transmission module 400, as illustrated and described in more detail in connection with FIG. 12. Power means, such as a battery 450, provides electrical power to the transducer 42 and the electronics contained within the RF transmission module 400.

The upper housing assembly 426 comprises a generally rectangular shaped molded piece 458 that is provided with a rim 452 that extends around its entire bottom periphery and, which is designed to fit into a corresponding channel 454 which is formed around the upper periphery of the lower housing assembly 428 (shown in FIG. 11A). The two housing assemblies 426 and 428 can be firmly bonded together and the entire RF transmission module assembly 400 is then permanently mounted and bonded onto the syringe barrel 22 (as is illustrated in FIG. 11). For this purpose, the lower housing assembly 428 is provided with a corresponding cylindrical shape 456 (best seen in FIG. 11A) on its underside so that the lower housing assembly 428 conforms to the cylindrical shape of the syringe barrel 22. Preferably, the upper housing assembly 426 and the lower housing assembly 428 are both molded from an opaque plastic material.

As discussed above, the RF transmission module 400 is preferably comprised with a menu switch 408 and a select switch 410 (shown in FIGS. 11 and 11A). FIG. 11B illustrates how the menu and select switches 408, 410 are each preferably comprised, for example, as elastomeric button switches. Thus, menu switch 408 has an upper cylindrical extension 460 that extends through an opening in well 462 which is formed in the upper rectangular member 458 so that the cylindrical portion 460 can be finger-actuated by pressing. The menu switch 408 also is comprised of a means for preventing entry of liquids at the switch 408, as for example an integral conically shaped skirt 464 which terminates in a generally square shaped base 466. Base 466 entirely covers the base of well 462 so that when the entire assembly is completed, the switch 408 is fluid tight and will thus not permit water, saline solution or other liquids to enter the RF transmission module 400 through the location of the actuable button 460. Accordingly, the base 466 extends downwardly and rests again on the upper side of the printed circuit board 446 so that the actuable button 460 is held in a position which extends through the opening of well 462 into the position as shown in FIG. 11A but at the same time the base 466 also seals the well 462. When the button 460 is pushed downwardly, the circular base 468 of the button switch 460 is pushed into contact with the conductive pad (not shown) on the upper side of the printed circuit board 446 thereby making the necessary electrical contact to activate the electronic components, as hereinafter more fully described. The elastomeric properties of conical skirt 464 will return the button 460 upwardly when it is released. Note that the select switch 410 is preferably constructed in a similar manner, and like parts are signified with like numbers having a prime sign.

The microprocessor circuit 448 is mounted to the underside of printed circuit board 446 and a battery 450 is mounted over the microprocessor 448 on the same side of the printed circuit board 446. In the preferred assembly of the upper housing assembly 426, the elastomeric button switch 460, 460' portions of the menu and select switches 408, 410 are placed into the wells 462, 462' and then the printed circuit board 446 is placed over the square base portions 466, 466'. Pins or anchors 470 are then inserted through corresponding holes 472 in the printed circuit board 446 and into corresponding receiving holes 474 in the top portion of the upper housing assembly 426. The pins 470 are bonded or otherwise anchored into the holes 474 such as by a press fit, threaded fit, or other appropriate means.

Figure 12:
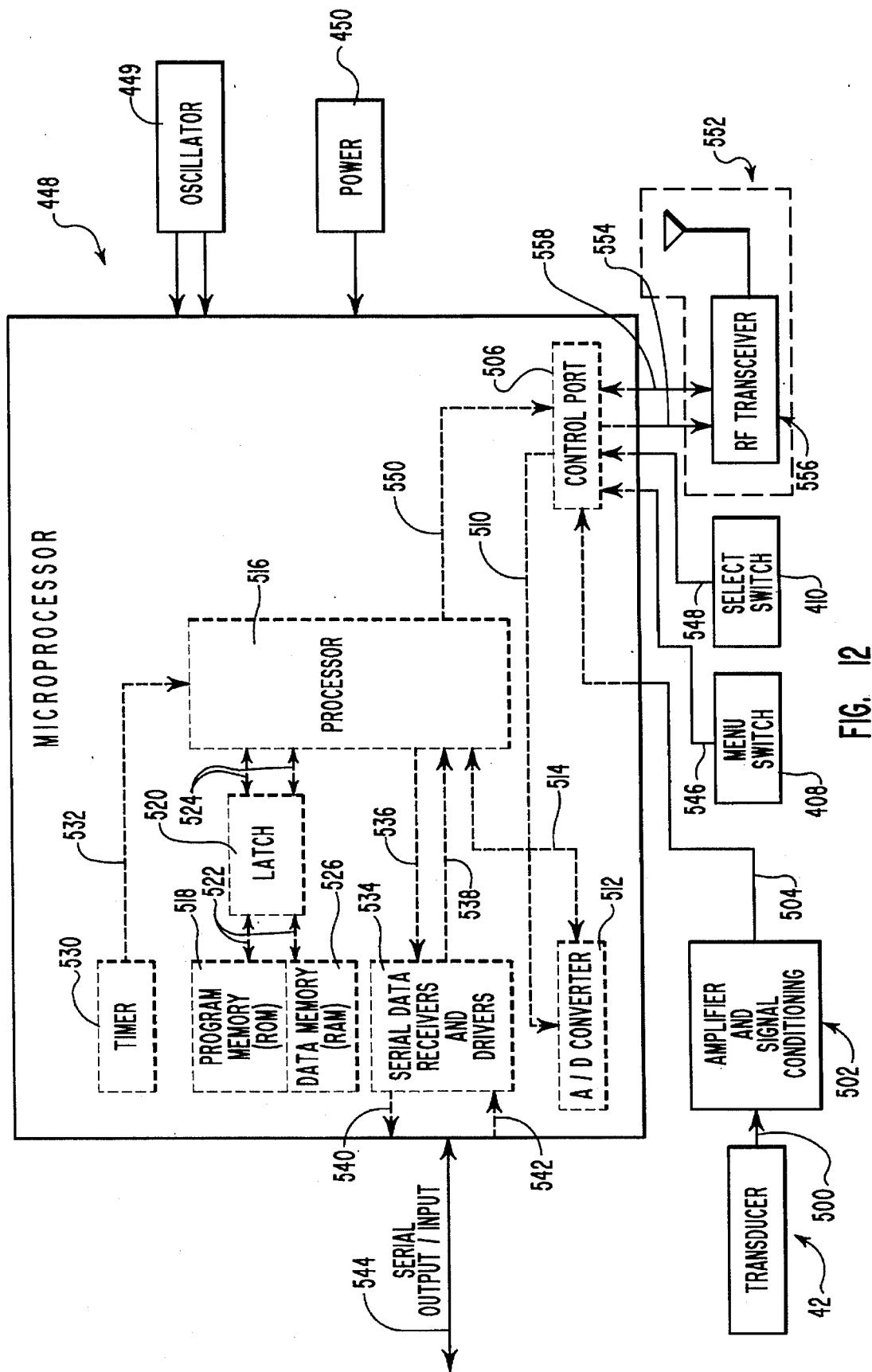
FIG. 12 is a functional block diagram which schematically illustrates the primary components of one presently preferred embodiment of the electronic circuit used in connection with the RF transmission module shown in FIG. 11.

The electronic circuitry which comprises the RF transmission module 400 is illustrated in further detail in the functional block diagram of FIG. 12. The RF transmission module 400 comprises, by way of example, means for amplifying and conditioning the electrical pressure signal output by the transducer 42; means for converting the amplified pressure signal from an analog to a digital form; digital processor means for processing the digital form of the electrical pressure signal so as to derive therefrom transmission data; data memory means for storing the transmission data derived by the digital processor means; program memory means for storing machine-readable instructions utilized by the digital processor means to derive and store the transmission data for transmission; and RF transmission circuit means for wirelessly transmitting the transmission data as an RF signal having a predetermined radio frequency.

With continued referenced to FIG. 12, the transducer 42 is essentially the same as the transducer previously described in connection with the embodiment of FIGS. 2–5. Transducer 42 is electrically connected as schematically shown at 500 (by means of the conductive rubber Z strip 442 described above) to the circuit components which serve as the amplifier and signal conditioning circuitry as generally designated at 502 in FIG. 12. The presently preferred embodiment of the amplifier and signal conditioning circuit 502, and the oscillator 449 and power circuit 450 are essentially identical to the corresponding circuits contained in the functional block diagram of FIG. 8, and the accompanying electrical schematic diagram of FIGS. 5B and 9B (and more particularly, the circuit enclosed by dashed box 86 in FIGS. 5B and 9B). The detailed description directed to those circuits will not be repeated here.

From the amplifier and signal conditioning circuit 502 the amplified analog electrical pressure signal is then input as schematically represented at line 504 to a control port 506 which is internal to the microprocessor's 448 integrated circuitry. From control port 506 the signal is input as schematically indicated at line 510 to an analog to digital (A/D) convertor 512 which is also internal to the microprocessor's integrated circuitry. The A/D convertor 512 serves as a means for converting the amplified signal from the analog to a digital form.

The particular integrated circuit which is used for microprocessor 448 is the same as microprocessor 290 identified above in FIG. 9A as integrated circuit U1 and which is also further identified in Table II at the end of the detailed description. It should be appreciated that the particular circuit components and circuit design are intended merely as an example of the presently preferred embodiment and the presently understood best mode of implementing the overall functions which are represented by the block diagram of FIG. 12. Of course other circuit designs could be devised that would work satisfactorily, using either software-based digital processing circuitry or hardware-based circuit designs.

With continued reference to FIG. 12 the digitized signal is input as schematically indicated at line 514 to the digital processor 516. The digital processor 516 is controlled by the programmed instructions stored in program memory (ROM) 518 and which are communicated as schematically illustrated at lines 522 through a latch 520 to the digital processor 516. The particular program instructions carried out by the digital processor 516 are more particularly illustrated and described in reference to the flow chart of FIGS. 14A and 14B, as hereinafter more fully described in Section II. The program instructions are addressed by the digital processor 516, as schematically represented by the lines 524 through latch 520.

Briefly summarized, the instructions stored in program memory 518 are utilized by the digital processor 516 to derive from the digitized transducer signal transmission data which represents the applied inflation pressure which is being exerted by the syringe 16 on the balloon of the catheter. This is designed to occur in real time as the pressures are being applied. At the same time, the duration of the applied inflation pressure is timed, and transmission data representative of the duration is generated. The digital processor 516 then causes the transmission data, representative of pressure and time magnitudes and other control and status information (discussed below in connection with FIGS. 14A and 14B), to be transmitted wirelessly via an RF transmission signal to the remote console 402.

The data memory means of the RF transmission module 400 is provided, in the embodiment of FIG. 12, by a scratch pad random access memory (RAM) 526 which is also accessed through latch 520 by digital processor 516. The digital data memory 526 is used to record and store the various transmission data derived from the electrical pressure signal. The transmission data is queued in memory 526 so as to assemble data packets which are subsequently transmitted as transmission data to the remote console 402.

A timer 530 also communicates as schematically indicated by line 532 with the digital processor 516, and is internal to the integrated circuitry contained on the microprocessor circuit 448. Serial data receivers and drivers 534 also communicate as schematically illustrated at lines 536 and 538 with the digital processor 516, and are internal to the integrated circuitry of the microprocessor 440. The serial data receivers and drivers 534 can be used for outputting a variety of data through a serial communication output/input line as schematically indicated at lines 540, 542 and 544.

The microprocessor circuit 448 monitors the status of the menu switch 408 and the select switch 410 via the control port 506, as is schematically illustrated at lines 546 and 548. In this manner, the microprocessor 448 can detect when a user has depressed either of the switches 408, 410 and then transmit that status information to the remote console 402 via a transmission data packet. As discussed generally, the functions associated with the menu and select switches 408, 410 allow the user to control the operation of the remote console 402, which is described in further detail below in connection with FIG. 13.

The microprocessor 448 is programmed to output pressure and time values, the status of the menu and select switches 408, 410, and other control and status information to the control port 506, as is schematically illustrated at line 550. This transmission data is then sent to the RF transmission circuit means, as for example circuitry that is schematically illustrated within the dotted box 552, via line 554. The circuitry contained within box 552 takes the transmission data and transmits it to the remote console 402 via an RF signal.

In the present best mode of the invention, the RF transmission circuit means is comprised of RF transceiver circuitry 556 capable of implementing the EIA CEBus (IS-60) Radio Frequency (RF) physical layer utilizing a spread spectrum technology which conforms with Federal Communications Commission Part 15 rules. Preferably, the RF transceiver circuitry 556 is comprised of a Spread Spectrum Carrier™ RF Transceiver integrated circuit having the tradename of CELinx rf, which is manufactured and sold by Intellon Corporation of Ocala, Fla. This Spread Spectrum Carrier™ circuit, covered in U.S. Pat. No. 5,090,024, is based on a direct sequence method of spreading the digital data into a broad spectrum or band. Each bit of the digital signal is spread into a unit symbol using a forward or reverse sequence of seven substrates each consisting of a 360 bit chipping sequence. The bit chipping sequence approximates a forward or reverse frequency sweep from 4.2 to 6.3 Megahertz. This sequence is further modified by a 15-bit phase modulation function. The combined effect of the 360 bit chipping sequence, the 7 substate sequence and the 15-bit phase modulation function is an even spreading of the digital information across a 2.1 Megahertz band. The use of a spread spectrum method allows the system to benefit from increased signal gain inherent in processing the signal using spreading and despreading algorithms to encode the transmitted signal. This processing gain allows the system reliability to increase without increasing the power output from the transmitter.

Thus, referring to FIG. 12, the microprocessor circuit 448 encodes and formats the transmission data and then passes the transmission data to the RF transceiver module 556 via line 554. Microprocessor circuit 448 also monitors and controls the operation of the RF transceiver module 556, as is schematically shown at line 558. RF transceiver module 556, under the control of microprocessor circuit 448, will then transmit the transmission data to the remote console 402 via the predetermined radio frequency, as discussed above.

With a continued reference to FIG. 12, power for the microprocessor 448 and other circuit components is supplied by the battery 450 which is also illustrated in connection with the upper housing assembly 426 of FIG. 11B. The battery 450 permits elimination of any connecting cables or the like so that the syringe system 14b is totally self-contained and does not require outside connection to any other power source. This advantageously simplifies the overall system 14b and makes maintaining sterility of the syringe system 14b an easier task throughout the entire procedure.

Figure 13:
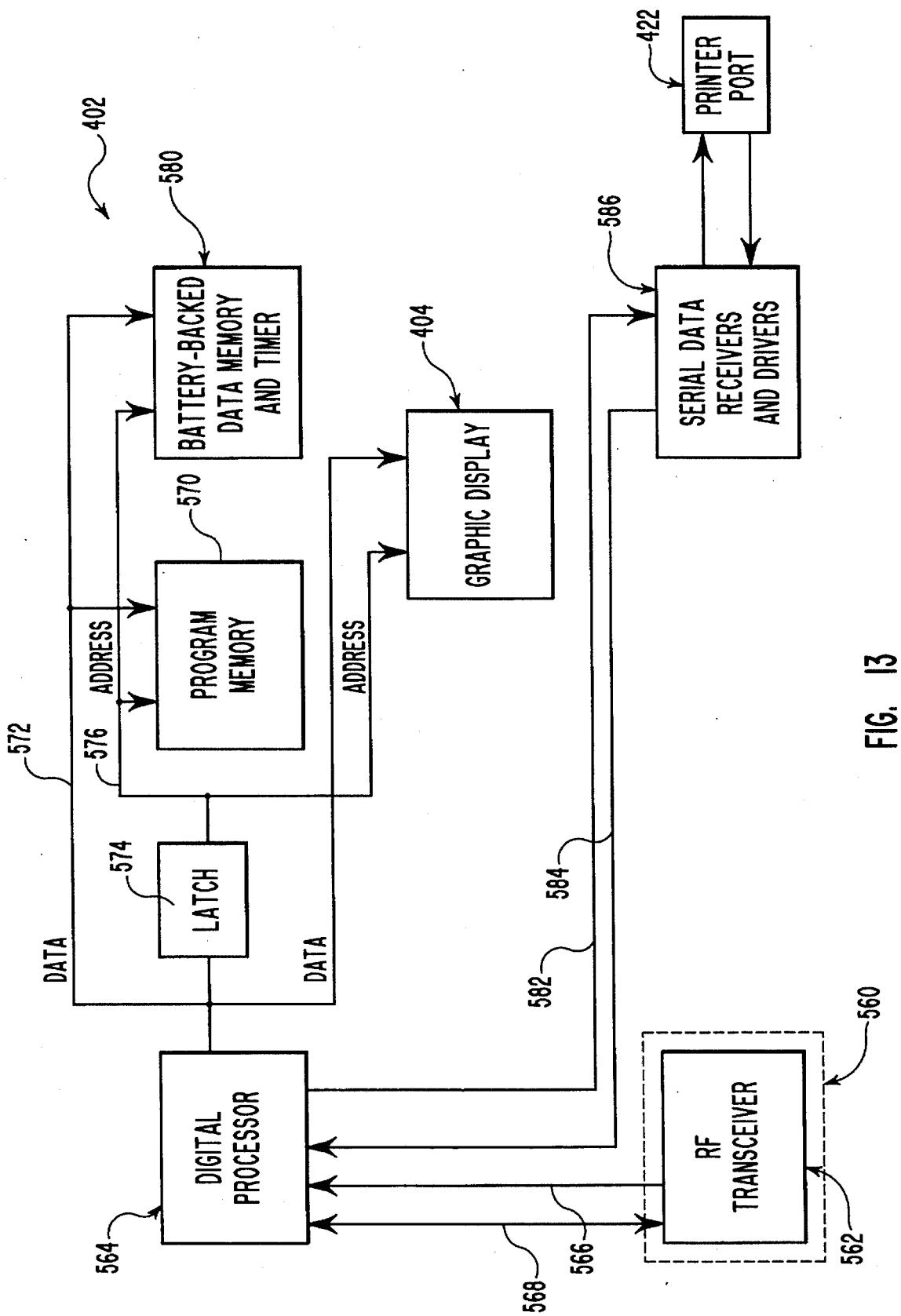
FIG. 13 is a functional block diagram which schematically illustrates the primary components of one presently preferred electronic circuit used in connection with the remote console shown in FIG. 11.

With reference next to FIG. 13, the electronic circuitry of the remote console 402 is more particularly illustrated in block diagram form. In the presently preferred embodiment, the remote console 402 comprises, by way of example, RF receiver circuit means for receiving the transmission data transmitted by the RF transmission module; second digital processor means for monitoring the transmission data transmitted by the RF transmission module 400 and for processing the received transmission data so as to derive, store and display digital inflation or deflation data which represents the magnitude of the applied pressure and the duration of time the pressure is applied to the member; second data memory means for storing the digital inflation or deflation data derived by the second digital processor means; and second program memory means for storing machine-readable instructions utilized by the second digital processor means to monitor the transmission data and to derive, store, retrieve and display the digital inflation or deflation data.

With particular reference to the presently preferred embodiment of the remote console 402 in FIG. 13, the RF receiver circuit means is comprised of RF receiver circuitry contained within the dotted box generally designated at 560. The RF receiver circuitry is capable of receiving a signal that is transmitted by the RF transmission circuitry 556 of the RF transmission module 400, and thus is capable of implementing the EIA CEBus (IS-60) Radio Frequency (RF) physical layer utilizing a spread spectrum technology conforming with the FCC Part 15 rules. Preferably, the RF receiving circuitry is comprised of the same CELinx rf transceiver 556 manufactured by Intellon Corporation previously described. The RF receiver circuit 562 receives the transmission data, demodulates the transmission data, and then passes the transmission data to second digital processor 564, via line 566. The digital processor 564, in addition to accepting the received transmission data, also monitors and controls the RF receiver circuit 562, as is shown at line 568.

The second digital processor 564 is controlled by machine-readable instructions stored in second program memory means, as for example program memory 570, which are communicated by a data bus, schematically illustrated as 572, running between digital processor 564 and program memory 570. The particular program instructions carried out by the digital processor are more particularly illustrated and described in reference to the flow chart of FIGS. 15A–15J which will be described in greater detail below in Section II. The program instructions are addressed by the digital processor 564 through latch circuit 574 and the address bus represented at line 576.

Briefly summarized, the instructions stored in program memory 570 are utilized by the second digital processor 564 to derive from the transmission data transmitted from the RF transmission module 400 the fluid pressures applied by the syringe 16 to the balloon catheter and to display the sensed pressures, and the durations of the pressure, on the graphic display 404. The applied fluid pressures are also automatically recorded by second digital processor 564 and stored in the second data memory means, as for example the battery-backed data memory and timer 580. The output of the digital data to the graphic display 404 is transmitted by way of a data bus which is used to drive the graphic display 404. The second digital processor 564 can also be programmed to display the positive inflation pressure which is output on the graphic display 404 in units of either atmospheres or pounds per square inch as selected by the system user by means of the menu and select switches that are disposed on the RF transmission module 400 (408, 410) or on the remote console 402 (416, 418).

Second digital processor 564 can also be utilized, according to the programmed instructions contained in program memory 570, to monitor and thus assist in the control of the maximum positive inflation pressure to be applied to the balloon catheter by inputting on the graphic display 404 a maximum positive pressure using the menu and select switches 408, 410. Once the maximum positive inflation pressure is reached, the second digital processor 564 will cause a portion of the graphic display 404 to flash, thereby signaling the system user that the maximum positive inflation pressure has been reached. This advantageously assists the system user in more carefully controlling and identifying the procedure used with respect to each inflation event.

In a similar manner, a selected duration for which positive inflation pressure is to be applied to the balloon catheter can also be input on the graphic display 404, again by using the menu and select switches 408, 410. Accordingly, the programmed instructions contained in program memory 570 will thereafter cause the second digital processor 564 to begin counting the duration once positive inflation pressure begins to be applied. The count will be output by processor 564 on the graphic display 404 which will flash once the selected duration has been reached, thereby signaling the system user that positive inflation pressure has been applied for the desired length of time. Again, this significantly enhances the ability of the overall system to carefully assist in controlling the inflation procedures according to the selected parameters.

Data memory 580 is battery-backed so as to retain all data stored therein even when the remote console 402 is switched off, and so as to provide an internal timer for the date and time data and for clocking any selected maximum duration times input as described above.

Each of the control parameters which are input on the graphic display 404 are input and stored in the data memory 580. In this manner, the appropriate control parameters are utilized by the program stored in the data memory 580 for later reference. In a similar manner, once a positive inflation pressure is applied, the second digital processor 564 will automatically time the duration of the positive pressures and this information will likewise be recorded and stored in the data memory 580 for later reference, along with a numerical identification input to the graphic display 404 which identifies whether the particular inflation event is the first time the balloon catheter has been inflated or whether the inflation is a subsequent inflation. In this manner, each time the balloon catheter is inflated it is discretely identified and the maximum inflation pressure and time duration data corresponding to that inflation event are not only displayed but are also automatically recorded and stored in the data memory 580.

With continued reference to FIG. 13, a latch circuit 574 is used to control the gating of address data from second digital processor 564 to the respective memories 570 and 580 and graphic display 404 as is conventional in the art.

In addition to the graphic display 404, the system of the present invention also provides for output of the recorded data from second digital processor 564 through serial data lines 582 and 584 to a serial data receiver and driver circuit 586, which in turn is connected to a printer port 422 to which printer cable 424 (shown in FIG. 11) is connected. Thus, inflation data from previous inflation events can be optionally printed for reference and later review.

Figure 4:
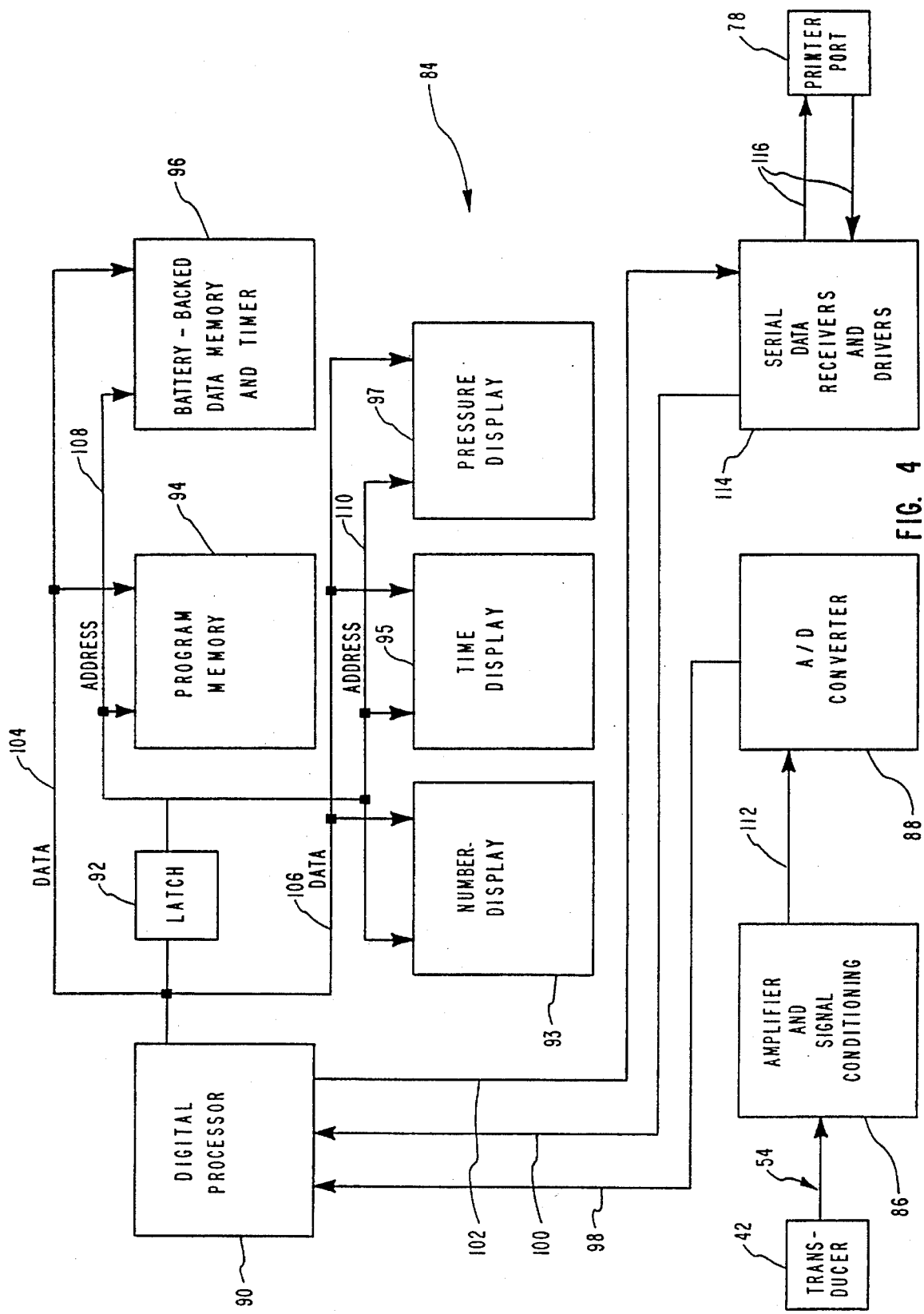
FIG. 4 is a functional block diagram which schematically illustrates the primary components of one presently preferred electronic circuit used in connection with the electronic controller.

The supply voltage used for driving the circuitry contained within the remote console 402 is supplied by means of a transformer (not shown) which is connected at its output to a full wave bridge rectifier (not shown) in a manner similar to that illustrated and described for controller 20 in FIG. 4.

II. The Method

Attention is next turned to a detailed description of the presently preferred methods by which the system of the present invention is used to monitor, display and automatically record inflation data, with particular reference to FIGS. 6A–6G and FIG. 10 which illustrate the presently preferred embodiments of the instructions which may be utilized to control the processor means 90 or 290, respectively. In another embodiment of the present invention, reference is made to FIGS. 14A through 14B, and FIGS. 15A through 15J, which illustrate the presently preferred embodiments of the instructions which may be utilized to control the digital processors 448 and 564 respectively. As will be appreciated by those of ordinary skill in the art, and as noted above, while the system and method as described in reference to the preferred embodiments herein illustrate the invention as implemented using state of the art digital processing design and corresponding program instructions, the system and method could also be implemented and carried out using a hardware design which accomplishes the necessary electronic processing, which is thus intended to be embraced within the scope of various of the claims as set forth hereinafter.

1. FIGS. 6A–6G.

The method by which controller 20 is programmed to carry out monitoring, display and recording of PTCA data as illustrated in FIGS. 6A through 6G is described in detail in U.S. Pat. No. 5,135,488, incorporated herein by reference in its entirety.

2. FIG. 10.

Figure 10:
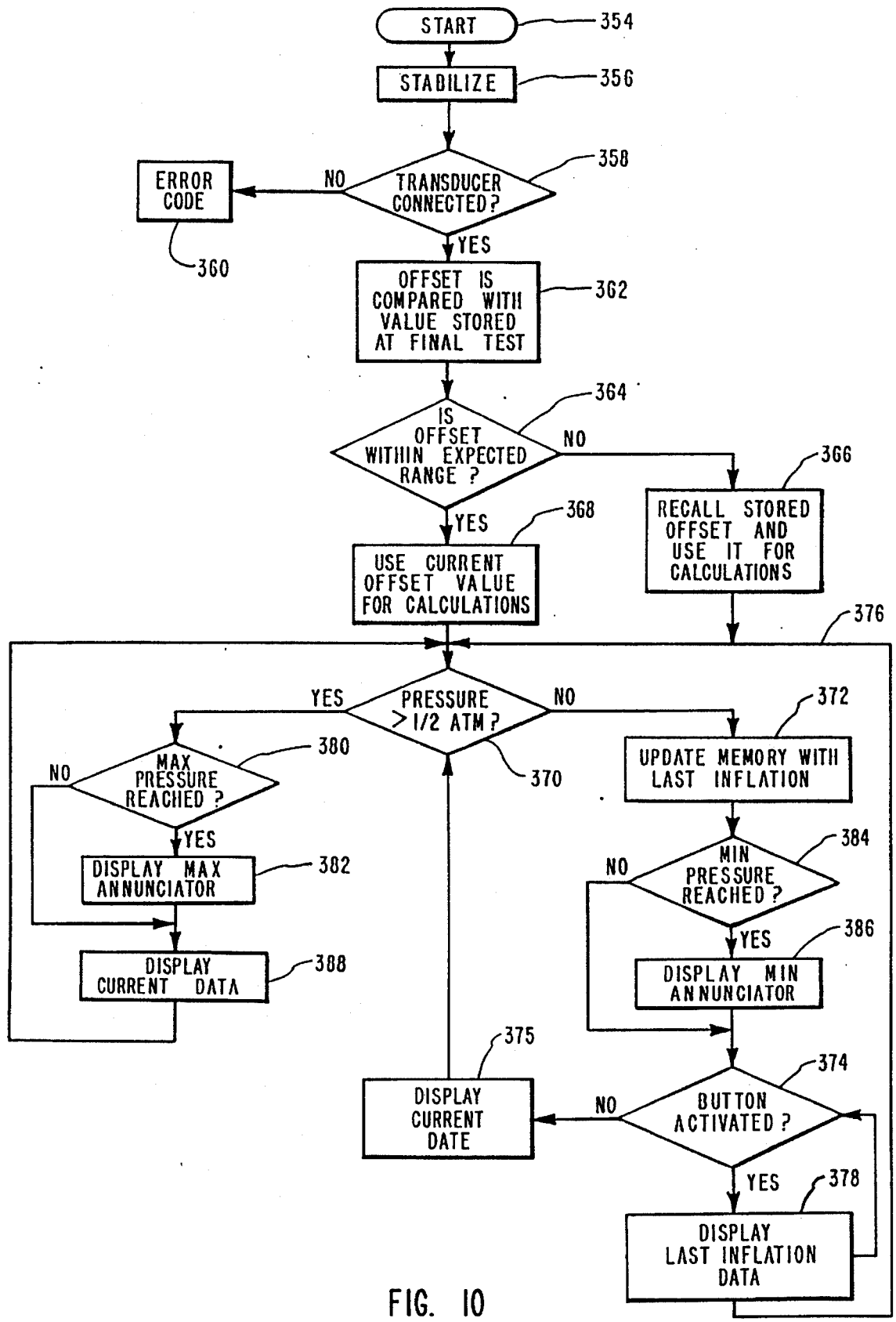
FIG. 10 illustrates a flow chart showing one presently preferred method for programming the digital processor of the electronic circuit means which is utilized for the syringe system in the embodiment of FIG. 7.

The method by which miniaturized controller 20a is programmed to carry out monitoring, display and recording of PTCA data as illustrated in FIG. 10 is described in detail in U.S. Pat. No. 5,201,753, incorporated herein by reference in its entirety.

3. FIGS. 14A–14B.

Figure 14A:
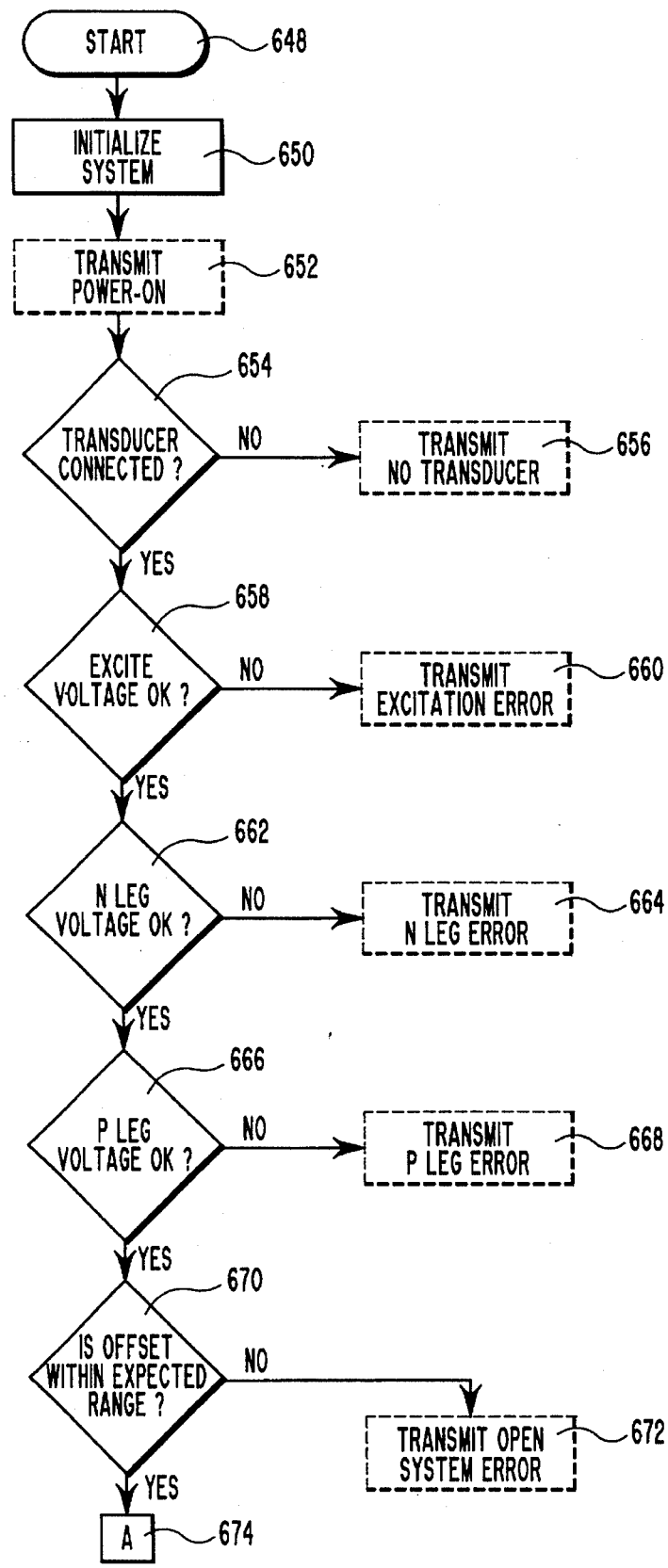
FIGS. 14a through 14b taken together illustrate a flow chart showing one presently preferred method for programming the digital processor of the RF transmission module shown in FIG. 11.
Figure 14B:
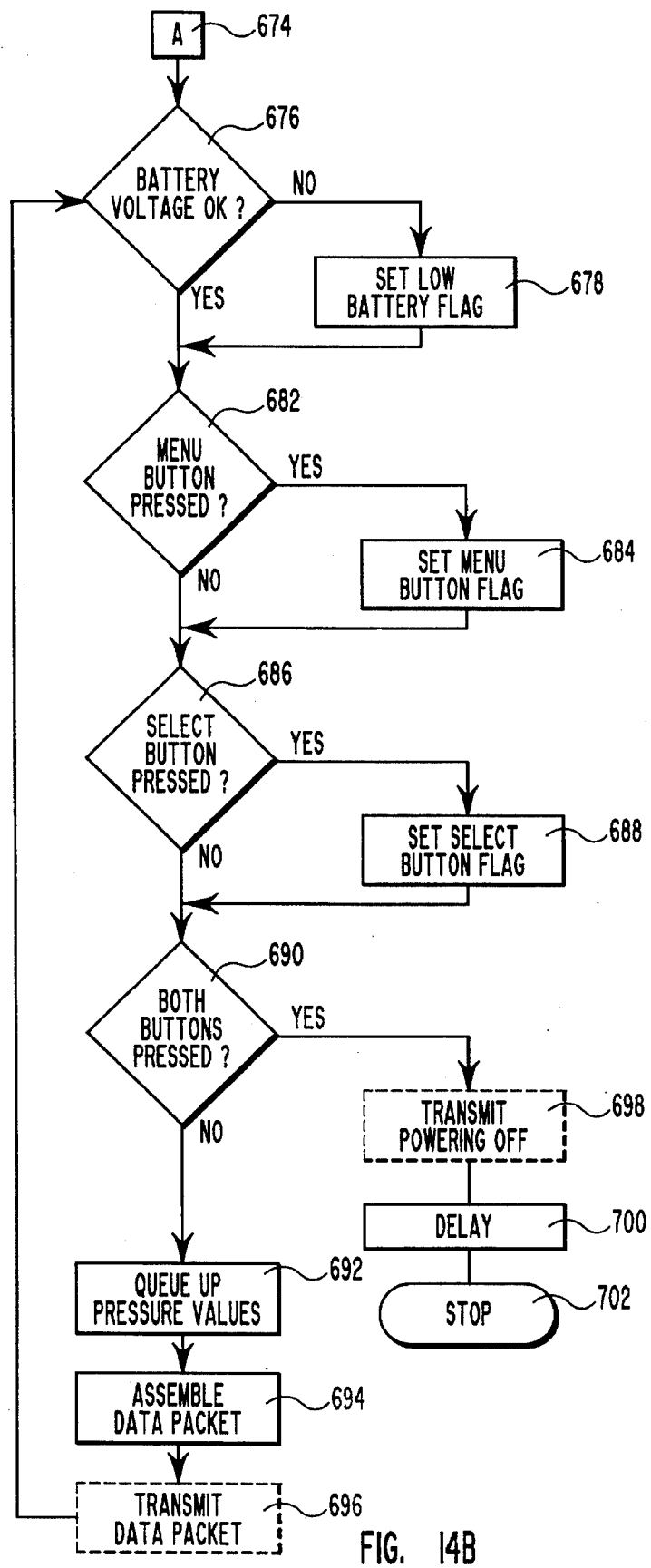

The embodiment of the program instructions as illustrated in the flow chart of FIGS. 14A and 14B is particularly designed for programming the microprocessor 448 described in connection with the RF transmission module 400 of the syringe system 14b previously discussed in conjunction with FIGS. 11 through 13.

Referring to FIG. 14A and starting at step 648, once menu switch 408 and select switch 410 are activated simultaneously the RF transmission module 400 is powered on. At step 650, the system is initialized and the appropriate program instructions are loaded into the microprocessor 448. The microprocessor 448 then moves to step 652 at which time a status flag indicating that the RF transmission module 400 has been powered on is transmitted as transmission data to the remote console 402.

The microprocessor 448 then performs a series of diagnostic steps so as to insure that both the RF transmission module 400 and the transducer 42 are properly interfaced and functioning correctly. At step 654, the microprocessor 448 checks to make certain that the transducer 42 is properly connected to the rest of the circuitry contained on the RF transmission module 400. If not, a status flag indicating "no transducer" is transmitted to the remote console 402 at step 656. If transducer 42 is properly connected, microprocessor 448 proceeds to step 658 and checks the excitation voltage of the transducer 42. If the excitation voltage is incorrect, a status flag indicating "excitation error" is transmitted to the remote console 402 at 660. If the excitation voltage is correct, the microprocessor 448 then proceeds to step 662 where the N-Leg voltage of the transducer 42 is checked. If incorrect, a status flag indicating "N-Leg error" is transmitted to the remote console 402 at 664. If N-Leg voltage is correct, microprocessor 448 proceeds to step 666 and checks the P-Leg voltage of the transducer 42. Again, if incorrect, a status flag indicating the error is transmitted to the remote console 402 at step 668. If correct, the microprocessor 448 proceeds to step 670.

At step 670, the microprocessor 448 determines the zero pressure reading of the transducer 42 and compares that value to a predetermined offset range. If the value falls outside of that range, a status flag indicating an "open system error" is transmitted to the remote console 402 at step 672. If the value falls within the range, the microprocessor 448 proceeds to step 676, shown on FIG. 14B. At step 676, the microprocessor 448 checks the battery 450 voltage level. If the voltage level is sufficient, the microprocessor 448 proceeds to step 680. If the voltage level is below a selected point, the microprocessor 448 warns the user by setting a "low battery status" flag at step 678, which will subsequently be transmitted to the remote console 402 as transmission data, before continuing to 680.

Having completed all of the diagnostic steps, the microprocessor 448 begins to monitor the electrical pressure signal generated by the transducer 42, which signal has been digitized and input to the microprocessor 448 as previously described in connection with FIG. 12. Thus, the microprocessor 448 proceeds to step 682.

This portion of the program instructions monitors the status of the switches (menu 408 and select 410) that are disposed on the control panel 406 of the RF transmission module 400. At step 682, the microprocessor 448 checks to see if the menu button 408 is being pressed by the user. If not, the processor proceeds directly to step 686. If menu button 408 is pressed, the processor 448 sets the "menu button" flag at step 684 and then proceeds to step 686. At step 686, microprocessor 448 determines whether the select button 410 is being pressed by the user. If not, the processor proceeds to step 690. If select button 410 is pressed, processor sets the "select button" flag at step 688 before proceeding to step 690.

At step 690 the microprocessor 448 determines if the menu button and select button 408, 410 are being pressed simultaneously. Pressing both buttons simultaneously causes the RF transmission module 400 to power off. In that case, the processor 448 proceeds to step 698 and transmits a "powering off" transmission data packet to the remote console 402. The processor 448 will then delay for a period of time, as is indicated at step 700, and will then halt and await a new power-on signal at step 702.

If both the menu and select buttons 408, 410 are not being simultaneously pressed, the processor 448 will proceed to step 692 and queue up the transmission data (i.e., pressure value, time value and/or status data). The processor 448 then, at step 694, assembles a data packet containing the transmission data, and proceeds to transmit the data packet at step 696 to the remote console 402. In the preferred embodiment, the data packet will include the current pressure value as well as pressure values from the previous two or three transmissions. This insures that pressure values are not inadvertently lost if, for instance, a particular transmission fails. After transmission, the processor 448 returns to step 676 and continues to process, as described above.

Thus, the RF transmission module 400 will, once it has powered on and run through a diagnostic procedure, continuously transmit transmission data to the remote console 402. This will continue until the user simultaneously presses the menu and select buttons 408, 410 and thereby powers off the RF transmission module 400.

4. FIGS. 15A–15F.

FIGS. 15A–15F illustrate the presently preferred embodiment of the instructions which may be utilized to control the second digital processor 564 contained within the remote console 402 discussed above in conjunction with FIG. 13.

Figure 15A:
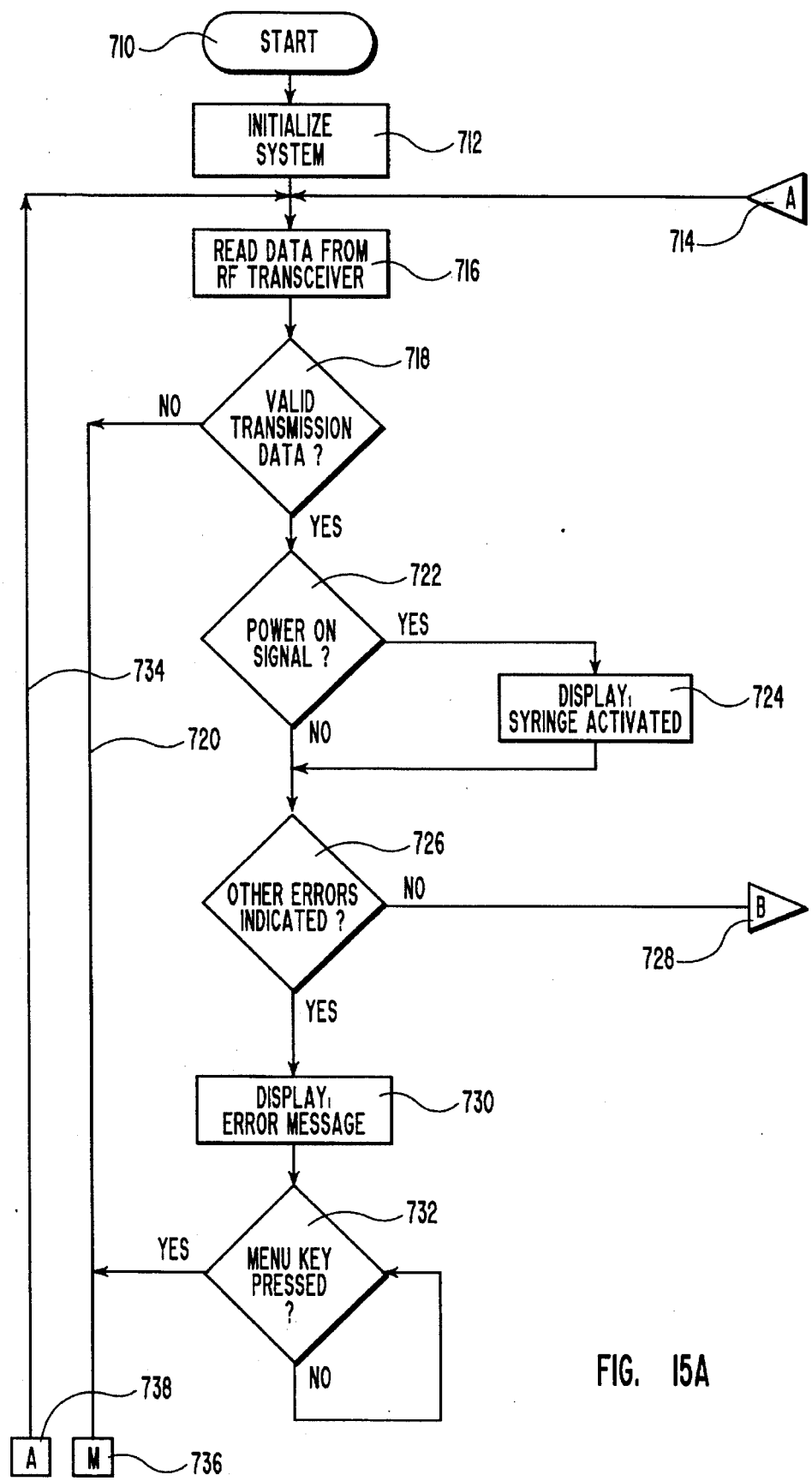
FIGS. 15a through 15f taken together illustrate a flow chart showing one presently preferred method for programming the digital processor of the remote console shown in FIG. 13.

With reference to FIG. 15A, when the remote console 402 is powered on, the program starts as indicated at step 710 and then moves to step 712 which causes the system to initialize. During initialization, the appropriate program instructions are loaded from program memory 570 into the digital processor 564 (shown in FIG. 13). The system then moves to step 716 which causes the processor 564 to read the data contents of the RF transceiver circuit (562 in FIG. 13). The processor 564 then, in step 718, checks whether the contents of the RF transceiver 562 constitutes valid transmission data that has been transmitted by the RF transmission module 400. If the transmission data is not valid, the process will move as indicated at flag 736 to the portion of programmed instructions illustrated in FIG. 15B.

If however the transmission data is valid, the processor 564 will move to step 722, and check whether the RF transmission module 400 has transmitted a "power on" signal. If so, the processor will cause a message to be output on the graphic display 404 signifying that the syringe has been activated at step 724, and then proceed to step 726. If a power on signal has not been transmitted, the processor 564 will proceed directly to step 726, where it will check to see if any other errors have been detected and transmitted by the RF transmission module 400. If there are not any other errors indicated, the processor moves as indicated at flag 728 to the portion of the programmed instructions illustrated in FIG. 15D, described in further detail below. If there are errors detected, the processor 564 will cause a corresponding message to be displayed on the graphic display 404 indicating that a particular error has occurred at step 730. The processor will then await acknowledgement from the user by waiting for the user to press the menu switch 408 or 416, as is indicated at step 732. Once the user has depressed the menu switch 408 or 416, the process will move, as is indicated at flag 736, to the portion of the programmed instructions illustrated in FIG. 15B.

Figure 15B:
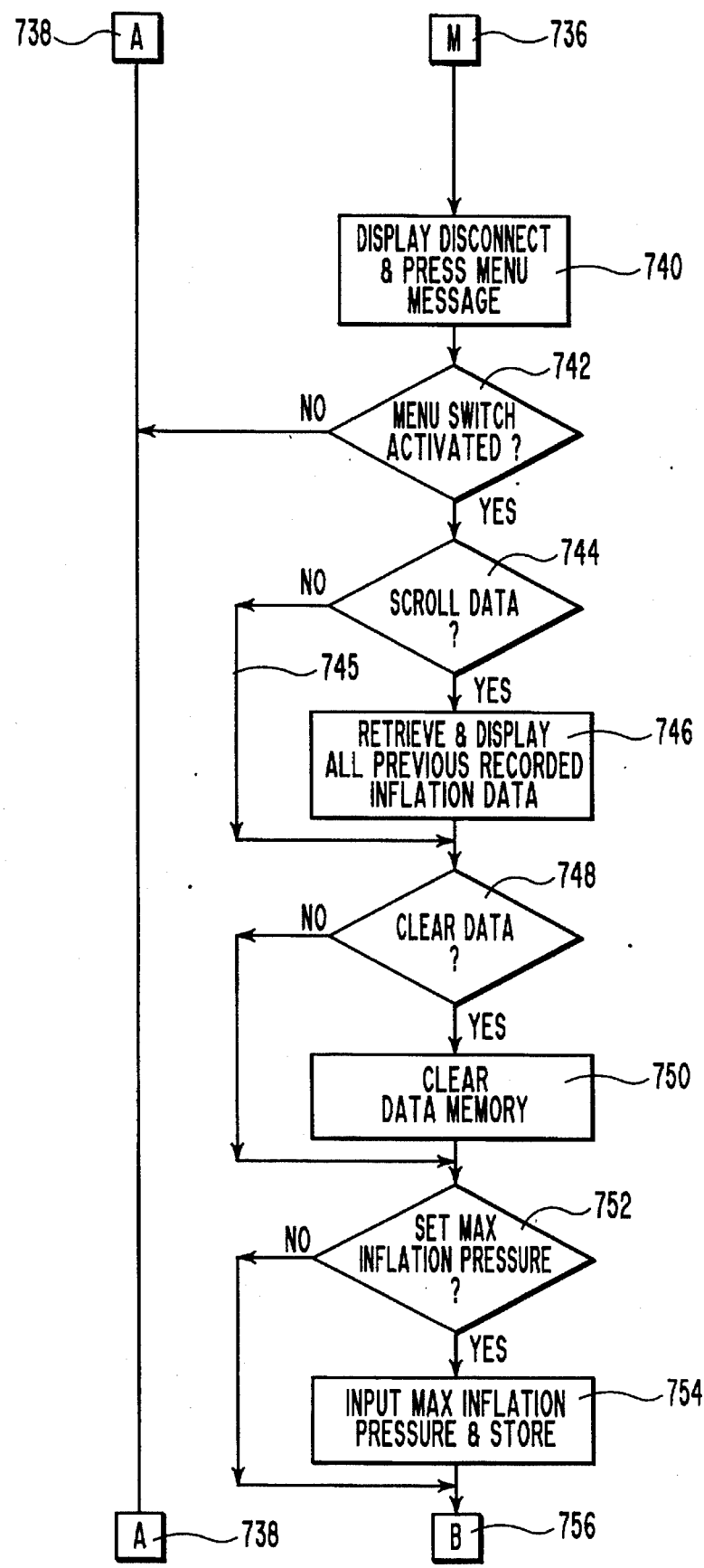

As is indicated at step 740 in FIG. 15B, the processor 564 will cause a message to be displayed on the graphic display 404 signifying that the RF transmission module 400 is not communicating with the transducer 42 and instruct the user to press the menu switch 408. The processor then moves to step 742 to check whether the menu switch 408 has been activated and if not returns to step 716 as schematically illustrated at 738 and continues in that loop until the menu switch 408 or 416 is activated by the user.

Once the menu switch is activated at step 742, the processor then moves to step 744 and causes the graphic display 404 to display a message inquiring whether the inflation data previously recorded by the system 14b is to be scrolled at the graphic display 404. If the system user desires to review the previously recorded inflation data, the select switch 410 or 418 is activated and the processor 564 then proceeds to step 746 which causes all of the previously recorded inflation data for each inflation event to be retrieved in sequence and displayed. If at step 744 the system user does not wish to scroll the previously recorded inflation data, the menu switch 408 or 416 is activated which causes the processor 564 to skip step 746 as schematically illustrated at line 745 so as to proceed with the next inquiry as represented at step 748.

At step 748 the system causes a message to be displayed on the graphic display 404 inquiring whether previously recorded inflation data which has been previously stored in the data memory 580 is to be cleared. If the select switch 410 or 418 is activated this causes the processor 564 to clear the previously recorded inflation data from data memory 580, as indicated at step 750. If the previously recorded inflation data is not to be cleared from data memory 580, the menu switch 408 or 416 is activated which causes the system to skip step 750 and to move to the next inquiry as represented at step 752.

Figure 15C:
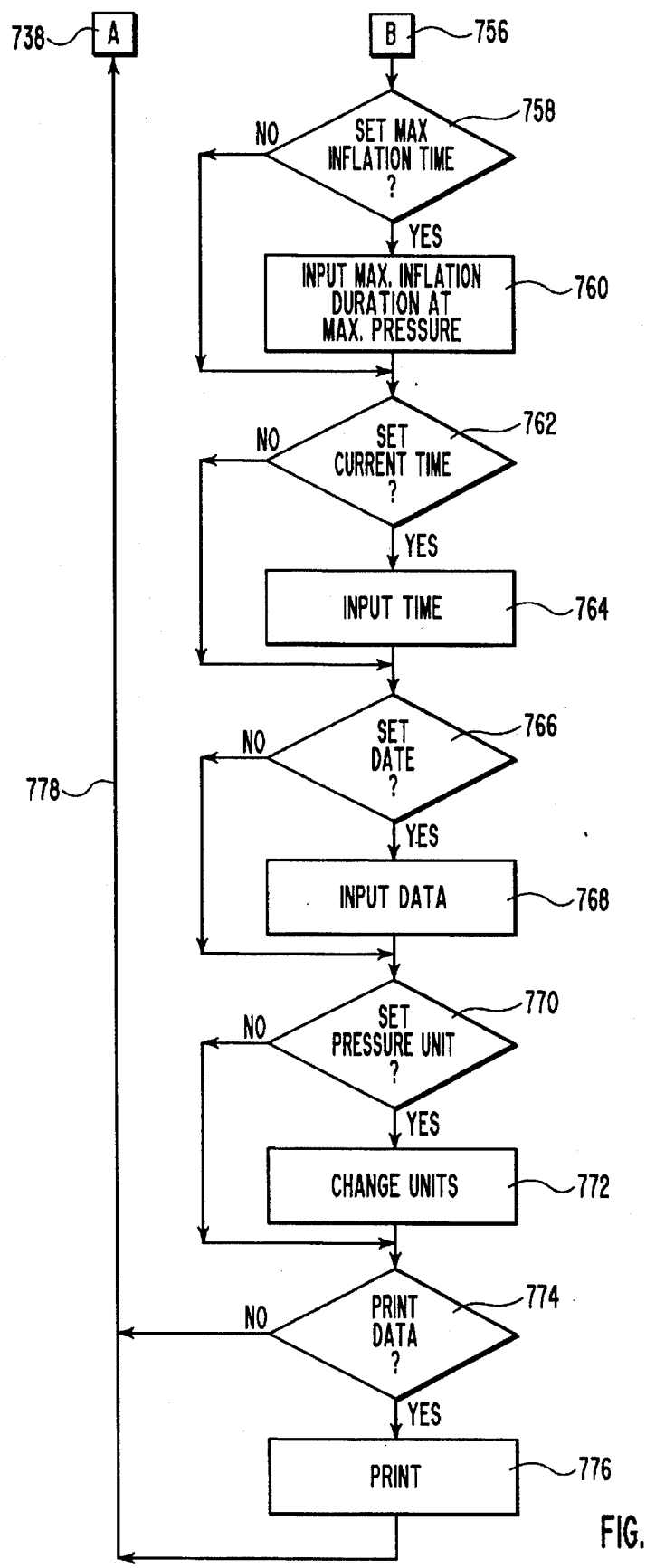

At step 752 the system causes the graphic display 404 to display an inquiry with respect to whether an upper limit is to be set with respect to the maximum positive inflation pressure to be applied with respect to the next inflation event. If so, the select switch 410 or 418 is activated and is used to input the selected maximum positive inflation pressure through the data transfer bus 572 (FIG. 13), to the data memory 580 for later reference, at step 754. If a maximum inflation pressure is not selected at step 752, the menu switch 408 or 416 is activated which causes the system to skip step 754 and move to the next inquiry, via flag 756, as represented at step 758 (FIG. 15C).

At step 758 the system displays a message at the graphic display 404 inquiring whether the maximum duration for application of positive pressure is to be selected. If so, the select switch 410 or 418 is again activated which causes the system to move to step 760 and the select switch 410 or 418 is then used to input at the graphic display 404 the selected duration. This selected duration is input by means of the corresponding graphic display circuitry 578 (see FIG. 13) through the data transfer bus 572 to the data memory 580 for later reference.

In a manner similar to that described above in connection with the preceding inquiry steps, the system continues to inquire whether the current time and date are to be displayed, as represented at steps 762 and 766, respectively. If so, by utilizing the select switch 410 or 418 as described above, the current date and time may be entered at the graphic display 404. However, the internal clock that is part of the circuitry in processor 564 will typically make it unnecessary to enter these parameters. The system then moves through the series of steps represented at 770, 772, 774, and 776 where it determines the pressure units to be displayed at the graphic display 404 as well as determining whether data is to be printed. After the print inquiry has been responded to by utilization of the appropriate menu or select switch 408, 416 or 410, 418 respectively, the system returns as illustrated at line 778 to step 716.

As will be appreciated from the foregoing, the portion of the program instructions which are carried out according to the flow chart of FIGS. 15A–15C pertains to that part of the program which permits a series of optionally selectable functions to be sequentially displayed for purposes of inputting various control parameters which are later utilized in displaying and automatically recording the data, as well as utilizing these control parameters to alert the system user when selected limits are reached with respect to maximum positive inflation pressure and duration of positive inflation pressures.

Figure 15D:
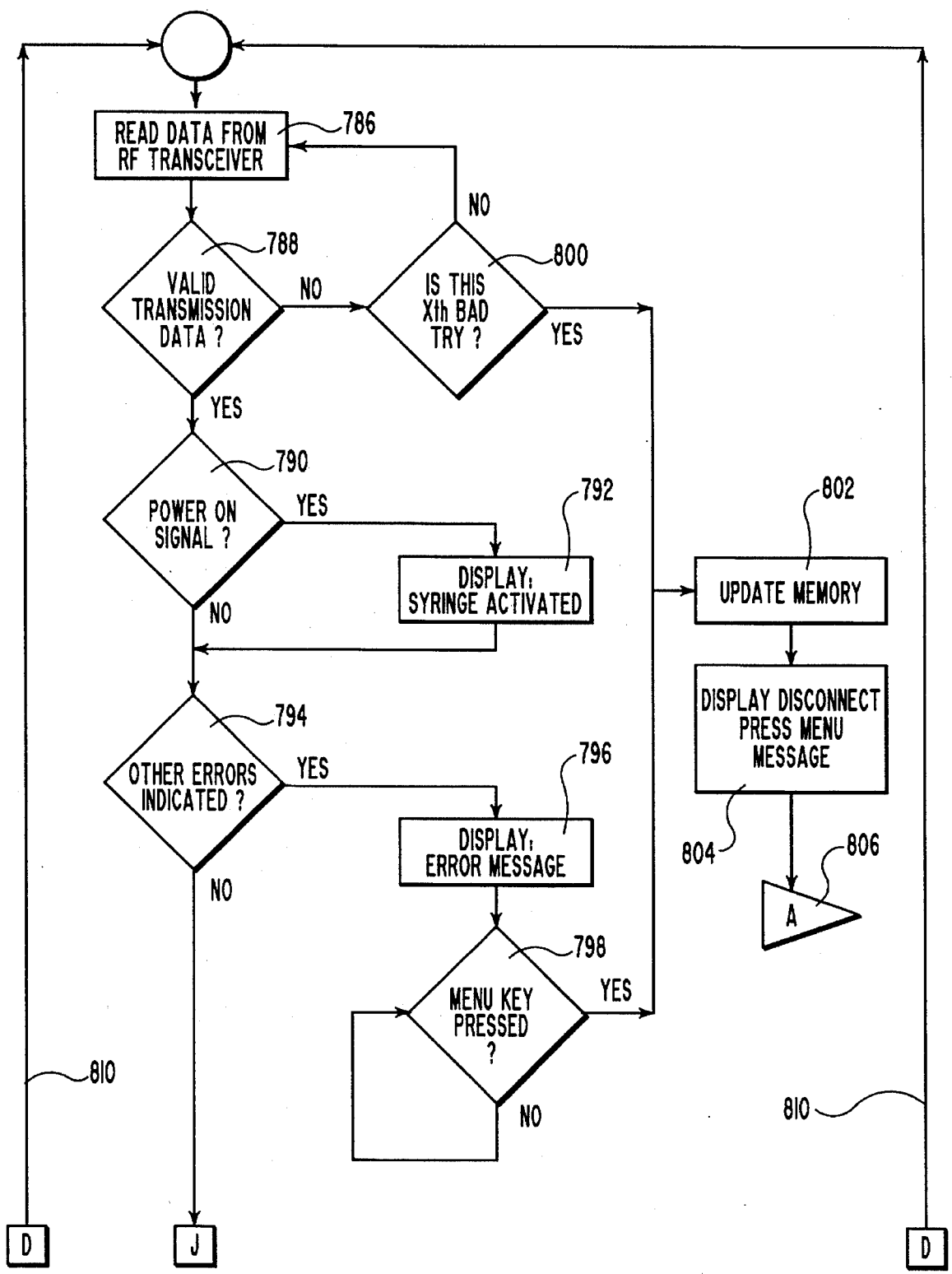
Figure 15E:
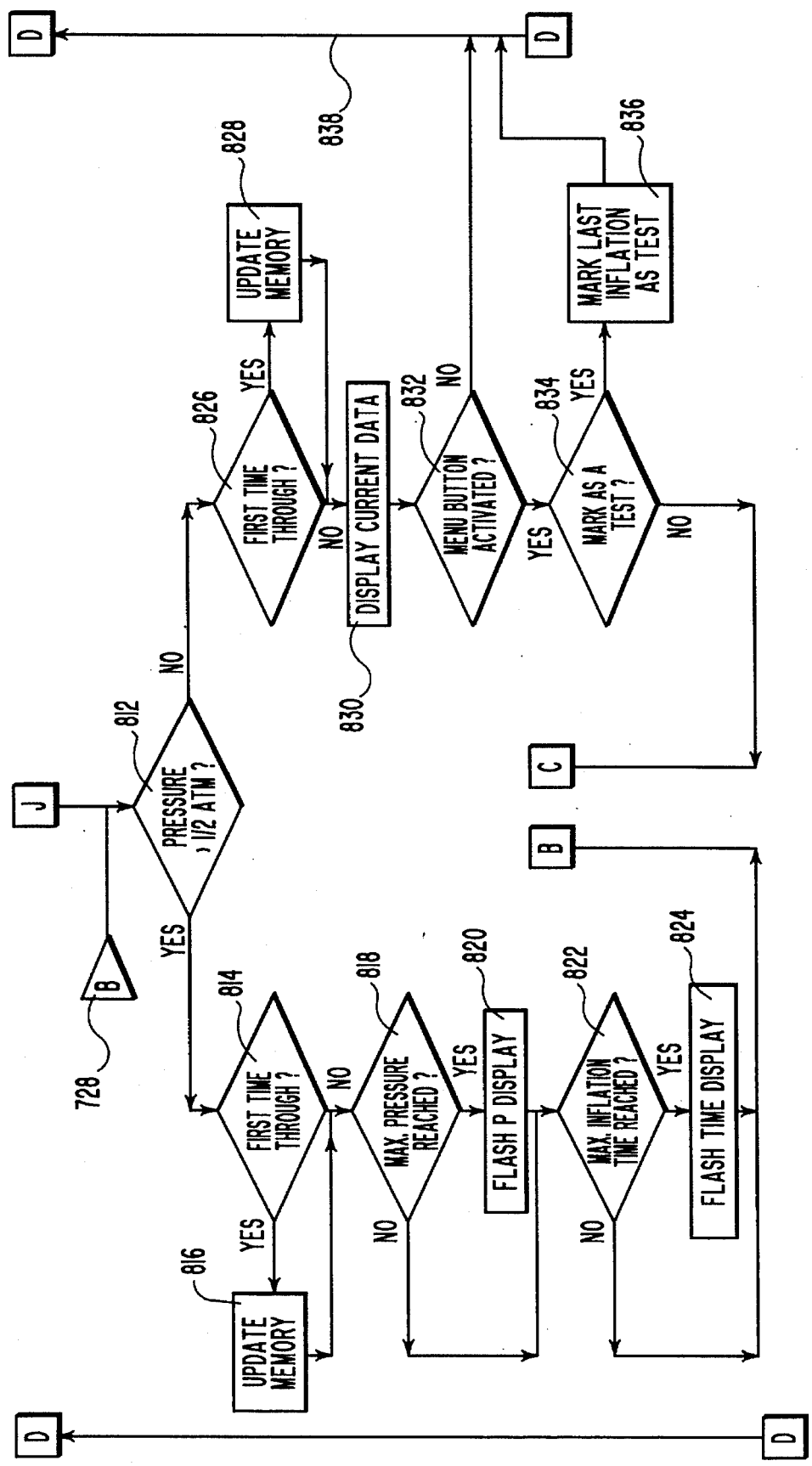
Figure 15F:
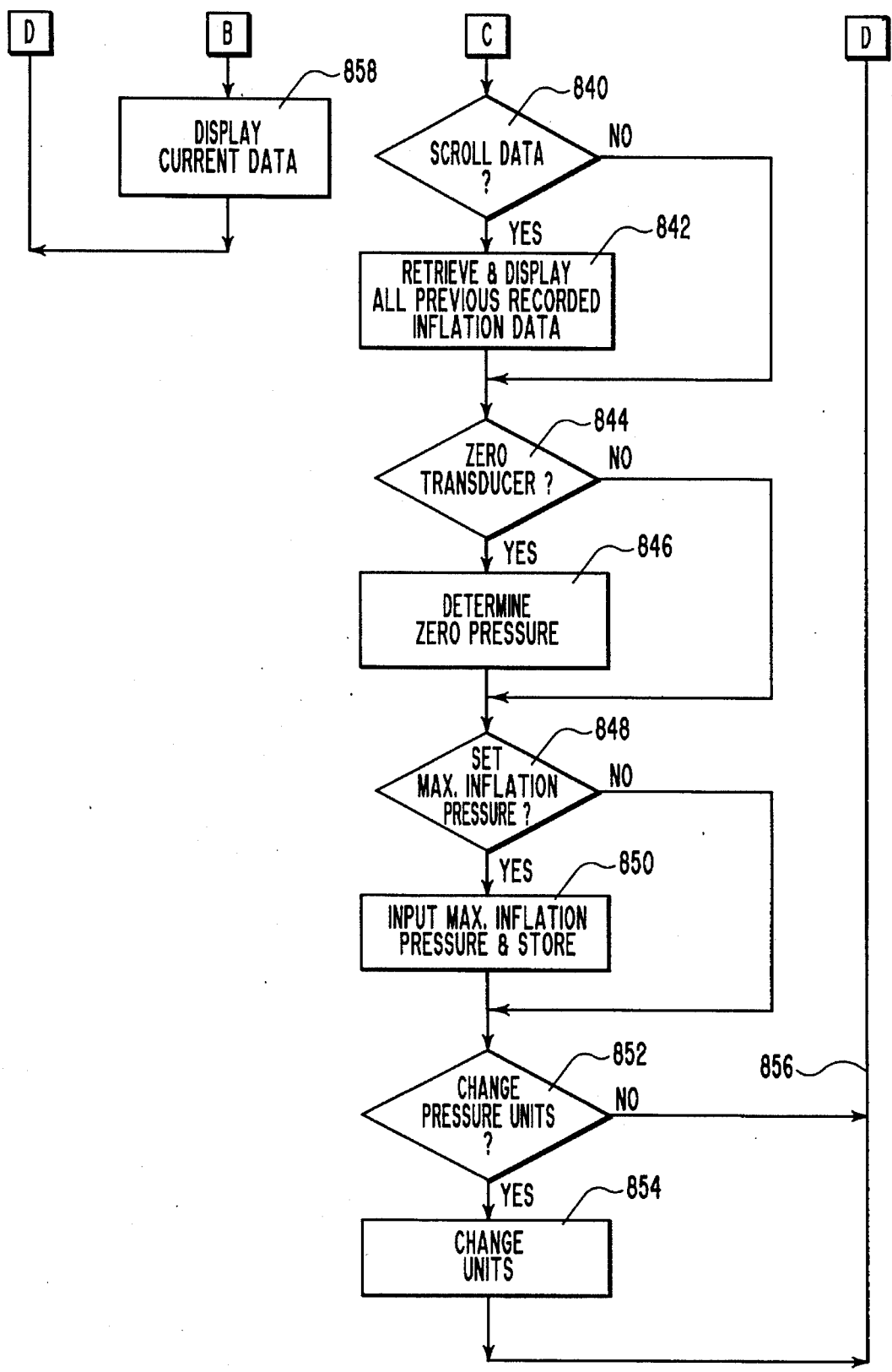
Figure 15G:
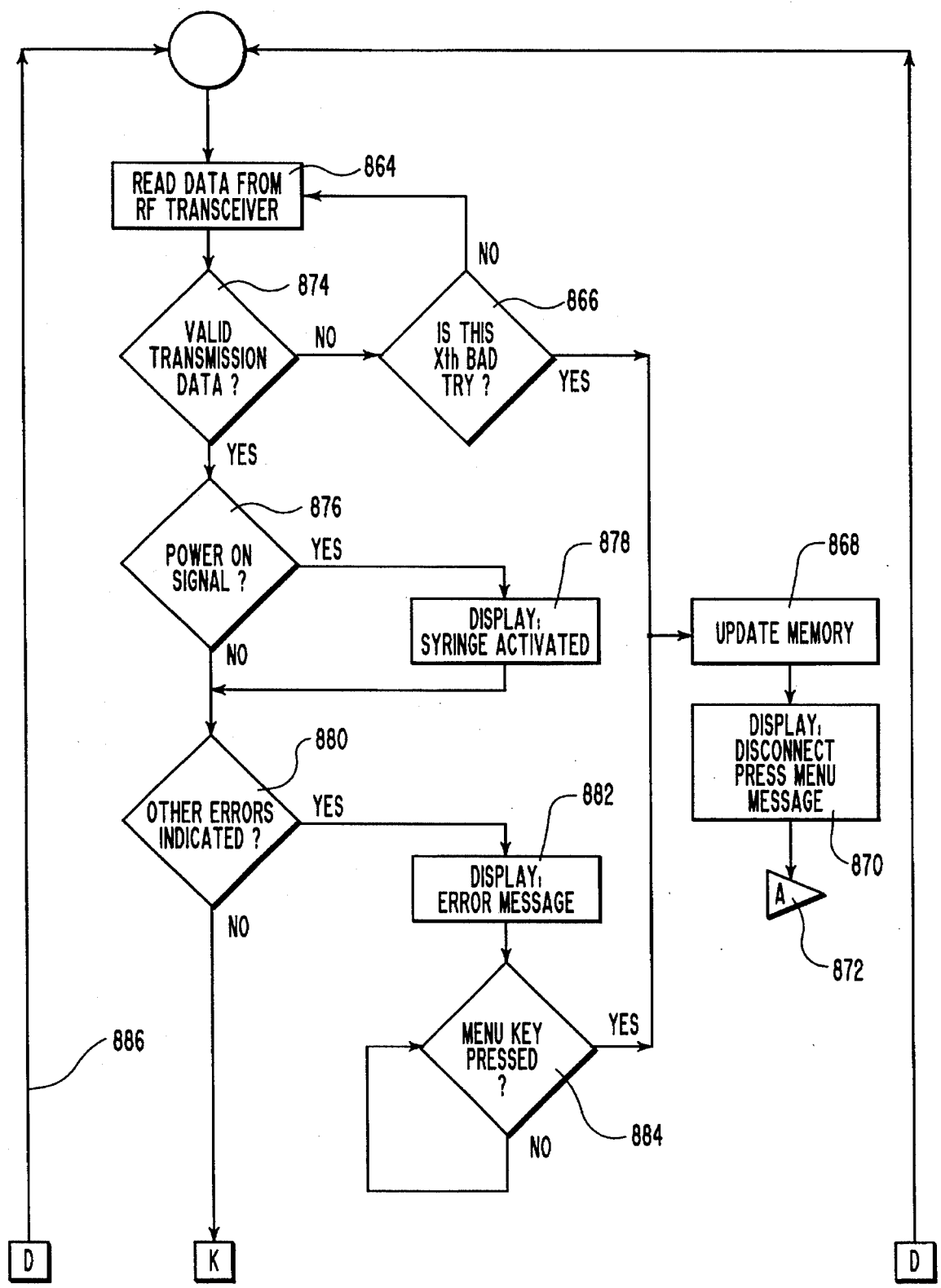
FIGS. 15g through 15j taken together illustrate a flow chart showing a second presently preferred method for programming the digital processor of the remote console shown in FIG. 13 in accordance with another method of the present invention.

Once the transducer 42 is properly connected to the RF transmission module 400, the remote console 402 processor 564 moves to that portion of the program illustrated in FIGS. 15D–15F, as is indicated at Flag 728 (FIG. 15E), where it then starts as schematically indicated at step 812. At this portion of the program, processor 564 begins to monitor the pressure values transmitted by the RF transmission module 400.

Thus, if the pressure which is sensed at transducer 42 is less than one-half atmosphere, the system moves to that portion of the program which commences with step 826. At that step the system first determines whether it is in the first pass through of the loop started by step 826 and if so moves to step 828 where the data memory 580 is updated. The effect of updating the data memory 580 at step 828 is that the time with respect to termination of the last inflation is recorded and stored in the data memory 580. Once that step has been completed, the system then moves to step 830. In the alternative, if at step 826 the system determines that it is not the first pass through this loop of the program, the system moves directly to step 830 and displays the current data with respect to the inflation number, duration time, and pressure. The system then moves to step 832 where the processor 564 checks the status of the menu switch 408 or 416.

If the menu switch 408 or 416 is activated in this condition the system moves to the next step 834 where the last inflation data can be marked as an initial test or not, as desired by the system user. If the initial inflation is merely a test it is marked at step 836 prior to returning to step 786 (via line 838), otherwise the system moves to step 840 (FIG. 15F) to determine whether any previously recorded inflation data is to be scrolled. If the data is scrolled the system moves to step 842 and retrieves and displays in sequence all previously recorded inflation data for each prior inflation event, otherwise the system jumps to step 844.

Similarly, the system can also proceed through steps 844, 848, and 852 which will permit the transducer 42 to again be zeroed (step 846), or to set a new maximum positive inflation pressure (step 850) or to change the pressure units (step 854) by entering any of these selections using the select switch 410 or 418. The system then returns to step 786 via line 856.

Once the inflation pressure applied to the balloon catheter begins to exceed a predetermined level, as for example about one-half atmosphere by insertion of the syringe plunger 24, the system moves from step 812 to the program step 814 (FIG. 15E). At that step the system determines whether this is the first time through the part of the program loop which begins with step 814 and if so updates the data memory 580 at step 816. The effect of updating the data memory 580 at step 816 is that the processor 564 causes the duration of the previous inflation to be recorded. After update memory step 816 has been performed, or in each subsequent pass through step 814, the system then moves to step 818 where the system checks to determine whether the inflation pressure has reached any selected maximum positive inflation pressure input for this inflation event. If the selected maximum inflation pressure is reached the system moves to step 820 and causes a pressure display readout portion on the graphic display 404 to begin flashing so as to signal the system user that the selected maximum inflation pressure has been reached. If the selected maximum inflation pressure has not been reached or if none was selected, the system then jumps to step 822.

At step 822 the system checks to determine whether any selected duration has yet been clocked with respect to a selected duration for application of positive pressure and if so then moves to step 824 so as to cause a time display portion on the graphic display 404 to begin flashing, thereby signalling the system user that the selected duration has been achieved. If no duration is input or if the selected duration has not been reached the system moves to step 858 (FIG. 15F) which causes the system to display the current data with respect to the inflation pressure being applied and the length of time that positive inflation pressure has been applied. The system then returns to the beginning of the loop at step 786.

At step 786, processor 564 reads the new contents of the RF transceiver 562 (FIG. 13). The system then checks whether this newly read data is valid transmission data at step 788. If the data is not valid, the system will continue to read the contents of the RF transceiver 562 for a predetermined number of iterations, as is indicated at step 800. Having exhausted the predetermined number of iterations, which indicates the communication link between the RF module 400 and the remote console 402 has been lost, the system will proceed to step 802 where data memory 580 will be updated so as to mark the time of disconnection. The system will then cause the graphic display 404 to display a "disconnect" message to the user and instruct the user to press the menu switch 408 or 416, and then will return to step 716, as is indicated at flag 806.

If data read from the RF transceiver 562 is valid at step 788, the system will proceed to step 790. There, the system checks the "power on" flag generated by the RF transmission module 400. If the flag is set, the system will cause the graphic display 404 to display a "syringe activated" message before proceeding to step 794. If the power on flag is not set, the system will proceed directly to step 794.

At step 794, the system will continue checking the status flags transmitted by the RF transmission module 400, as discussed above in connection with FIGS. 14A and 14B. If those flags indicate any error conditions, the system will cause the graphic display 404 to display an appropriate error message and will then wait for the user to acknowledge by pressing the menu key 408 or 416 at step 798. When the menu key is pressed, the system will update memory 580 at step 802 (so as to mark the time of disconnection), display a "disconnect" message on the graphic display 404 and instruct the user to press the menu switch 408 or 416 at step 804, and then return to step 716, as is indicated at flag 806. If no errors are indicated, the system will proceed to step 812 (FIG. 15E) and continue to monitor and process the inflation data transmitted by the RF transmission module 400, in the same manner as described above.

4. FIGS. 15G–15J.

Figure 15H:
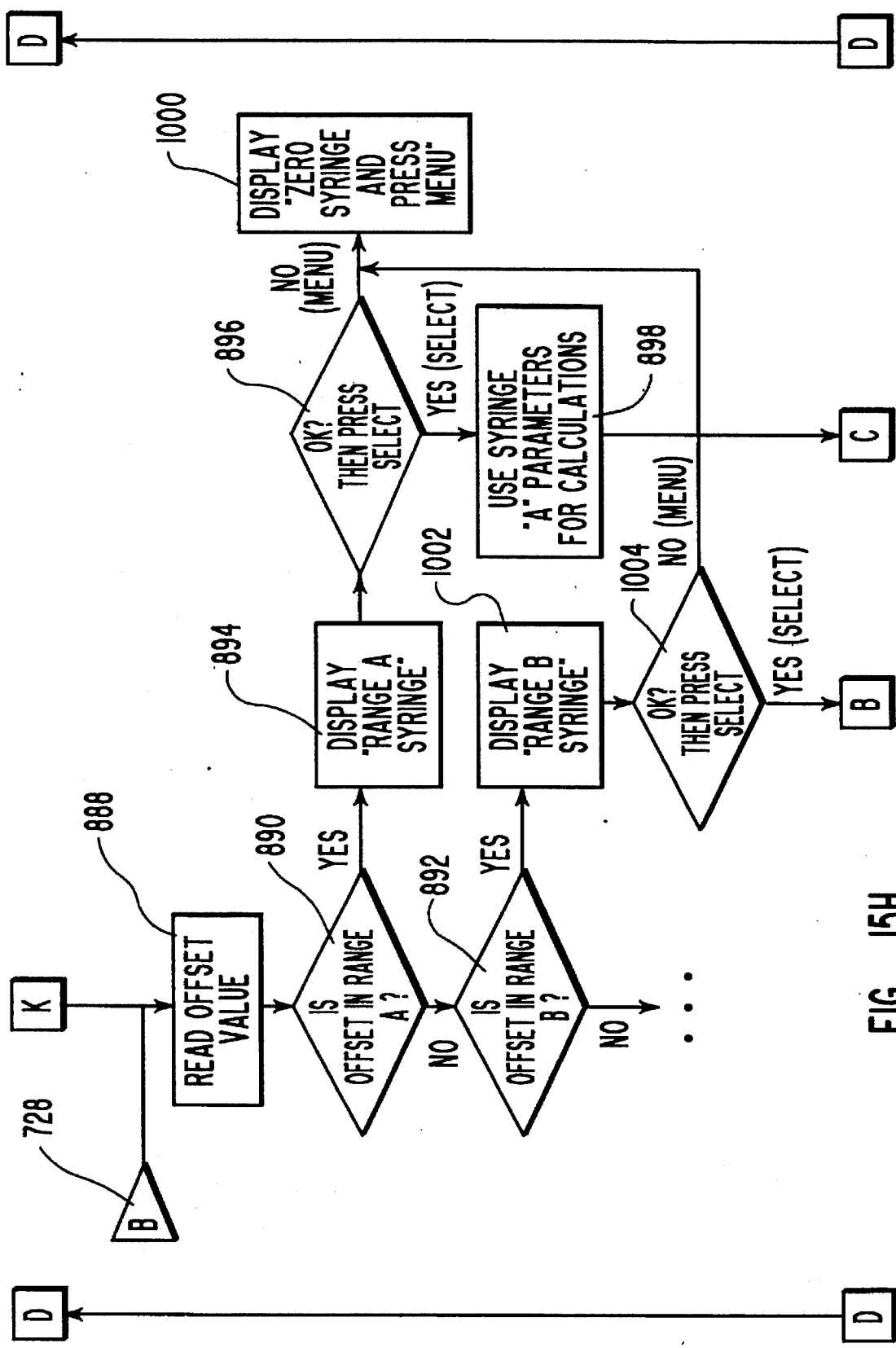

An alternative embodiment for programming and controlling the remote console 402 is illustrated in FIGS. 15G–15J. This portion of the program instructions can be used in the place of those instructions illustrated in FIGS. 15D–15F. As with those sets of instructions, once the transducer 42 is properly connected to the RF transmission module 400, the remote console 402 processor 564 moves to the portion of the program illustrated in FIGS. 15G–15J as indicated at Flag 728 (FIG. 15H).

At step 888 (FIG. 15H) the microprocessor 564 proceeds to read the offset value of the connected transducer 42. The transducer offset value is the actual pressure which is read by the transducer 42 when there is no pressure applied by the syringe system 14b.

This offset is then compared to a plurality of offset values which have previously been stored in the program memory 570 of the microprocessor 564. By taking the difference between the actual offset value and the other previously stored offset values which have been programmed into the microprocessor 564, it can be determined whether the actual measured offset value is within any one of a number of preselected ranges for the offset value.

For example, as illustrated in FIG. 15H at step 890, it may be determined whether the measured offset is within a first range, range A. If so, the system then displays a message at step 894 to the system user which identifies to the user the particular offset range which was identified and the type of syringe which corresponds to that range of offset values. In other words, the transducer 42 may be designed so that it has a selected value of offset at the time the transducer circuit is manufactured.

If the system determines at step 890 that the measured offset value is not within a first range, range A, the system then moves to step 892 where a similar determination is made for the next range of offset values, range B. At steps 1002, 1004 and 1006 the system follows the same type of program steps previously described in connection with steps 894, 896 and 1000. In this fashion the system continues to check until it determines which selected range of offset values corresponds to the type of transducer 42 which is contained on the syringe that has been connected for use, identifies the user of this and then awaits for the user to confirm that this is the proper type of transducer with the appropriate parameters for the selected procedure or type of patient.

Figure 6A:
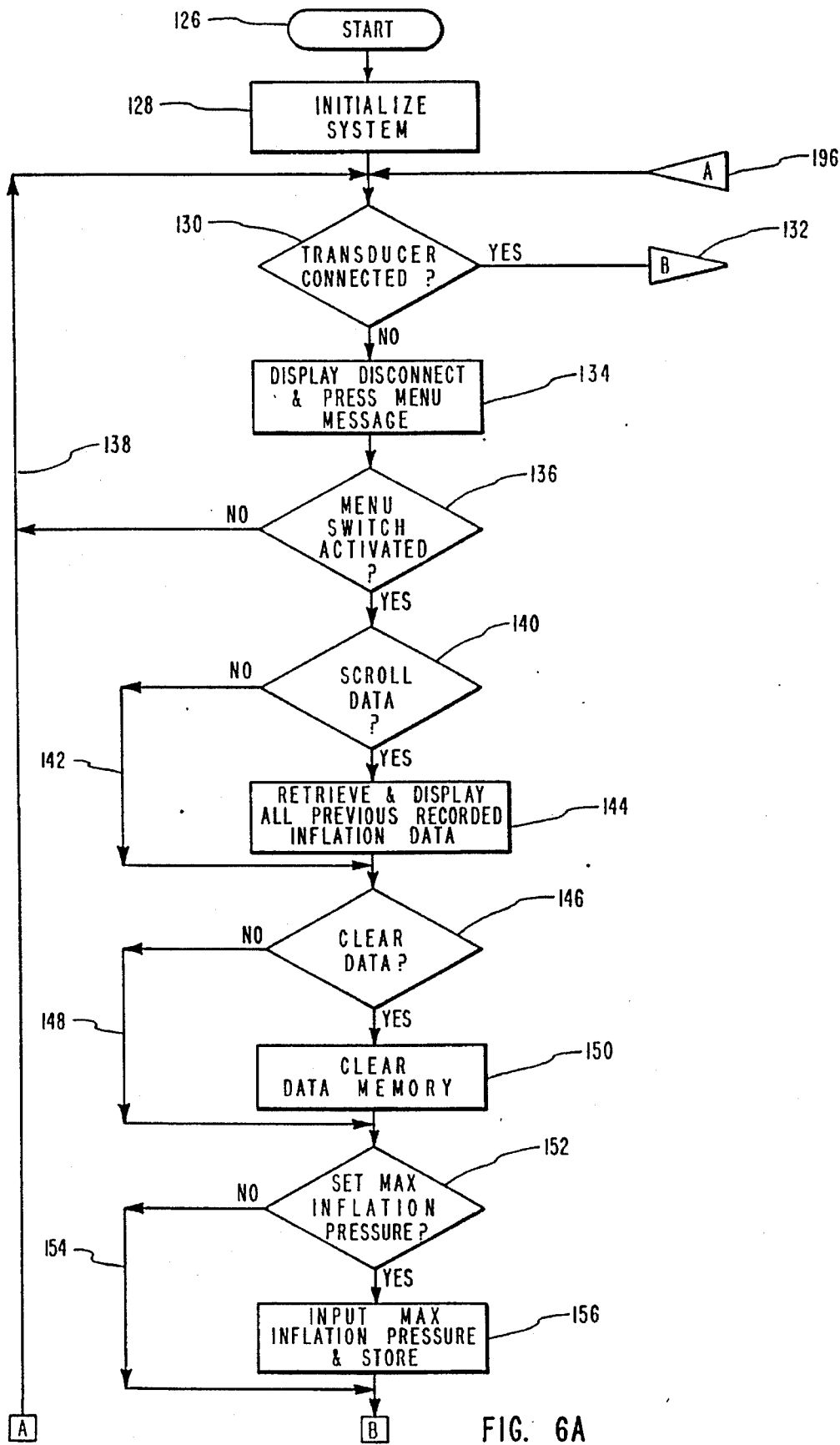
FIGS. 6A through 6D taken together illustrate a flow chart showing one presently preferred method for programming the digital processor of the electronic circuit means in accordance with the method of the present invention.
Figure 6B:
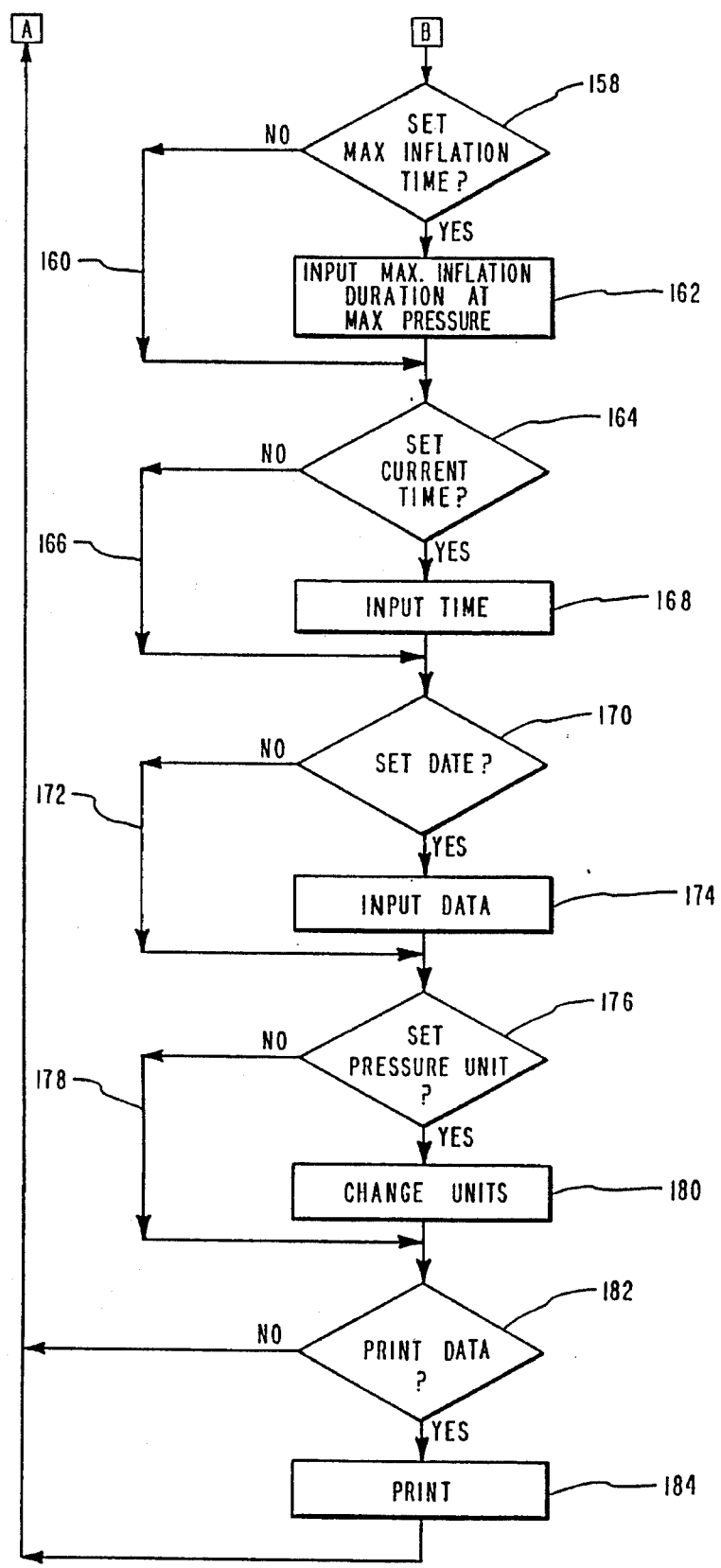
Figure 6C:
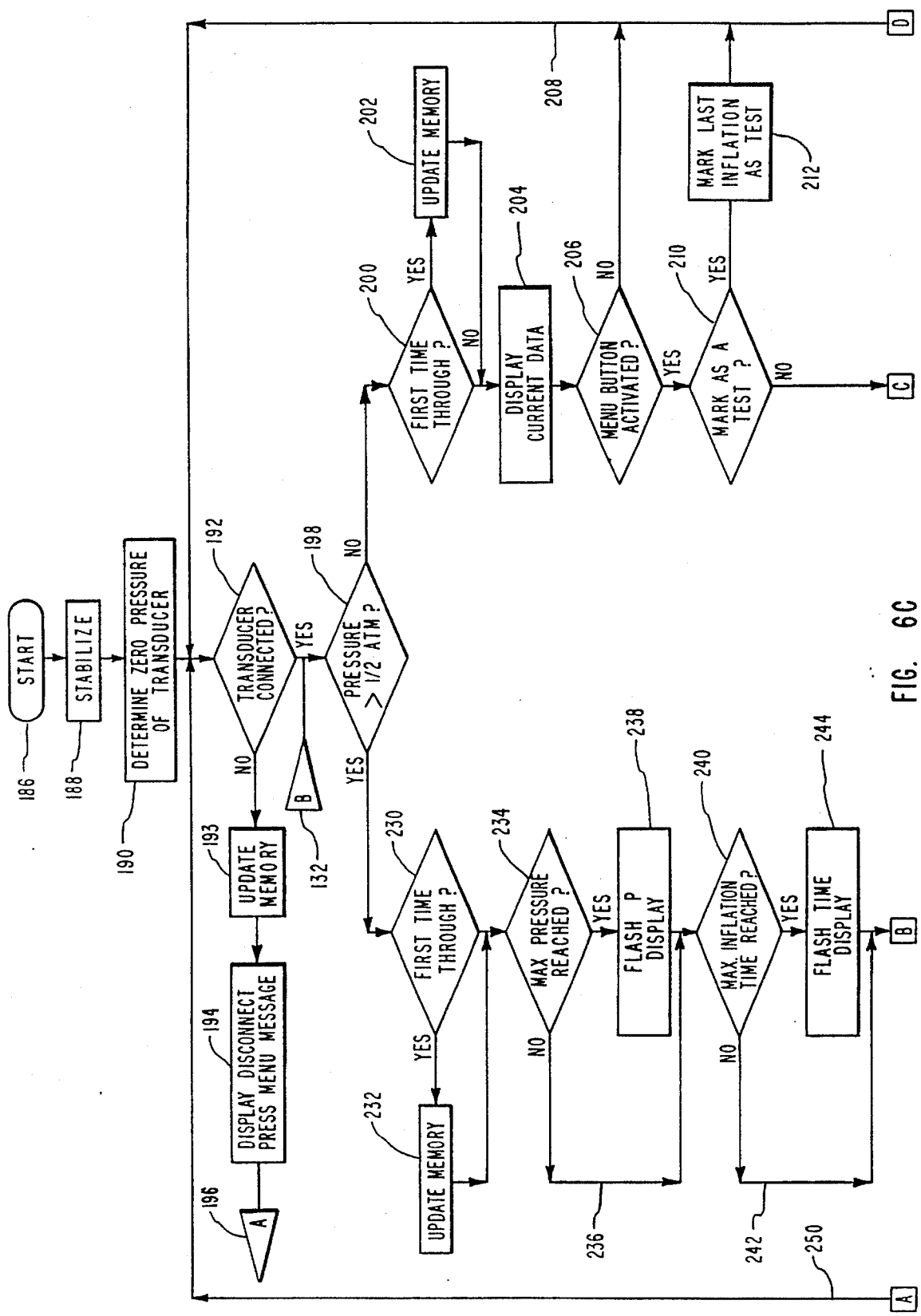
Figure 6D:
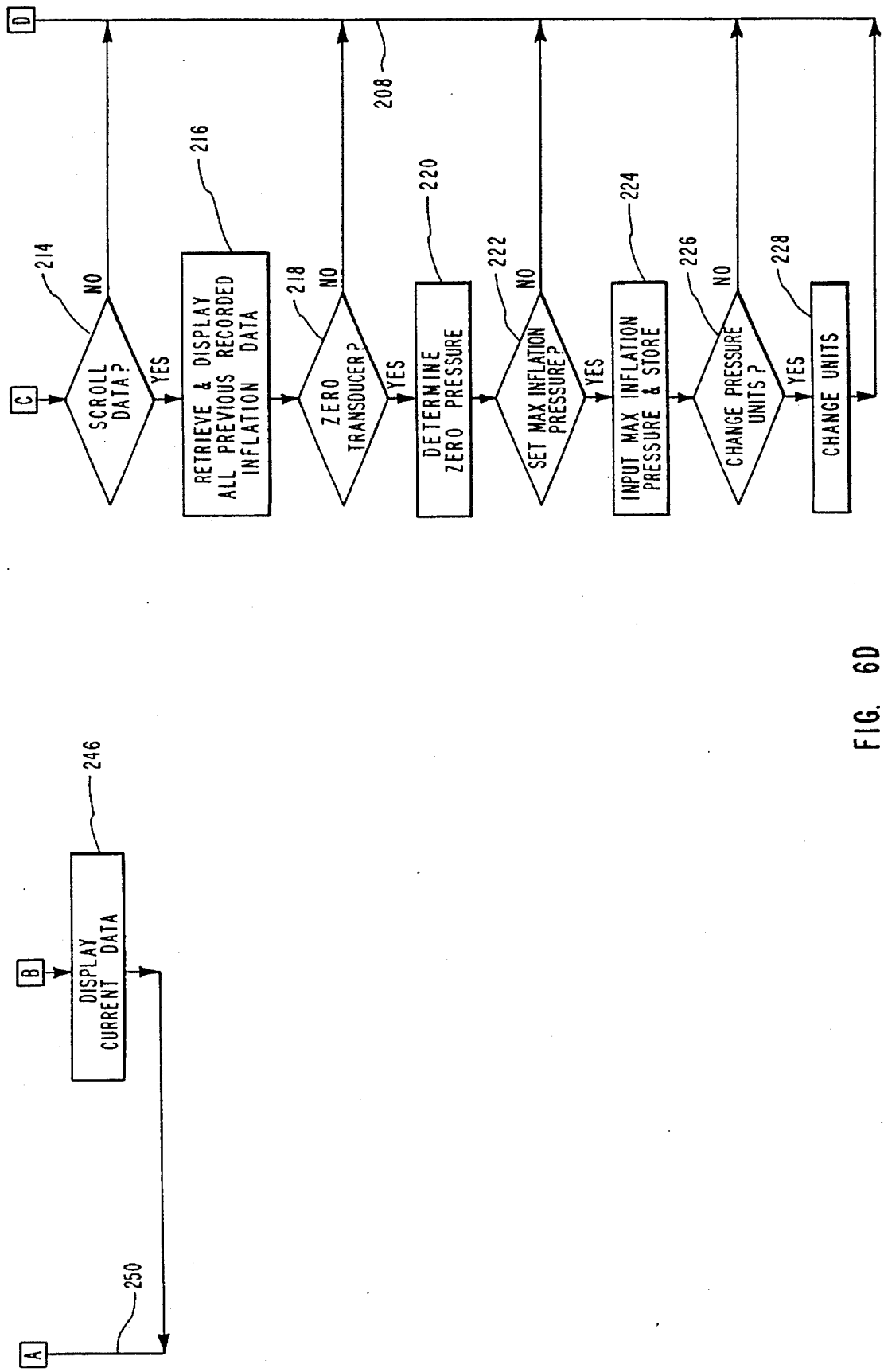
Figure 6E:
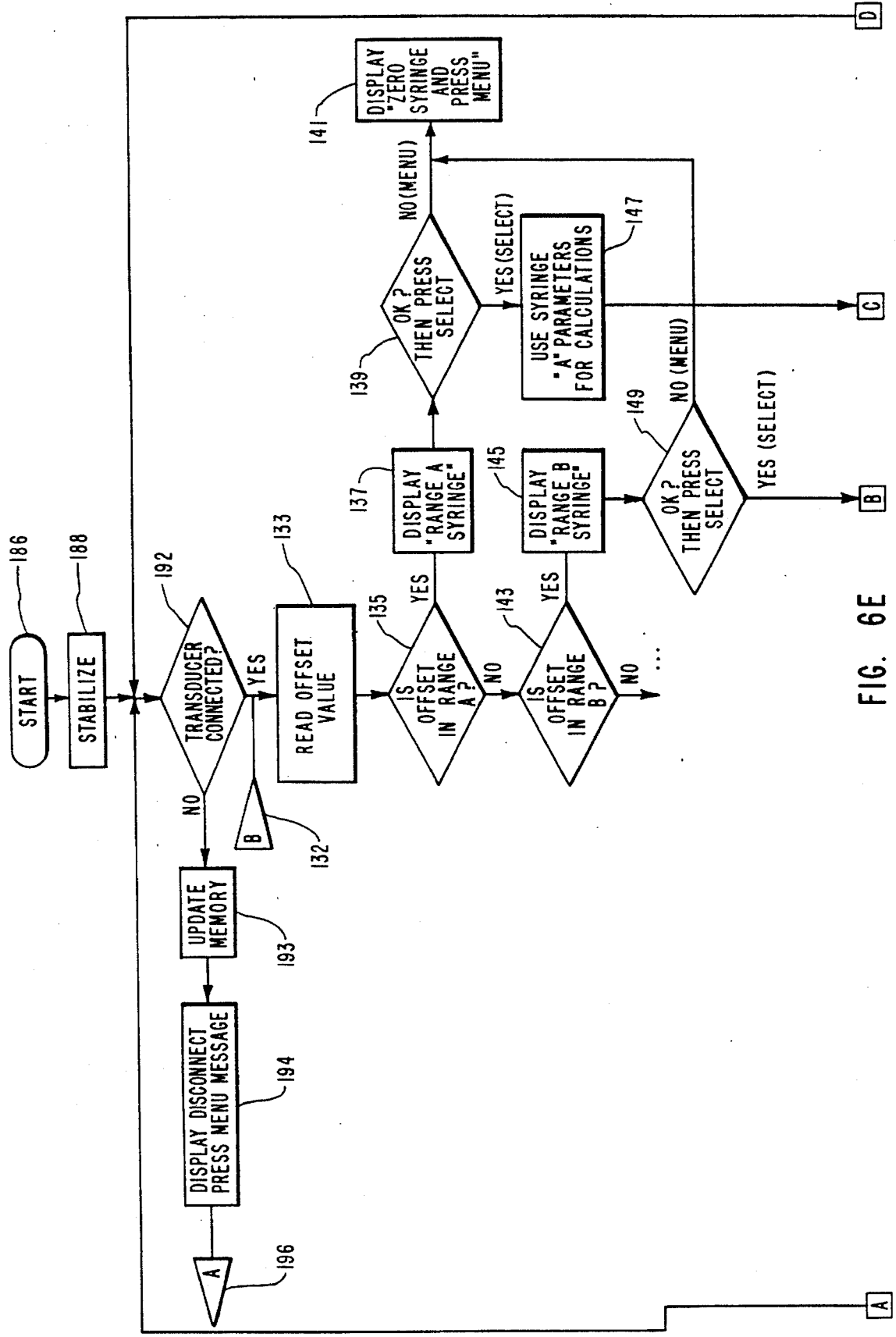
FIGS. 6E through 6G taken together illustrate a flow chart showing a second presently preferred method for programming the digital processor of the electronic circuit means utilized in the syringe system of FIGS. 2–5 in accordance with another method of the present invention.
Figure 6F:
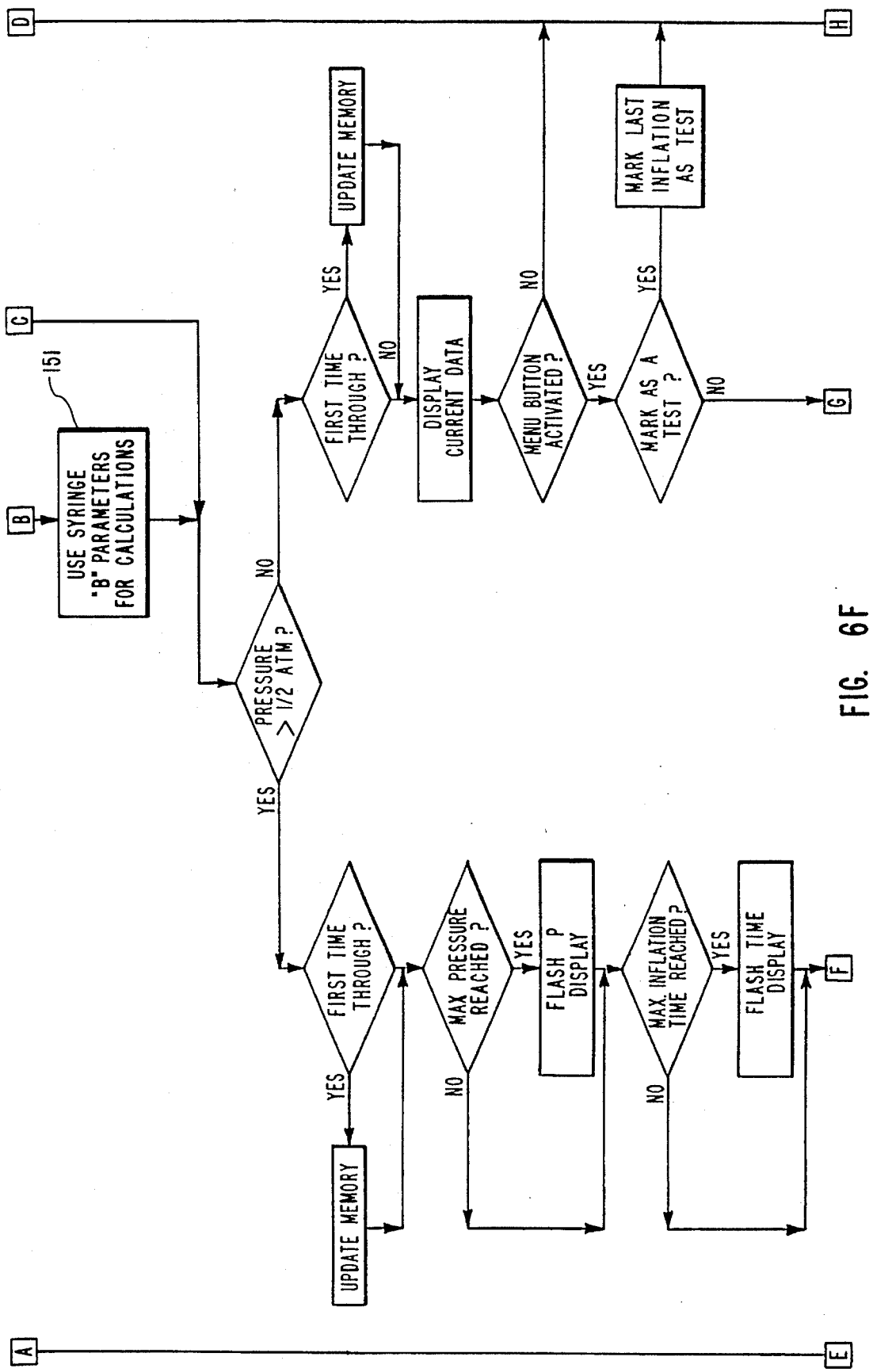
Figure 6G:
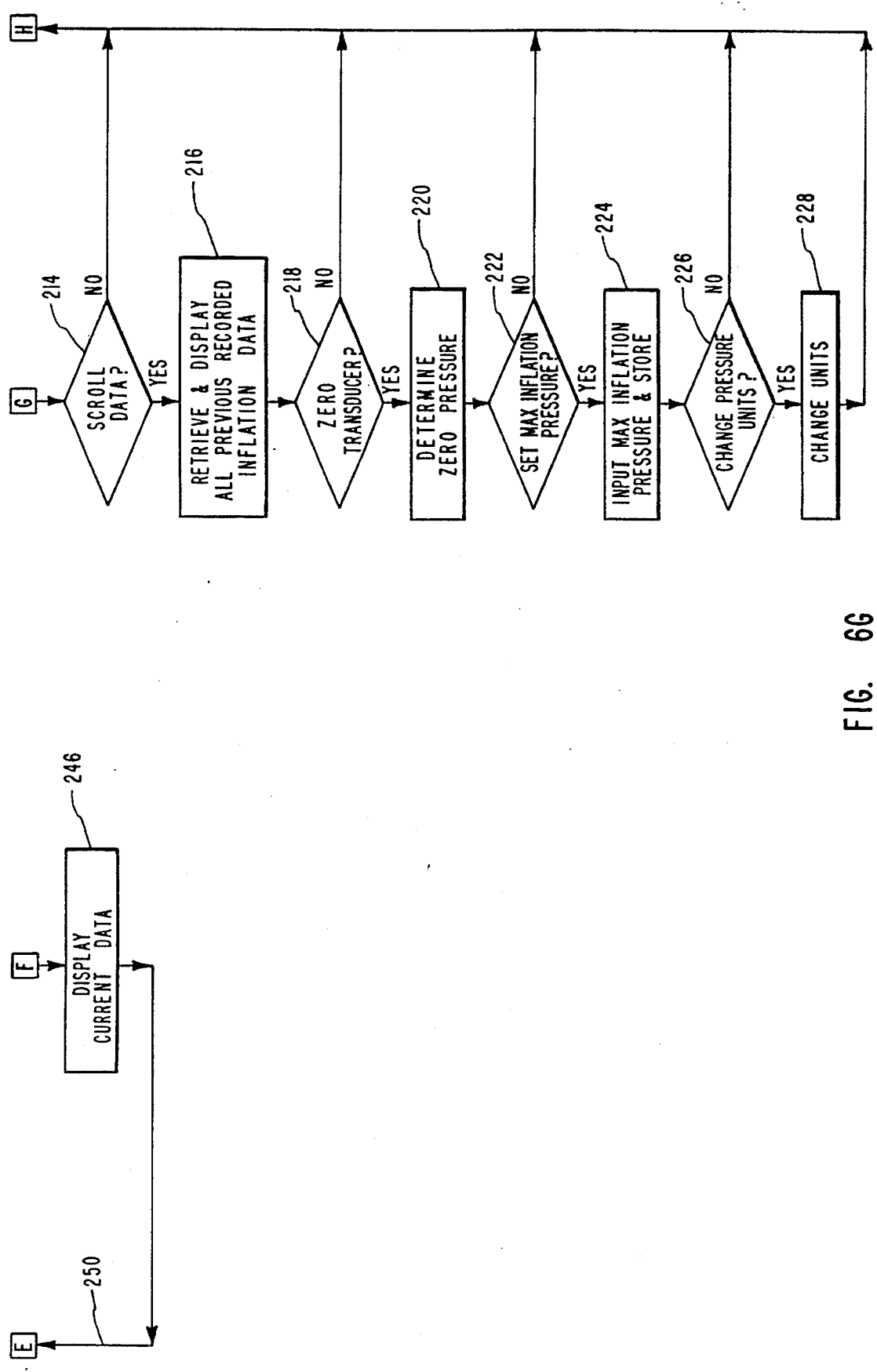

As discussed in conjunction with the same method described for controller 20 in FIG. 6E, this method can advantageously be used to identify different types of syringes that may be useful for different types of applications or patients. In this manner, the system can identify whether the correct type of syringe has been placed into use for the intended application or the type of patient for which the procedure is being conducted.

Figure 15I:
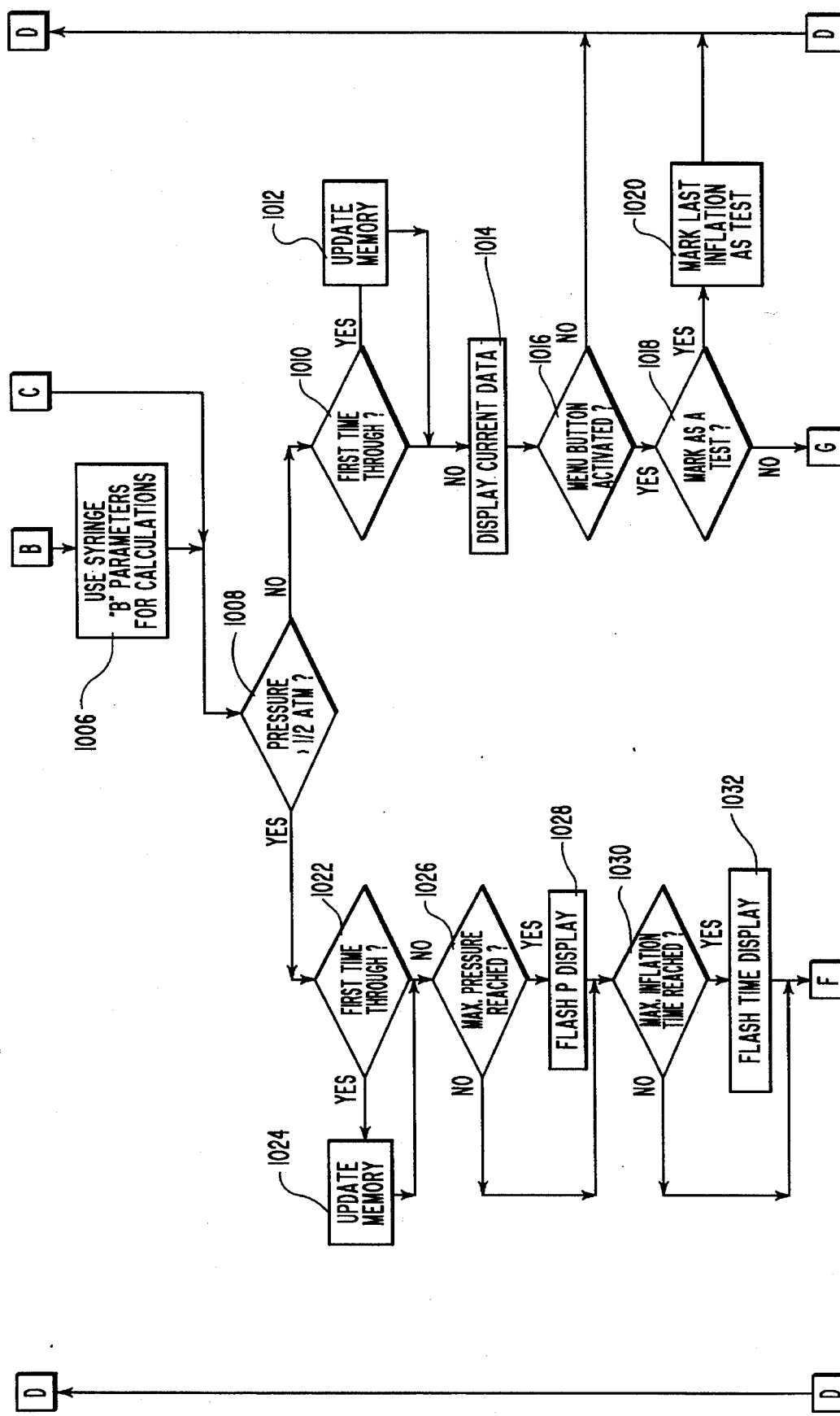
Figure 15J:
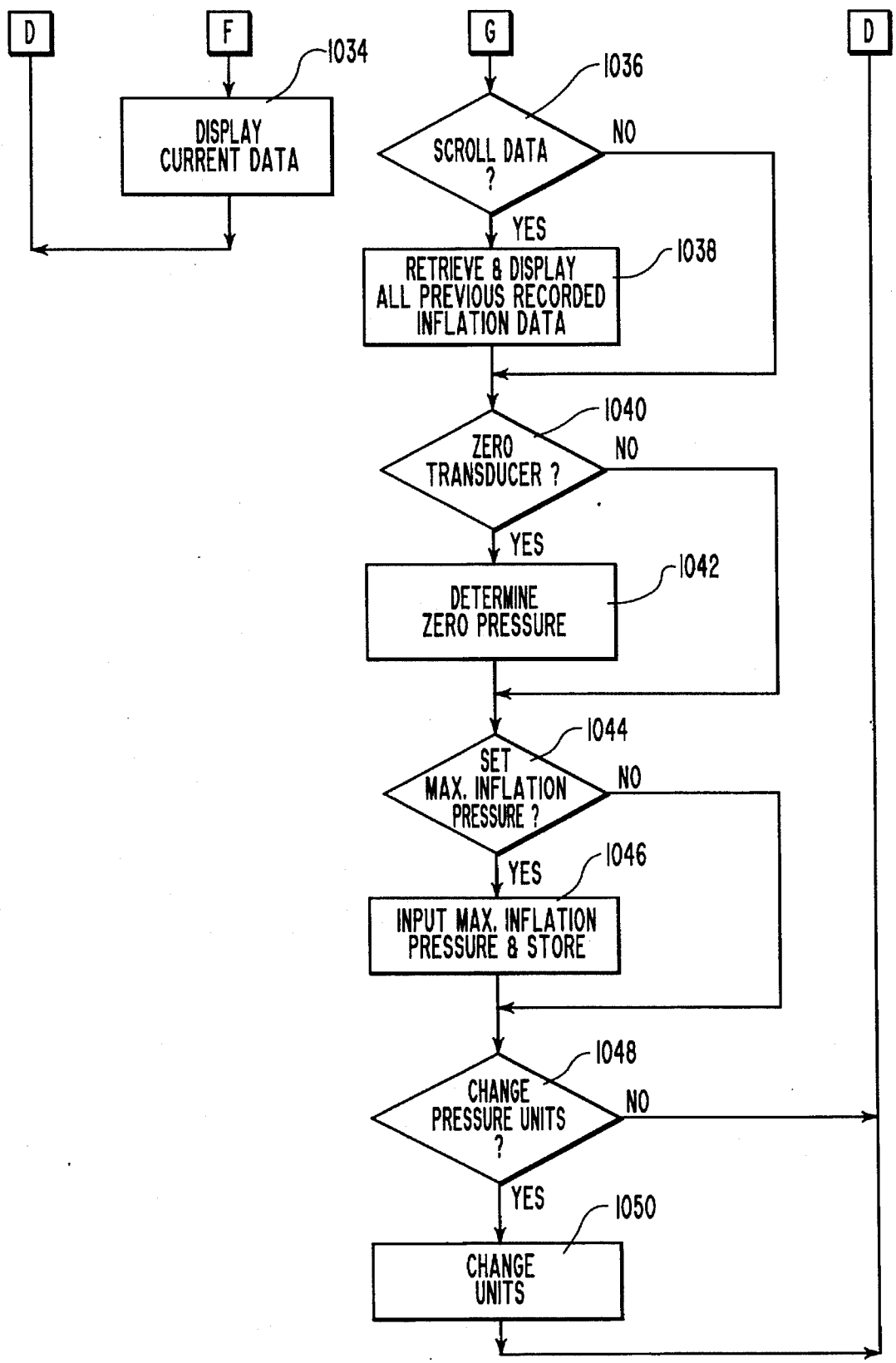

Thus, the system proceeds to identify the type of syringe attached in a manner identical to the method of FIG. 6E. Having identified the syringe type, the remaining digital processing steps, which are illustrated at FIGS. 15I–15J starting at step 1008 (FIG. 15I) are the same as those which have previously been described in connection with the embodiment of FIGS. 15A–15F.

Thereafter, the system then carries out step 864 where data is read from the RF transceiver 562 and it is determined whether the transmission data is valid (step 874), in the same manner as previously described in conjunction with the embodiment of FIG. 15D. Also, in the same manner as described above for FIG. 15D, the system proceeds to check for the power on signal (step 876) and for other errors detected by the RF transmission module (step 880). If no errors are indicated, the system will proceed to step 888 (FIG. 15H) and continue to monitor and process the inflation data transmitted by the RF transmission module 400, in the same manner as described above.

It will be appreciated that the second digital processor (564 in FIG. 13), is preferably a 8032 microprocessor (as in controller 20 discussed above) as identified in Table I, and could be programmed so as to implement the above-described method using any one of a variety of different programming languages and programming techniques.

The invention may be embodied in other specific forms without departing from its spirit or essential characteristics. Accordingly, the described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

TABLE I

| Schematic Reference | Part |
|---|---|
| X1 | 11.059 MHZ |
| C3 | 10 Mfd |
| R1 | 8.2K |
| U1 | 8032 |
| U2 | 74HC573 |
| C5, C7, C14 | .01 Mfd |
| C1, C2 | 33 pf |
| P1 | CONNECTOR DB25F AMP 745389-1 |
| U4 | DS1243 |
| U5, U6, U7 | DL3416 SIEMENS |
| U8 | ADC0834 TI |
| U9 | MAX233 |
| D1 | IN5291 |
| U3 | 27256 |
| U11 | UA7805UC FAIRCHILD |
| C4 | 4700 Mfd |
| PCB 1 | Printed circuit board |
| JP3 | Female RJ-11 (6 pos-4 wire) |
| JP1 | HEADER 4 |
| | AC line cord |
| R17 | MMSI TRANSDUCER |
| U10 | LM324 |
| R5 | 10K DIP |
| R7, R9, R10, R11 | 10K DIP |
| K6 | 10K-15T VRN 752-208-103 |
| R12, R13 | 100K |
| R2 | 10K |
| C6, C8, C9, C10, C11, C12, C13 | .01 Mfd |
| C15, C16 | .2 Mfd |
| T1 | Toltek Custom |

TABLE I-continued

| Schematic Reference | Part |
|---|---|
| | transformer |
| D2 | GI 2KBP04 |
| F1 | .25 AMP |
| SW1 | Micro Switch & Cover |

TABLE II

| Schematic Reference | Part |
|---|---|
| Y1 | CST 4.19 MHZ (KYOCERA) |
| U2 | LM324DT (SGS) |
| B1, B2 | CR20162HM (Panasonic) |
| RN1 | 100K (CTS) |
| R1, R3, R4, R6, R8 | NRC12100KFTR (NIC) |
| R2 | NRC127.32KFTR (NIC) |
| R5 | NRC121MEGFTR (NIC) |
| U1 | NEC75328GC173/3B9 (NEC) |
| D1, D2, D3, D4 | MTBL3410 (MARKTECH) |

What is claimed is:

1. A system for monitoring the inflation or deflation of a balloon-type member and for selectively recording and displaying inflation or deflation data, the system comprising:

a syringe adapted for connection to the member through tubing, the syringe comprising a barrel and a plunger selectively operable to inflate the member by applying fluid pressure to the member through the tubing by sliding the plunger within the barrel, and operable to deflate the member by withdrawing the plunger from the barrel;

transducer means, adapted for placement in fluid communication with the fluid pressure applied to inflate or deflate said member, for sensing fluid pressure and outputting an electrical signal proportional to the sensed fluid pressure;

RF transmission means, mounted to said syringe and electrically connected to said transducer means, for receiving the electrical pressure signal and for wirelessly transmitting via a predetermined radio frequency transmission data that is derived from the electrical pressure signal;

remote console means, positioned a predetermined distance away from said RF transmission means, for wirelessly receiving said transmission data transmitted by said RF transmission means and for electronically processing said transmission data so as to derive and so as to display or record therefrom inflation or deflation data representing the magnitude of said fluid pressure applied to said member and the length of time said fluid pressure is applied to said member; and display means, electrically connected to said remote console means, for outputting a visual display of the inflation or deflation data.

2. A system as defined in claim 1 further comprising a power means for providing electrical power to the transducer means and the RF transmission means.

3. A system as defined in claim 2 wherein the power means comprises a battery.

4. A system as defined in claim 2 wherein the transducer means and the power means are mounted to the syringe barrel.

5. A system as defined in claim 1 wherein the transducer means comprises a piezoresistive semiconductor transducer.

6. A system as defined claim 1 wherein the RF transmission means comprises:

means for amplifying and conditioning the electrical pressure signal;

means for converting the amplified electrical pressure signal from an analog to a digital form;

digital processor means for processing the digital form of the electrical pressure signal so as to derive therefrom transmission data;

data memory means for storing the transmission data derived by the digital processor means;

program memory means for storing machine-readable instructions utilized by the digital processor means to derive and store the transmission data for transmission; and RF transmission circuit means for wirelessly transmitting the transmission data as an RF signal having a predetermined radio frequency.

7. A system as defined in claim 1 wherein the remote console means comprises:

RF receiver circuit means for receiving the transmission data transmitted by said RF transmission means;

second digital processor means for monitoring the received transmission data and for processing the received transmission data so as to derive, store and display inflation or deflation data which represents the magnitude of the applied pressure and the length of time the pressure is applied to the member;

second data memory means for storing the inflation or deflation data derived by the second digital processor means; and second program memory means for storing machine-readable instructions utilized by the second digital processor means to monitor the received transmission data and to derive, store, retrieve and display the inflation or deflation data.

8. A system as defined claim 1 wherein the RF transmission means comprises a control panel, the control panel comprising:

first switch means for selecting a menu display for presentation at said display means a plurality of optionally selectable functions to be performed by said remote console means; and second switch means for entering to said remote console means data identifying choices selected with respect to any of said plurality of functions.

9. A system as defined in claim 8 wherein the selected function is comprised of at least one of the following:

(1) retrieving and reviewing all previously stored inflation or deflation data;

(2) clearing all inflation or deflation data previously stored by said remote console means;

(3) setting a maximum positive inflation pressure value;

(4) setting a maximum inflation time value;

(5) selecting units of inflation pressure;

(6) initializing date and time; and (7) priming data stored in said remote console means.

10. A system as defined in claim 8 wherein the first switch means comprises a first elastomeric button switch, and the second switch means comprises a second elastomeric button switch, and wherein the first and the second elastomeric button switches both comprise means for preventing entry of liquids into the RF transmission means at said button switches.

11. A system for monitoring the inflation or deflation of a balloon-type member and for selectively recording and displaying inflation or deflation data, the system comprising:

a syringe adapted for connection to the member through tubing, the syringe comprising a barrel and a plunger selectively operable to inflate the member by applying fluid pressure to the member through the tubing by sliding the plunger within the barrel, and operable to deflate the member by withdrawing the plunger from the barrel;

transducer means for sensing a fluid pressure and for outputting an electrical pressure signal proportional to the sensed fluid pressure, the transducer means being placed in fluid communication with the fluid pressure within the syringe and the tubing connected thereto;

RF transmission means, mounted to said syringe and electrically connected to said transducer means, for receiving the electrical pressure signal and for wirelessly transmitting via a predetermined radio frequency transmission data that is derived from the electrical pressure signal;

remote console means, positioned a predetermined distance away from said RF transmission means, for wirelessly receiving said transmission data transmitted by said RF transmission means and for electronically processing said transmission data so as to derive and so as to display or record therefrom inflation or deflation data representing the magnitude of said fluid pressure applied to said member and the length of time said fluid pressure is applied to said member;

display means, electrically connected to said remote console means, for outputting a visual display of the inflation or deflation data; and a control panel disposed on the RF transmission means, the control panel comprising switch means for selectively controlling the remote console means to perform at least one of a plurality of optionally selectable functions.

12. A system as defined in claim 11 wherein the optionally selected function is comprised of at least one of the following:

(1) retrieving and reviewing all previously stored digital data;

(2) clearing all digital data previously stored by said remote console means;

(3) setting a maximum positive inflation pressure value;

(4) setting a maximum inflation time value;

(5) selecting units of inflation pressure;

(6) initializing date and time; and (7) printing data stored in said remote console means.

13. A system as defined in claim 12 wherein the switch means comprises:

first switch means for selecting a menu display for presentation at said display means of the plurality of optionally selectable functions; and second switch means for entering to said remote console means data identifying choices selected with to any of said plurality of optionally selectable functions.

14. A system as defined in claim 13 wherein the first switch means comprises a first elastomeric button switch, and the second switch means comprises a second elastomeric button switch, and wherein the first and the second elastomeric button switches both comprise means for preventing entry of liquids into the RF transmission means at said button switches.

15. A system as defined claim 14 wherein the transmission means comprises:

means for amplifying and conditioning the electrical pressure signal;

means for converting the amplified electrical pressure signal from an analog to a digital form;

digital processor means for processing the digital form of the electrical pressure signal so as to derive therefrom transmission data;

data memory means for storing the transmission data derived by the digital processor means;

program memory means for storing machine-readable instructions utilized by the digital processor means to derive and store the transmission data for transmission; and RF transmission circuit means for wirelessly transmitting the transmission data as an RF signal having a predetermined radio frequency.

16. A system as defined in claim 15 wherein the remote console means comprises:

RF receiver circuit means for receiving the transmission data transmitted by said RF transmission circuit means;

second digital processor means for monitoring the received transmission data and for processing the received transmission data so as to derive, store and display inflation or deflation data which represents the magnitude of the applied pressure and the length of time the pressure is applied to the member;

second data memory means for storing the inflation or deflation data derived by the second digital processor means; and second program memory means for storing machine-readable instructions utilized by the second digital processor means to monitor the received transmission data and to derive, store, retrieve and display the inflation or deflation data.

17. A system as defined in claim 16 further comprising a power means for providing electrical power to the transducer means and the RF transmission means.

18. A system as defined in claim 17 wherein the power means comprises a battery.

19. A system as defined in claim 18 wherein the transducer means comprises a piezoresistive semiconductor transducer.

* * * * *

UNITED STATES PATENT AND TRADEMARK OFFICE
CERTIFICATE OF CORRECTION

PATENT NO. : 5,453,091
DATED : September 26, 1995
INVENTOR(S) : STEVEN R. TAYLOR et al.

It is certified that error appears in the above-indentified patent and that said Letters Patent is hereby corrected as shown below:

Title page, item [56], column 2, line 5, "Tha" should be --The--
    Title page (back side), column 2, line 12 of "Other Publications, "produce prochure" should be --product brochure--
    Column 3, line 61, delete second occurrence of "and"
    Column 6, line 63, delete "lo" (PTO error)
    Column 14, line 25, "oscillator 449" should be --oscillator circuit 449--
    Column 16, line 26, delete "a"
    Column 24, line 56, "awaits for" should be --waits for--
    Column 27, line 1, "as defined claim 1" should be --as defined in claim 1--
    Column 27, line 62, "priming data" should be --printing data--
    Column 28, line 62, "with to" should be --with respect to--

Signed and Sealed this

Fourth Day of June, 1996

*Attest:*

BRUCE LEHMAN

*Attesting Officer*    *Commissioner of Patents and Trademarks*